US009783857B2

(12) United States Patent
An et al.

(10) Patent No.: US 9,783,857 B2
(45) Date of Patent: Oct. 10, 2017

(54) DIAGNOSIS KIT AND CHIP FOR BLADDER CANCER USING BLADDER CANCER SPECIFIC METHYLATION MARKER GENE

(71) Applicant: GENOMICTREE, INC., Daejeon (KR)

(72) Inventors: Sung Whan An, Daejeon (KR); Young Ho Moon, Daejeon (KR); Tae Jeong Oh, Daejeon (KR)

(73) Assignee: GENOMICTREE, INC., Daejeon (KR)

( * ) Notice: Subject to any disclaimer, the term of this patent is extended or adjusted under 35 U.S.C. 154(b) by 0 days.

(21) Appl. No.: 15/586,029

(22) Filed: May 3, 2017

(65) Prior Publication Data

US 2017/0240977 A1 Aug. 24, 2017

Related U.S. Application Data

(60) Continuation-in-part of application No. 15/016,424, filed on Feb. 5, 2016, now Pat. No. 9,670,552, which is a continuation-in-part of application No. 13/627,474, filed on Sep. 26, 2012, now Pat. No. 9,365,900, which is a division of application No. 12/744,491, filed as application No. PCT/KR2008/007081 on Dec. 1, 2008, now abandoned.

(30) Foreign Application Priority Data

Nov. 30, 2007 (KR) ........................ 10-2007-0124015

(51) Int. Cl.
*C12Q 1/68* (2006.01)

(52) U.S. Cl.
CPC ..... *C12Q 1/6886* (2013.01); *C12Q 2600/154* (2013.01)

(58) Field of Classification Search
None
See application file for complete search history.

(56) References Cited

U.S. PATENT DOCUMENTS

| | | | | |
|---|---|---|---|---|
| 5,786,146 | A | 7/1998 | Herman et al. | |
| 6,812,339 | B1 | 11/2004 | Venter et al. | |
| 7,354,713 | B2 | 4/2008 | Mertz et al. | |
| 7,972,772 | B2 | 7/2011 | Nakamura et al. | |
| 8,062,892 | B2 | 11/2011 | Schlegel et al. | |
| 8,173,602 | B2 | 5/2012 | Albertson et al. | |
| 8,513,028 | B2 | 8/2013 | Jang et al. | |
| 9,359,646 | B2 | 6/2016 | An et al. | |
| 9,365,900 | B2 * | 6/2016 | An ...................... | C12Q 1/6886 |
| 9,670,552 | B2 * | 6/2017 | An ...................... | C12Q 1/6886 |
| 2002/0137086 | A1 * | 9/2002 | Olek .................... | C12Q 1/6809 435/6.16 |
| 2007/0298506 | A1 | 12/2007 | Ordway et al. | |
| 2010/0304992 | A1 | 12/2010 | An et al. | |
| 2013/0122495 | A1 | 5/2013 | An et al. | |
| 2013/0123116 | A1 | 5/2013 | An et al. | |
| 2016/0244843 | A1 | 8/2016 | An et al. | |
| 2016/0244844 | A1 | 8/2016 | An et al. | |

FOREIGN PATENT DOCUMENTS

| | | | | |
|---|---|---|---|---|
| CA | 2288235 | A1 | 12/1998 | |
| DE | 20121960 | U1 | 1/2004 | |
| JP | 2002511749 | A | 4/2002 | |
| KR | 1020110049430 | A | 5/2011 | |
| KR | 1020120055917 | A | 6/2012 | |
| WO | 0119845 | A1 | 3/2001 | |
| WO | WO 0119845 | A1 * | 3/2001 | ........... C07K 14/705 |
| WO | 2007143037 | A2 | 12/2007 | |

OTHER PUBLICATIONS

Old; Candidate epigenetic biomarkers for noninvasive prenatal diagnosis of Down syndrome; Reproductive BioMedicine Online; vol. 15, No. 2; pp. 227-235; Jun. 21, 2007.*

Ahlquist, D., et al., "Colorectal Cancer Screening by Detection of Altered Human DNA in Stool: Feasibility of a Vlultitarget Assay Panel", "Gastroenterology", Nov. 2000, pp. 1219-1227, vol. 119, No. 5.

Bai, F., et al., "Establishment and characterization of a high metastatic potential in the peritoneum for human gastric aancer by orthotopic tumor cell implantation", "Dig Dis Sci.", Apr. 3, 2007, pp. 1571-1578, vol. 52, No. 6.

Chan, M., et al., "Hypermethlyation of Multiple Genes in Tumor Tissues and Voided Urine in Urinary Bladder Cancel Patients", "Clinical Cancer Research", Feb. 2002, pp. 464-470, vol. 8, No. 2.

Comb, M., et al., "CpG methylation inhibits proenkephalin gene expression and binding of the transcription factor AP-2", "Nucleic Acids Research", Jul. 11, 1990, pp. 3975-3982, vol. 18, No. 13.

Costello, J., et al., "Aberrant CpG-island methylation has non-random and tumour-type-specific patterns", "Nature Genetics", Feb. 2000, pp. 132-138, vol. 25.

Das, P., et al., "DNA Methylation and Cancer", "Journal of Clinical Oncology", Nov. 15, 2004, pp. 4632-4641, vol. 22.

Esteller, M., et al., "Detection of Aberrant Promoter Hypermethylation of Tumor Suppressor Genes in Serum DNA from Non-Small Cell Lung Cancer Patients", "Cancer Research", Jan. 1, 1999, pp. 67-70, vol. 59.

Fraga, M., et al., "The affinity of different MBD proteins for a specific methylated locus depends on their intrinsic binding properties", "Nucleic Acids Research", Mar. 15, 2003, pp. 1765-1774, vol. 31, No. 6.

(Continued)

*Primary Examiner* — Antonio Galisteo Gonzalez
(74) *Attorney, Agent, or Firm* — Hultquist, PLLC; Steven J. Hultquist

(57) ABSTRACT

The present invention relates to a kit and nucleic acid chip for diagnosing bladder cancer using a bladder cancer-specific marker gene. More particularly, the invention relates to a kit and nucleic acid chip for diagnosing bladder cancer, which can detect the promoter methylation of a bladder cancer-specific gene, the promoter or exon region of which is methylated specifically in transformed cells of bladder cancer. The use of the diagnostic kit or nucleic acid chip of the invention enables diagnosis of bladder cancer at an early stage of transformation, thus enabling early diagnosis of bladder cancer, and can diagnose bladder cancer in a more accurate and rapid manner compared to a conventional method.

21 Claims, 14 Drawing Sheets

(56) References Cited

OTHER PUBLICATIONS

Fukushima, N., et al., "Aberrant methylation of preproenkephalin and p16 genes in pancreatic intraepithelial neoplasia and pancreatic ductal adenocarcinoma", "American Journal of Pathology", May 2002, pp. 1573-1581, vol. 160.
Goo, Y., et al., "Stromal mesenchyme cell genes of the human prostate and bladder", "BMC Urology", Dec. 2005, pp. 1-11, vol. 5.
Ho, S., et al., "Techniques used in studies of epigenome dysregulation due to aberrant DNA methylation: An emphasis on fetal-based adult diseases", "Reproductive Toxicology", Apr.-May 2007, pp. 267-282, vol. 23.
Hoehn, B., et al., "Abstract 4517: Syndecan-2 methylation is an early detection biomarker for colorectal cancer with high sensitivity and specificity in small serum sample volumes", "Cancer Research", Apr. 15, 2012, p. 4517 vol. 72 (8 Supplement).
"Illumina DNA Methylation Analysis Data Sheet", "Data Sheet: Epigenetics", Apr. 6, 2012, pp. 1-7; (http://www.illumina.com/Documents/products/datasheets/datasheet_dna_methylation_analysis.pdf).
Jan, K., et al., "Abnormal DNA methylation according to the histologic types of early gastric adenocarcinoma", "Histopathology", Sep. 5, 2012, pp. 76-77, vol. 61 (Supplement 1).
Kawamoto, K., et al., "p161NK4a and p14ARF methylation as a potential biomarker for human bladder cancer", "Biochemical and Biophysical Research Communications", Jan. 20, 2006, pp. 790-796, vol. 339, No. 3.
Kristensen, E., et al., "A Novel 3-D Image-Based Morphological Method for Phenotypic Analysis", "IEEE Transaction on Biomedical Engineering", Dec. 2008, pp. 2826-2831, vol. 55, No. 12.
Liu, T., et al., "Regulation of Cdx2 expression by promoter methylation, and effects of Cdx2 transfection on morphology and gene expression of human esophageal epithelial cells", "Carcinogenesis", Sep. 21, 2006, pp. 488-496, vol. 28, No. 2.
Marsit, C., et al., "Examination of a CpG Island Methylator Phenotype and Implications of Methylation Profiles in Solid Tumors", "Cancer Research", Nov. 1, 2006, pp. 10621-10629, vol. 66, No. 21.
Matsusaka, K., et al., "Classification of Epstein-Barr Virus-Positive Gastric Cancers by Definition of DNA Methylation Epigenotypes", "Cancer Research", Dec. 1, 2011, pp. 7187-7197, vol. 71, No. 23.
Old, R., et al., "Candidate epigenetic biomarkers for non-invasive prenatal diagnosis of Down syndrome", "Reproductive Biomedicine Online", Aug. 2007, pp. 227-235, vol. 15, No. 2.
"Promega's Protocols & Applications Guide Chapter 1: Nucleic Acid Amplification", "Promega's Protocols & Applications Guide", Mar. 2011, pp. 1-26.
Sambrook, J., et al., "Molecular Cloning: A Laboratory Manual: Second Edition", 1989, pp. v-xxxii (Table of contents only), Publisher: Cold Spring Harbor Laboratory Press, Published in: US.
Sanchez-Cespedes, M., et al., "Gene Promoter Hypermethylation in Tumors and Serum of Head and Neck Dancer Patients", "Cancer Research", Feb. 15, 2000, pp. 892-895, vol. 60.
Sato, F., et al., "CpG Island Hypermethylation in Progression of Esophageal and Gastric Cancer", "Cancer", Dec. 16, 2005, pp. 483-493, vol. 106, No. 3.
Schulz, W., "DNA methylation in urological malignancies (review)", "International Journal of Oncology", Jul. 1998, pp. 151-167, vol. 13.
Strachan, T., et al., "Human Molecular Genetics. 2nd edition Chapter 5: Nucleic acid hybridization assays", 1999, pp. 95-118, Publisher: John Wiley & Sons, Inc. (by arragement with BIOS Scientific Publishers Ltd), Published in: New York, NY USA.
Suh, N., et al., "Value of CDX2, villin, and alpha-methylacyl coenzyme A racemase immunostains in the distinction between primary adenocarcinoma of the bladder and secondary colorectal adenocarcinoma", "Modern Pathology", Sep. 2005, pp. 1217-1222, vol. 18, No. 9.
Tanay, A., et al., "Hyperconserved CpG domains underlie Polycomb-binding sites", "PNAS", Mar. 27, 2007, pp. 5521-5526, vol. 104.
Ueki, T., et al., "Identification and characterization of differential! menthylated CpG islands in pancreatic carcinoma", "Cancer Research", Dec. 2001, pp. 8540-8546, vol. 61.
"Unpublished U.S. Appl. No. 15/585,716, filed May 3, 2017".
Uitikal, J., et al., "The expression of metastasis suppressor MIM/MTSS1 is regulated by DNA methylation", "International Journal of Cancer", Nov. 16, 2006, pp. 2287-2293, vol. 119, No. 10.
Wiksten, J., et al., "Epithelial and stromal syndecan-1 expression as predictor of outcome in patients with gastric cancer", "Int. J. Cancer (Pred. Oncol.)", Jan. 20, 2001, pp. 1-6, vol. 95.
Yamaki, A., et al., "Molecular mechanisms of human single minded2 (SIM2) gene expression: identification of a promrter site in the SIM2 genomic sequence", "Gene", May 2001, pp. 265-275, vol. 270.
Yates, D., et al., "Promoter Hypermethylation Identifies Progression Risk in Bladder Cancer", "Clinical Cancer Research", Apr. 1, 2007, pp. 2046-2053, vol. 13, No. 7.
Zouridis, H., et al., "Methylation Subtypes and Large-Scale Epigenetic Alterations in Gastric Cancer", "Science Translational Medicine", Oct. 17, 2012, pp. 1-12, vol. 4, No. 156.

* cited by examiner

* Cut-off: methylation index value of cut-off for diagnosis of bladder cancer
* Sensitivity: Sensitivity for diagnosis of cancer
* Specificity: Specificity for diagnosis of cancer
* p value: p value of logistic regression analysis test

SEQUENCE LISTING

<160> NUMBER OF SEQ ID NOS: 461

<210> SEQ ID NO 1
<211> LENGTH: 24
<212> TYPE: DNA
<213> ORGANISM: Artificial Sequence
<220> FEATURE:
<223> OTHER INFORMATION: Synthetic Construct

<400> SEQUENCE: 1
tggtgtttgt gttattatta atag 24

<210> SEQ ID NO 2
<211> LENGTH: 21
<212> TYPE: DNA
<213> ORGANISM: Artificial Sequence
<220> FEATURE:
<223> OTHER INFORMATION: Synthetic Construct

<400> SEQUENCE: 2
cacctccttc ccactaaact a 21

<210> SEQ ID NO 3
<211> LENGTH: 19
<212> TYPE: DNA
<213> ORGANISM: Artificial Sequence
<220> FEATURE:
<223> OTHER INFORMATION: Synthetic Construct

<400> SEQUENCE: 3
gtaagggtat gggaattga 19

<210> SEQ ID NO 4
<211> LENGTH: 22
<212> TYPE: DNA
<213> ORGANISM: Artificial Sequence
<220> FEATURE:
<223> OTHER INFORMATION: Synthetic Construct

<400> SEQUENCE: 4
cccttaaaaa cctaacaaaa tc 22

<210> SEQ ID NO 5
<211> LENGTH: 21
<212> TYPE: DNA
<213> ORGANISM: Artificial Sequence
<220> FEATURE:
<223> OTHER INFORMATION: Synthetic Construct

<400> SEQUENCE: 5
ggagtgggat tgaggagatt t 21

<210> SEQ ID NO 6
<211> LENGTH: 19
<212> TYPE: DNA
<213> ORGANISM: Artificial Sequence
<220> FEATURE:
<223> OTHER INFORMATION: Synthetic Construct

<400> SEQUENCE: 6
aaacccaacc aaccctcat 19

<210> SEQ ID NO 7
<211> LENGTH: 23
<212> TYPE: DNA
<213> ORGANISM: Artificial Sequence
<220> FEATURE:
<223> OTHER INFORMATION: Synthetic Construct

<400> SEQUENCE: 7
agtaagttta tgggaggggg att 23

<210> SEQ ID NO 8
<211> LENGTH: 25
<212> TYPE: DNA
<213> ORGANISM: Artificial Sequence
<220> FEATURE:
<223> OTHER INFORMATION: Synthetic Construct

<400> SEQUENCE: 8
cccccataca acatacttat actca 25

<210> SEQ ID NO 9
<211> LENGTH: 26
<212> TYPE: DNA
<213> ORGANISM: Artificial Sequence
<220> FEATURE:
<223> OTHER INFORMATION: Synthetic Construct

<400> SEQUENCE: 9
ggaggaatgt tattgtttaa agagat 26

<210> SEQ ID NO 10
<211> LENGTH: 22
<212> TYPE: DNA
<213> ORGANISM: Artificial Sequence
<220> FEATURE:
<223> OTHER INFORMATION: Synthetic Construct

<400> SEQUENCE: 10
caaccccttc taaaaaatat cc 22

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
gggtttggag ttaggttatg 20

<210> SEQ ID NO 12
<211> LENGTH: 22
<212> TYPE: DNA
<213> ORGANISM: Artificial Sequence
<220> FEATURE:
<223> OTHER INFORMATION: Synthetic Construct

<400> SEQUENCE: 12
aaatctaaac ttacccccaa ct 22

<210> SEQ ID NO 13
<211> LENGTH: 28
<212> TYPE: DNA
<213> ORGANISM: Artificial Sequence
<220> FEATURE:
<223> OTHER INFORMATION: Synthetic Construct

<400> SEQUENCE: 13
atattttatt gtatgggttt tttaatag 28

-continued

<210> SEQ ID NO 14
<211> LENGTH: 19
<212> TYPE: DNA
<213> ORGANISM: Artificial Sequence
<220> FEATURE:
<223> OTHER INFORMATION: Synthetic Construct

<400> SEQUENCE: 14
acaacctcaa caaaaaatc 19

<210> SEQ ID NO 15
<211> LENGTH: 19
<212> TYPE: DNA
<213> ORGANISM: Artificial Sequence
<220> FEATURE:
<223> OTHER INFORMATION: Synthetic Construct

<400> SEQUENCE: 15
agatagggga taattttat 19

<210> SEQ ID NO 16
<211> LENGTH: 18
<212> TYPE: DNA
<213> ORGANISM: Artificial Sequence
<220> FEATURE:
<223> OTHER INFORMATION: Synthetic Construct

<400> SEQUENCE: 16
cctcccaaac taaaattt 18

<210> SEQ ID NO 17
<211> LENGTH: 23
<212> TYPE: DNA
<213> ORGANISM: Artificial Sequence
<220> FEATURE:
<223> OTHER INFORMATION: Synthetic Construct

<400> SEQUENCE: 17
gtagaaggga aataaggttg aaa 23

<210> SEQ ID NO 18
<211> LENGTH: 21
<212> TYPE: DNA
<213> ORGANISM: Artificial Sequence
<220> FEATURE:
<223> OTHER INFORMATION: Synthetic Construct

<400> SEQUENCE: 18
actaaaaccc caatactccc a 21

<210> SEQ ID NO 19
<211> LENGTH: 23
<212> TYPE: DNA
<213> ORGANISM: Artificial Sequence
<220> FEATURE:
<223> OTHER INFORMATION: Synthetic Construct

<400> SEQUENCE: 19
gtggatttag attaggattt tgt 23

<210> SEQ ID NO 20
<211> LENGTH: 18
<212> TYPE: DNA
<213> ORGANISM: Artificial Sequence
<220> FEATURE:
<223> OTHER INFORMATION: Synthetic Construct

<400> SEQUENCE: 20
caccctcccc aaattctt 18

<210> SEQ ID NO 21
<211> LENGTH: 22
<212> TYPE: DNA
<213> ORGANISM: Artificial Sequence
<220> FEATURE:
<223> OTHER INFORMATION: Synthetic Construct

<400> SEQUENCE: 21
attaatagag ttttgtaaat at 22

<210> SEQ ID NO 22
<211> LENGTH: 16
<212> TYPE: DNA
<213> ORGANISM: Artificial Sequence
<220> FEATURE:
<223> OTHER INFORMATION: Synthetic Construct

<400> SEQUENCE: 22
aagggtatgg gaattg 16

<210> SEQ ID NO 23
<211> LENGTH: 15
<212> TYPE: DNA
<213> ORGANISM: Artificial Sequence
<220> FEATURE:
<223> OTHER INFORMATION: Synthetic Construct

<400> SEQUENCE: 23
tttgggattg ggaag 15

<210> SEQ ID NO 24
<211> LENGTH: 24
<212> TYPE: DNA
<213> ORGANISM: Artificial Sequence
<220> FEATURE:
<223> OTHER INFORMATION: Synthetic Construct

<400> SEQUENCE: 24
tagtttaggg tattttttat ttat 24

<210> SEQ ID NO 25
<211> LENGTH: 24
<212> TYPE: DNA
<213> ORGANISM: Artificial Sequence
<220> FEATURE:
<223> OTHER INFORMATION: Synthetic Construct

<400> SEQUENCE: 25
gtgaaagtaa tgatatagta gaaa 24

<210> SEQ ID NO 26
<211> LENGTH: 15
<212> TYPE: DNA
<213> ORGANISM: Artificial Sequence
<220> FEATURE:
<223> OTHER INFORMATION: Synthetic Construct

<400> SEQUENCE: 26
tttgggggtt gggga 15

<210> SEQ ID NO 27

<211> LENGTH: 17
<212> TYPE: DNA
<213> ORGANISM: Artificial Sequence
<220> FEATURE:
<223> OTHER INFORMATION: Synthetic Construct

<400> SEQUENCE: 27
gggtgtttta ggtagtt 17

<210> SEQ ID NO 28
<211> LENGTH: 19
<212> TYPE: DNA
<213> ORGANISM: Artificial Sequence
<220> FEATURE:
<223> OTHER INFORMATION: Synthetic Construct

<400> SEQUENCE: 28
cctcccaaac taaaatttc 19

<210> SEQ ID NO 29
<211> LENGTH: 15
<212> TYPE: DNA
<213> ORGANISM: Artificial Sequence
<220> FEATURE:
<223> OTHER INFORMATION: Synthetic Construct

<400> SEQUENCE: 29
tgggggtaga ggaga 15

<210> SEQ ID NO 30
<211> LENGTH: 16
<212> TYPE: DNA
<213> ORGANISM: Artificial Sequence
<220> FEATURE:
<223> OTHER INFORMATION: Synthetic Construct

<400> SEQUENCE: 30
cctccccaaa ttcttc 16

<210> SEQ ID NO 31
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 31
actgcccttc tctcaatgat tcggattttg taacggggtt tgcaatttgc ttccggttgt 60
atttctcagg aagtccgatg acactcggct gtccaggcca ggcgctggaa gtcccccagg 120
aggaccagct cggtctccca cctcttgagt gcacagctcc ttggcccctg agtaccccac 180
cacccccatt tccagccttc ttccttacaa acacgaaggg tgggaggaac cagaaaacag 240
gggatcccgc agccctaggc tagttctgat cgctttcagg tgtctgcaga ggcaagttgc 300
tggttgtcac ctgtaaaatg gggaggataa aaacacctcc cagattttgt tctagatcct 360
agggggatgt gaggctcaag ggagataaag gacactggag agcaccctag aaatgacagg 420
atgaaggcga tggtgacaaa tatccgagcg aaacgcttga caatgagaac agacaagtgc 480
aggtctccag gagtgccgcg agcgcccgcg ggttctgaga gcgctcaaag ccgccgagtc 540
aggctgccca gcccgccggg cctcgccgca gtgatcctca ttcccgaatc tggcagcgct 600
gtcaaaggct tgtattagga ggtgaacggc ggccgcaggc ccactccacg cggttgctga 660
aaccgagctg ggcgcgcgcg ggggccgaat ctcgccgcct ccgcgctcct gtcggggcag 720
ctcccgatcc cgggctgcgc ggcttcggtc cccaagacgg ccacttccag ccctaggccc 780
cttggccgca gcgcttccca aaccaagaga gatcctttct caactcagag cttttcatta 840
gcagtcgtta ataatggccc tgagttgcct tatcatctcc tggaaatgag aaataaattt 900
cttcggagaa cgtttccctt tgtaaaggac agagagtttt aaagatacag gtatgatgta 960
agacacataa atacctaggt aagcattagc agaaattctc ttttccttat atttaagtat 1020
aataaacata caagtgtagc tcaatgaatt ttcacaaact gacattctgt gtaaccagca 1080
gcctaagaaa ctgctttacc aacgatcccc tagctcgcct ccagttatgc acgccaataa 1140
ccactagcct aacttctacc acatgcccat tacttctgta gtttaaaact tctgattctt 1200
gaatgtaaac gtttaacaat aaatcgcttg aatttaactc aaatttcaaa tgtaagatga 1260
agtcagagat gcagcctgaa tctaggatca taatttgtct tgtgcggagg gcgagtaatt 1320
tccttgggca agaaaataac tggaggtgac agttgtttgg ggctgcagtc gtccgggcca 1380
ggagcacagg gcgggaagga atggcccatc tcttagggct ctctgcttgt cacctaccag 1440
gttggtcaga aacgttctca tcaaagcaat ggttctcttt tcttttctct ttgggacaga 1500
aggagtttct tgaccgccct cttccctgca aatgcataaa caaccactgc tcctgtctcc 1560
aagctcagat tcctaccaag atagcctttt ctcttcccct ctcttttgta agtctcttga 1620
tttcattctt tgaacctgtg attggaggtt aaagtgcacc aggttggaag gaggaagctc 1680
ttaacaataa aggtttgaat atttagctgt gtcaggtcgc tgccctctca cgagcctccc 1740
tcccctttat cttttaaaat gcaaattatg tttcgagggg ttgtgcgtag agtgcgcgct 1800
gcgcctcgac gtctccaacc attggtgtct gtgtcattac taatagagtc ttgtaaacac 1860
tcgttaatca cggaaggccg ccggcctggg gctccgcacg ccagcctgtg gcgggtcttc 1920
cccgcctctg cagcctagtg ggaaggaggt gggaggaaag aaggaagaaa gggagggagg 1980
gaggaggcag gccagaggga 2000

<210> SEQ ID NO 32
<211> LENGTH: 2000
<212> TYPE: DNA
<213> ORGANISM: Artificial Sequence
<220> FEATURE:
<223> OTHER INFORMATION: Synthetic Construct
<400> SEQUENCE: 32
aggcgcgact gtgcgtgcgc agccgagggt ggtggcggcc ggcaccccac gccaagggtg 60
gtggtggccg gcaccccacc ctcggccgcc gcctccgcgt gtcaggtgcc gtgagaagcg 120
cgggaggagc ggccgcaggc agcgcccagg gatatgactg gagccgactt tccagaagcg 180
gcgcacgcaa agcccagctc cgcacgcaaa ggggaggcga cagcagaaac ttcaacccga 240
taaagttcgc cggagcgcgg agattcgcct cctcctgcca ctctccgccc cgctcgggtc 300
ccgccccgct agctccccca ggccccccca gtcgccccag cttggctccc cgccctgcgc 360
caacggcttc catcgcagcc tgggcggccc cgcgcccacc agcgggcggc gccacctgga 420
gtggcctcta cgcgggaaat ctcagggcca gctgcgcccc aggagccttt gtgtgcccaa 480
gcactgtcgg ggccccgggg cgggggagcg gctactttta gggattcctg atctcgccgc 540
aagaactgga aaaaatttag catgccaaag agcctccact gaggtggcaa tttgtttgcg 600
agaacctaag ataaaattta aacaaccaac caggggcgct gtgaggcaaa ccgctgccac 660
tacactggct ttccgggaag caagctcaag tcgcggagag ggaagggagg tcgtgcgctc 720
ggggcggggc gcgctcccaa gtcgagcgca gcggccgggg caggttgtac cgagcgtggt 780
tctggggaca ccgtgcggcc tcgattggag gtggctgtga tgaagcgcgg ttaccgcaca 840
atggaaacgt gggcacctcc gctcccatga aagcctgctg gtagagctcc gaggccggcc 900
ggtgcgcctg gacgggagtc cgggtcaaag cggcctggtg tgcggcgcgc cccgcccccc 960
gcaggccccg ccctgccagg tcgcgctgcc ctccttctac ccagtcctta aaacccggag 1020
gagcgggatg gcgcgctttg actctggagt gggagtggga gcgagcgctt ctgcgactcc 1080
agttgtgaga gccgcaaggg catgggaatt gacgccactc accgaccccc agtctcaatc 1140
tcaacgctgt gaggaaacct cgactttgcc aggtccccaa gggcagcggg gctcggcgag 1200
cgaggcaccc ttctccgtcc ccatcccaat ccaagcgctc ctggcactga cgacgccaag 1260
agactcgagt gggagttaaa gcttccagtg agggcagcag gtgtccaggc cgggctgcgg 1320
gttcctgttg acgtcttgcc ctaggcaaag gtcccagttc cttctcggag ccggctgtcc 1380
cgcgccactg gaaaccgcac ctccccgcag gtcagtctgt ctgccgaggc gctgcccggc 1440
gacctcttca gatggattat tacaggtagc gggtggcgtg gtaggtactt taaaggaaat 1500
caagcgccac cgcctcgatg cccgcagcgt tgtccccaga ttgcaggaac cgttacgcgc 1560
cttgcgggga ggggaagggt ttggcgctgg gttacagcga ggtggaaaca cgccccttct 1620
cttctccaag ggagagtggg ttggggatgg gaaggggcgt cttcggccat ttctccagag 1680
agtcagctcc gacctctcca cccaacggca ctcagtcccc agaggctggg gtaggggcgt 1740
ggggcgcccg ctcctgtctc tgcacccctg agtgtcacgc cttctcctct ctgtccccag 1800
catgggcacc agcctcagcc cgaacgaccc ttggccgcta aacccgctgt ccatccagca 1860
gaccacgctc ctgctactcc tgtcggtgct ggccactgtg catgtgggcc agcggctgct 1920
gaggcaacgg aggcggcagc tccggtccgc gcccccgggc ccgtttgcgt ggccactgat 1980
cggaaacgcg gcggcggtgg 2000

<210> SEQ ID NO 33
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 33
caaaatgagt ttaagacgat ccttcccgag gcgccgcggt cactatagag agtgtctgag 60
gctgggctcc taccgcctgg ccttttggtg tctttggatc actggctatc tactcggggt 120
ctgtcactcc cgtgatcgcc taccttccag ggagacctag gggagggaga ccccaagacc 180
tgtcccaggt gaggccactt ggtcggcacc cggggctgca ggcacggcgc ccgcgtccgc 240
cctcgcccct taggctttcc attcgcgggc gaccccggtc gggccacctt agaatcgact 300
accctgcctg cctgactggt ctcgggctac aaactgtgtg gaagcgtagg tatctcactt 360
aactgctacc ccaaattcgg atttacaaac gactacgcag tcccgaatgc ccaacgcctt 420
ccctaaaccc agagataaat ctgggggaaa attcctcgcg gagcggaaaa caacgccagc 480
gtctaaagcg ttctgccccg agctggagtg gttcaaaaga caatgatctc aaaagaaagt 540
gattgttttg gtaatcccgg gaacagcttg caagggggag atttgggtct tcctttagta 600
acggaaagtc aatgcgcagc ctcctgtaat tatccttatc ggaagcccct tgtttaatct 660
gcatgtttag cggaggcccc actcgaacgc gcagcgagtg ggagacccac tttgcagggc 720
ccaggctcgg gctccggtcc ctgcgtgcgc gcaggcagcc gcgccgggtt cccgcggagc 780

```
tcaggcgttt gctcctccct cgctgcggga cctcggactg taggaccctc agggagtggg    840

actgaggaga tctgcttccg gggttctggg attgggaagc gggggacgca gggctccgag    900

cgatgagggc tggttgggtt caaagcgcga accagtagtt acttacccac gtgcttgggg    960

ccaactttag cgaatatcag agtttcactg attattcaaa gaatcaggct ttctttgaat   1020

aatcgtgaaa ttggacaata aattgtaagc cccgatgaaa aggtgtgctt tccagtagac   1080

agactctatt ttatttcaat ttacctccct ccactcctcc ccaatttagg gttgctggat   1140

aaaatactga tacatactcc tacaaaaaaa aaaagccctc ctttttttatc tgaaatcaca   1200

tttcactgag ccgacagtgt tttgttggtt aaacctggta ccctgcccgt ctcagccccg   1260

ggcagtccac tcctctctct gcttctctcc ctttccccag ctcttgtgag tctgccaccc   1320

cctacagttc agcccgtgga gtgttgggga tggacctggg ggtggatttg gatggaggta   1380

gaatgaccat ggattaaagg gatggaggta ggatgaccat ggattaaata cacggttttc   1440

attcctttcc ccttggggat tttcagagaa ggccttctta caggaaggcc ttcgtggcac   1500

cggcggcgga ggtggagggc tggctgggga catatatggg gtagccatcg gggtgtggtt   1560

gggaatgggg tcctaggtct taataggcag ttgggtcgca tcaaagaagc ttcagggcag   1620

ctgggagtgg ggcctccacc cagagagtct ggaaggaagg agaaggccac gccaggatgt   1680

agaacttgcg acttttcgag ggacaggcag acagcggagt cactgtccct taccttcttt   1740

cctcccctcc ctcctagaat gggggtgggg tggggtgggg tgggctggac agaagagagg   1800

aggagaagga ggtgactgag gggactgcag ctgggtgggc ggtaaccgag gggaggggaa   1860

ctggtggcgt ccccatctcg cggggtccgg aacggcgacg cgcccgcgcc cagctgattg   1920

gagcccttca ggcctcccgc gcccgaccgg cagcccaatc ctataaagct tcctctaagc   1980

tgggccctcc gcaaacggga                                                2000
```

<210> SEQ ID NO 34
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 34

```
ttgtgataag caatccttgt aaaggtggtg gtggggggag gtggagagcc acataaacat     60

taatgctaat aaattagttt actcgactac agagtaatta cttcatatta ttgatattta    120

cagcaggtat tcaaatgcaa tggtaggcca ttatttggag aaaatacata ataagaatat    180

ttcttttcca gtgcaataca cgattagatt tgttattgag tcagttacag tcagctcagc    240

aataaataaa taaatcgatg ttgacactta aataccaaag atcttagagt ttatactcta    300

aatctcccca agatatgtaa ataactttgg ctatttcctg gagagggaaa aacaaaaggt    360

tatcttttta catatttttt tattttcctt cagcaacatc ccagatcctt ccaagaagag    420

agttgttggg aggcctcagg tctgggccct tctcagctcc tggctctgcc tggctgctct    480

gtgctctgtg tcctctcctt tctttcgctt cctccaaaca ttgctccttc aatcctgcag    540

gatggggagc atattttgcc ttcttaattt attttttttc ctcttctcaa gaaagctaga    600

ctcagagtat tgctatggcc tctctctatc cttagcacaa acctagcttt ttaaagacat    660

ccctgtttcc ccaggtgcag ggagttcggg aagcacctct cctttctctg gtattgtatt    720

cctcctgtgg aatgagcagt aggaaaggca cagagctctc tgagtttttg ccctgcacat    780
```

cccttgcttt cactctcaca cattgcaagg aaggagagta ggagagtagg tgggttaccc 840
ctttctcagc cacctctcct tggccctcag cccgtccttt ccacctccat tctccccaca 900
cccctggagc tctgtaagca gcctgatggg ccccccacga agatgcagca tacccaggag 960
aagtctcctc ggatgtcagc gcctctaaag cagcccaagg cttgcctcaa ttgcatggtt 1020
tcccgagtcc tcagctccag aagaccaggc agatgggtgg accggtgagc agcagggcag 1080
cccctgtgcc tctgtctctg ccgagtcact ccgaagcccg gcaggcagcg aggaggaggg 1140
agtttctcca aggacagaag gtgggatgaa gaggtaggca gggaagatga ggggagaggt 1200
ggatcccggg taagacgaag gcccttccgg gccctgcgga tcagtgacaa accgcgggga 1260
gaagccgttc tggctgttgg cggtttaggg acggaaggca ctaaagcgct tcggaagtga 1320
ccatgaatga gagagtgtaa tcaagtcacc gtgcaaatcg gacaagccac caggcaggca 1380
catccacggc ttcaaactct ggccccgaag gggttccggc tagggtcgga ggcagaggcg 1440
cttcccagag caagtctatg ggagggggac tgcgaagaag gggggtgcaaa tgcgagactc 1500 caggagaaca gactccgaga ccacaggcca cacagcgacg gactcccacc tggctatccc 1560
cagtccaggg catccctcac ccacccgggg agctgcgggt gggaggtggg gacgagagtt 1620
gagctctcac cgccctctgc acactcgaga acgaggaccc tgcaattgag cacaagcatg 1680
ctgcatgggg gcgcacccca gcctctccgc gcgcgccggg aggcccccca gccaacatga 1740
gttacaccgg cgattacgtg ctttcggtga gaacaccgag tgacgatctg ttgcttcccc 1800
tgaggtggct acaaagaaag gaagccggga gggaggggag aggaggaaaa aaaaaaaagg 1860 aaagggggg ggaaaaggcc cggactagct agcagcttgt caatttcaac atcgggtcac 1920
atgaccagca cctccctgct aaggatgggg atagatttcc acgtcagctt acgtctccaa 1980
atttctactt cacggatccg 2000

<210> SEQ ID NO 35
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 35
agcttcattg ttgcctgctt ctaaagataa atggctttgc tttttcagaa gggattgggc 60
ccaggaaaac tgcctctctg ggagtcgagt ggggtgtgtg tgtgtgtttt cttataaaat 120
gtttcaagca tgttttcggt gggacagttg catcctgagg cccagccata aggctttgtc 180
ttgtttttct ctgaatggct gggcttgcca aggagagata gaccctggga gcgaaacagc 240
tggcggtgcc tcagcccctc tttcctccca aggaagcgca ttgttattaa ctgggaattc 300
tttatagccg ggctggagga agttttggct gtaaactgtc atgcactgca gccttcgctg 360
aaaaggcgga gggagtgggc ctggtcctgg gaaccgagga acaaagatca gaaaatcagc 420
cacagaaagg ggaggaaaaa taaacgttag aaagtgaaga caggtgacac tacacaagtg 480
ctggccaaag tcggtgactt ccaacctcta cctcctccga cttgggtggt tcaattcctg 540
ggtcgtactc ttcaatgctt cagacattct ctctggagag tagaaatttt attacgcgtg 600
ttagaaacgg aatattcttt cctgctgaag ttgtattctt atttggccgt gcccctcctg 660
ttcggaacag ttttagagcg atctgttaaa ccctccagtc ttctttggcg cttcccgact 720
gtgggaaaag cggccgcgac gccgtccgag cgcaggggag ggatccagcc ttcgggactc 780
ctttgccctg aagccgcagg agaggtttcg ctcccgtgcc tagggttccg aggccctcaa 840

-continued

```
ttgcctggga cccaccctcg ttcctccttc acctcccctc cacttttccc ttttatctta    900

tcctcgggag gccttgggcc aaagcgatga cctcttagac attttaatac ccggagtaag    960

gagagtaaca cgcaccacgc tctcccccaa agcccaggac ccgatgagcc agtgaaggcg   1020

tgtcaggagg gtccggcgtc aggagcaaat gaggtccttt tggtgcctct ttctagaagg   1080

aaacttcccc acctcgggtc agccccctgg gaatatccat gcatcccaga catcaaaaga   1140

cactgagaaa tgcggacagg gactagacgc tccggcttcc tgactcgtcg gtgtaagttg   1200

gagaagggag agaaggagcc ctgtccccca cgggcggcag gcacccttcc ccgggactgg   1260

ctcctggcag ccctccgcat accgcgaggc gggtcgatcc ctcgagtccc gggcggggat   1320

ccctccttcg gcttccccag caattcccga ccccggagcg agcccggctg ggcgaggggc   1380

gaggggcagg gggcaggggg caggggagac ttagcgcggg gcgcagatac catgtccgcg   1440

ggaaagcccc cttgctaggg cgcaagactc ctctgaactc gctgccccac ccgatgcgca   1500

ggctttctct agaggggttg gggctggggt gcccgctcag gagaccggga aacagaggct   1560

gctacccgag gcaggccctc gtccagcgaa tgggcgaggt gtgcagaagc gcaaagccag   1620

gccttggaag gggagcttc tgcctccttc ccccttcctg ggctcccgtt ttaggaggaa    1680

tgttactgtt taaagagacc ccactgaact atttcctgct cattgtcacc tctccttcgc   1740

tctcctcgcg taagttctca ccgaaaggta ataaaacaac cgctgccgac accgcttggc   1800

gctgggccgg gcggggaaag cgccccgagt cccactagtc cggaccaccc cgccagcccc   1860

gaccttctcc caccttccgt gaaagcaatg acacagcaga aaccacgcac acgcctggca   1920

cactcgatgc gcgcgctgac ctcggcaaca agtcctgttt ttataagaga gcgaggagga   1980

cacttctcag aaggggttgt                                               2000
```

<210> SEQ ID NO 36
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 36

```
ataataacag ccagtattct tcccacatac ttccggtcaa aagtggggaa accagaaacc     60

gaataaaaca ttgggaagag acatactgtg ttcctggaaa aaatataaca gagccagatt    120

taactcggtg agagggaaag tgaccccctt gagaaaccag ggaatgtctc accctcagac    180

caaccctttc ttttgcaaat tgaattggtc aaagtttagt tttgtcatca tttctattgt    240

tataattctt attcattttc ccagccccgt ccacacttct atttttcact acccccacgc    300

cccacaagtt gccaccgggt caggtgggga catatccgga gagaaataga aagggatgca    360

ttttaaagcg agttctcttt tgagaggaaa acaatgggta gttttggaag tgtctttctt    420

aaaaacggaa ggagaaggtg aagaaaaaaa ttatcaacag caatgggccc ctttggtttg    480

ggttttgact ttttaaagag gaacctctgc tgtcctgttg cagtattaaa atcagggcag    540

gaattttgca aaatgagaaa aataaacttc gggagaaaac ccagctggga gcagcttcgg    600

gaaagcgaca gttctccgaa aggaggaagg gaggatgcgc gctgtagccg gctccggagt    660

ttactgcccg aacgattggg gaaaagaacg aggattctca aatctagttg cgatctctcg    720

tctctccttt attctgttcg tggtgcgggc ttcggagcgt ctgggaaagc cagtctgtga    780

agctggactt gcagaatcct ttgaatgccg gtccaggtgg ctgcagggcc cgcagtccgg    840
```

gatgccggag aaaggaacca caaggaaaag acgctacgct cggagtttcc ccttttcctt 900
gcagccccgg cggggcctag gcctcggttt ccggcccacc tcggctcaga ggtcaagtag 960
gaactcatct cgtcgaccta gggtttggga gaaggatttc gggttgcgtt cttggcatct 1020
gggagcaaac acgagcctcg gatttgggga catatcgtta ttaacagctt gggaaacgaa 1080
agcgaagctc ggggcagcca ctgcagcctg gctgagagaa aggacgcggg ttgtgctctc 1140
tggaagcaaa ggggtctgcg gcccagctgg cctgggagct tgtggccggc gctggaagct 1200
gcccgctctc cccgcgggcc tgaccttggc tcccgccgca gctctgccgg ccgactgcct 1260
ccctgcacat tttgctgccg ttccagtcct tacaggaccg ggcctggagc caggccatgc 1320
ttcggaaagc cctgggggtt ggggacgcgc aaaacccaga atcgaacccc gaagctgggg 1380
gcaagtccag attcagacgt ccagctccct cgggacccct tggcggagaa cttacccttc 1440
cggaaggccc gacgctctcc ggctctgtgc tgggcaggcc tagctcttct ctcggcgcca 1500
ccaggggcgt ctacgcggta cgttttgcaa ctcaacctag tgggtttcca gcggtgcgca 1560
aaagtttgcg agcatccacc actgcgctgc ttagaaattg tgcccattga tcagactaaa 1620
aataatagtc gtcgtgatta caaaacaaaa tagagtgcct cgtgcctcgg cgggccctgg 1680
tacaataatt attctctaca gaaaccacct ctctccactc ccacccctac tccaccaccc 1740
actcgcaccc cgcccctgcc gggccactct gggacgaatt gcattcttgg acctttctct 1800
ccgcaaggca cattacggag aactccctct gtctcgtgtc ccctccacga caacccagta 1860
attatttcta tgcaagtctg caagagggca ctgagttatc gcatcccaag cctaaccagc 1920
tagagcggcg cctcggtatt catttgccca gagctcctcc gcgggggatt taaaaataat 1980
aataataata ataaggatcc 2000

<210> SEQ ID NO 37
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 37
agcgactgta gaaatcagcc ctttgcagag ggcgcagagg gcctggaaac ctctgggacc 60
ttttcccagg aactgtttat ggtttccccc taggtctagg agacatagat gcataggtgg 120
attggataca tcgatggtag ctataaggta agcagacaat ggtcacagat ggaaaggtgg 180
acggacggat gacggatggt tagaagatgt tttgagggct tgctatagtg ccaggcacaa 240
ggctaagaga tttcgtccac tatttcattt gattctctcc agaaccttat gaatggcata 300
ttacctctgt tcctattttt caaataggga aactgaggcc tcaggcaatg taagcagctt 360
gccgcttagc aatcttttgc agagccagga agcgggaaag cgtgtcttaa tggacagtac 420
cagcctccac agtgtgccct cggccccctc ccggtggaga agaggttcca agccccggcg 480
tcccgggtag ggtgtccctc atccctccct ccccaccaca ctcctggcgc gctgacatta 540
cacccgcccc ggcacccccc tctcactgat ccaacacccc cggacaccct ggacagcgct 600
ctcaaggcag taggtcttcg acttgggagc cccggggagc tggttaaaca cggatcctct 660
cccacagtgg ctgaaaagcg cgcagtcccg gaacctgagg gtttacctgc ttctacgctt 720
ggccaagggt ctctaactgg aaaggtgaaa attctgtcct gagattttaa gattcccaga 780
aactttcaat cgttcagttc ctgtaaccat taattgagcg cctaaactgc gcaccttgac 840
gctgttagat gctgcagtaa ggaactcgga gtcaagtgtg ggggacaggt tggtcaataa 900

```
atgacgacat tccggacggc tgtgcttggt gcccacgggg acccgcgagg gggcccaggg    960

aggaggcggg aaaggggcag gttcaccggc ccgctgggtc tccagcacat tccagaagtc   1020

taagccagtc catctatcct tccaaacgcc cccacctcgc ttccctccct ggagcccgca   1080

tcccacggtg caatttcagt gactttatgc ggagaaactt gatcctatct cactctcccc   1140

aaacttccta actgccttgg gtttgtcacc tggccgtgtg gggagccacc gagcgccccc   1200

tgtggccccc acccgagctc ggcgggggga gcggcgcgcg ggtgctgggg gaccgacccc   1260

tcccgcgaag gcgtcggcgc ggggctggcg tagggcctgc gtcagctgca gcccgccggc   1320

gattggggcg cgcgcgcctc cttcggtttg gggctaatta taaagtggct ccagcagccg   1380

ttaagccccg ggacggcgag gcaggcgctc agagccccgc agcctggccc gtgaccccgc   1440

agagacgctg aggaccgcga cggtgaggcc ctacgtccgc cagcacaccc gggcccgctt   1500

ctccccgacg cccgccctcc tcacacttgc cttcttctct tccctctaga gtcgtgtctg   1560

aacccggctt ttccaattgg cctgctccat ccgaacagcg tcaacgtgag tgaatttgcc   1620

cgaagcttgt ctttgctgag cgggtttggg gacgtctgcc cgccctcttt cccttcacat   1680

ttcattgcat gggttcccca acagcgttcc ctggttcttc tttgtgaccc cagtcaatgt   1740

cctgcctccc ccggctcccg ctctctcgcc cctggtctgc ggcgttctct ccggaatctt   1800

gccctgggcc gcggacgccc aggaaaagag ccgggtgccc caggcagcct cgcgttgggg   1860

gcgaccgcgc catcccggga accgcgaggc gatctgagtc gcctccacgt ctacctaaaa   1920

gctgtcggcc gggagggcgg ggccccagaa aggagcattc ctgcgggctt ttgctcgacg   1980

atcccctgct gaggctgtcg                                               2000
```

```
<210> SEQ ID NO 38
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 38

gtatacttca gagagaagac tgaaacttct agagactgtt tctagcatcc ttaagtaact     60

gcagacactt ataatactga atgatatcct agttataaat aattcttatc cataacttaa    120

atccatcttg aggctctact aagtaaatct tccttaacct acttagagga tgtgcagtag    180

cgatgaaagt agcctttctt ttcttttttt tttttttttt ttttgagacg gagtctcgct    240

ctgtcgccag gctggagtac agtggcgcga tctcggctca ctgtaacctc ctccgcctcc    300

tgggttccag cgattctcct gcctcagcct cccgagtagc tgggactaca ggcgtgcgcc    360

accactccca cataattttt tgtattttta gtagagacgg ggtttcaccg tgttggccag    420

gatggtctca aatctcttga cctcgtgatc tgtgtgctgg gagtacaggc gtgagccacc    480

gcgcccggcc ttaagcccct ttctttaagg ctcaagggca tattttcaca ctgcagtgca    540

tcacaaccgt tttcattctt ccagtgttcc tttcttctgg tctccagcca cctgccaggt    600

acttctgatt aattacatat aagatttatc caagccaccc cctccgtttc taccaactgg    660

acttcattct cttcagttcc tgctagaatg cacctcctac ctgaagtctt ccctcatcaa    720

tgccctccat gatcagcctt tgactctgga atcccttaat atattcctca gatcattaga    780

ggttttctga gtcatcatct gagatttttc attaaattgt ggagtttgag cagccagtcc    840

tgagctgtcg gactcagttc caaatagaag tcctagttaa agacacaaaa acaagaagat    900
```

```
gggttagctg cggctcgaag agctggtgag cgcgaccaca gggcagcttg cggacggttc     960

tttcggacag gacaagggcg agggaaacgg cagaatggtg acgcacctga gtgcgcccac    1020

tagacgaaag aagaccaact aagccttcgt gtagtgcgta gacaggccga cacacacaca    1080

cacacacaca cacacacact aacacacacg caaagacagt gagggagcga gaggcgcatc    1140

cccaggtagc tgacaatgac acggccccga tccggacgcg ggcttaaagc cccccgactt    1200

ccggagtgcc cccctccccg gcgacctccg gagattaccg ctggcgcatc tctccgccct    1260

gcccggctcc ggcgccctcc cctccccccg cagccgcagc tccccgcccc ccgcgaacgc    1320

ggctccccag tgtcctccag aacgcccgcg tggctgtcgg gtttcgaacc ccagggccga    1380

ctctagtact cggcgcgcgc gccgccgcgt cgccgaccag cctgcggccc ccgcatcaat    1440

cattaacggg gcggcccggg ctgcggcggc ccgaggaggg ggatggtacg gaactcgaga    1500

caggggacaa ctctatcccc cgaagcggcc gcgaaaccct agcctgggag gcccccgccc    1560

ttcctcggtg cgcccgtccc tccctccgcg cctcggctcg cacatcccca cctcccgctc    1620

cgggggcggc ggcggcggag gcacccgcac cgcgcgatgc ccagtcaccg ctgccgcgct    1680

gccgccgcag tcagccgcgc cgccgccgct gccgcagcgc gggcggccgc gcgccggtag    1740

caggggcttg gcgaggaagc cgctgagcct cgcgcgctcc gcgctcctgg cggtcgcagc    1800

gctgcctatt aattgattct cttattgatt tatttaattt ttaggagcgg ctgctcggag    1860

gcacgggtct tctcctaaac ctgcagcgac gcccccggcg tgggcacaaa ggctccgacg    1920

gcggccggcg ggggctgccc agcgcccggg agccggcgcc agaggtcgcc tgcgcgcgcc    1980

ctagccgagc cccgggcacc                                                2000


<210> SEQ ID NO 39
<211> LENGTH: 1000
<212> TYPE: DNA
<213> ORGANISM: Artificial Sequence
<220> FEATURE:
<223> OTHER INFORMATION: Synthetic Construct

<400> SEQUENCE: 39

ttcatcttaa agaatctgag ttgaatagag agggaaatga ggggcgggtg ttcgctccaa      60

cgaaatcgct tggaggatca tggggcgtgt gtccctgtgt gcggaactgg gaggaaaacg     120

cagcccccag tttggtaaat ggtgaagcag cggtaggccg gtcggtggcg cggatttaag     180

atttgctgaa ggcactacca cagatgtagc tctctggaac ttccatccct cctctcctac     240

caccccccaa aaaaagacaa aaccgagttc agaccggctc ccccaacacc aagccgcttc     300

tatttatcaa gtgggtcaac ttccactcgg aagcacctcg cggggctcgg ctccagggca     360

cctggtggct ggggagctgt attgttttcc tgggcacgga ggttcggcgc cggttttagg     420

attgtgcaaa aagagagtag aaggtacaga gatttatttc tgctttttgc tgttcagccg     480

ccgtttgccc cagcgaggtg ggctggaggc tgaatttcaa gccttgttta acctctacaa     540

gagacaccct ccattcagcc atctcacttt ctctctggcc tccctctctc tttttttcct     600

ttccgttctc tccgtccttt ctctctatct ctgtctctgt gtgtgtcgtg tttgttcccg     660

tgccctcctc tccgaccttg gccggggctc ctagtcctga gagaaacggc gttcggtgcg     720

ccggcggtgg ctatgcggct ggctctttcg gggctcccgg gactaggttg gggaaagagg     780

gcatctcccc ggcctctcgg ggcccagccc agtcttccta gatctggcgt ccgcccttcc     840

ctcccctccc gcactggcag gagagaaatg gccgcagtgt gggccgcggg gcagctagga     900

ctggaaagcg gggaccctgg agggtgcgat cgcggacggg gtgtgcgggc gcgggtcgtg     960
```

tgcgtgtgcg tgcagggttc cgaccacggg gacacgagct 1000

<210> SEQ ID NO 40
<211> LENGTH: 1000
<212> TYPE: DNA
<213> ORGANISM: Artificial Sequence
<220> FEATURE:
<223> OTHER INFORMATION: Synthetic Construct

<400> SEQUENCE: 40
gtggagggcg ttggaccttc ttccgcaatc gggaccactc caggtctccc cggagaaggc 60
tgagtctcca gcgcgtggat tcagatcagg actctgtcta agtaggcgag agctggggat 120
accgctgggg gctttggcga agctaagaaa gcactggctt cttattctca ccagacatct 180
caacacccac gtgcgctggg tcccgcagtc tctcgcccgc cccacgcggg tcccagccct 240
ggtccttact ccccgcgcgg gaagaatctg gggagggtgg gggcggagag gcggctgatc 300
ggagagtggg agggaggatg ggagatgggc agaggctgcc cgcatcaggg ccaggacaga 360
cgtccgcgcg gccccaggca ctcacttgag tgtcacgcaa gtcaccccaa caccgcacaa 420
gacagtggcg gggtgcgcac cgaggcccct acctgggggg tgtgcgcgca ctgaacgacc 480
ccttctccag gtgcgcgagc cgctccggcg gccgtgcaca ctgcgccccc ttccgcccac 540
ctgcctggcc tgcgtttcta accacgcggg cggtcccgag acttcgcgca aaaggcagga 600
ccgcgactcc caataatgat atcttcgaaa taacccccctg ctgagccggc gcccagggcc 660
gggggtagag tcccgagtcc cttttgcgga attaaggaga cctctggcga ccggggagcc 720
tgcccctgtg accgctccag cagcccctgc cgcgtgcgtg cccgagtgtg gcccgcagct 780
cccaaagccc aggtgtgtgt ggcctagggc ggggagagtt ggcgacccgg gcccatcacc 840
gccccagtgc caccgcccca gtgcctgacc agatggggtg cggtccctac gcccggcgtg 900
gccccgccgc cgctcagatc tgaagtccgg ctttcgctcg ccctgcgcgg cggaacctct 960
gacccggagc agctctaggc cgtgggcttc gtctcctcct 1000

<210> SEQ ID NO 41
<211> LENGTH: 30
<212> TYPE: DNA
<213> ORGANISM: Artificial Sequence
<220> FEATURE:
<223> OTHER INFORMATION: Synthetic Construct

<400> SEQUENCE: 41
ttcttattct caccagacat ctcaacaccc 30

<210> SEQ ID NO 42
<211> LENGTH: 25
<212> TYPE: DNA
<213> ORGANISM: Artificial Sequence
<220> FEATURE:
<223> OTHER INFORMATION: Synthetic Construct

<400> SEQUENCE: 42
atctcccatc ctccctccca ctctc 25

<210> SEQ ID NO 43
<211> LENGTH: 14
<212> TYPE: DNA
<213> ORGANISM: Artificial Sequence
<220> FEATURE:
<223> OTHER INFORMATION: Synthetic Construct

<400> SEQUENCE: 43
ttgcgttttt tttc 14

<210> SEQ ID NO 44
<211> LENGTH: 14
<212> TYPE: DNA
<213> ORGANISM: Artificial Sequence
<220> FEATURE:
<223> OTHER INFORMATION: Synthetic Construct

<400> SEQUENCE: 44
ttattaaaaa tcgc 14

<210> SEQ ID NO 45
<211> LENGTH: 24
<212> TYPE: DNA
<213> ORGANISM: Artificial Sequence
<220> FEATURE:
<223> OTHER INFORMATION: Synthetic Construct

<400> SEQUENCE: 45
agatttcgcg taaaaggtag gatc 24

<210> SEQ ID NO 46
<211> LENGTH: 14
<212> TYPE: DNA
<213> ORGANISM: Artificial Sequence
<220> FEATURE:
<223> OTHER INFORMATION: Synthetic Construct

<400> SEQUENCE: 46
tgcgtttttt ttcg 14

<210> SEQ ID NO 47
<211> LENGTH: 14
<212> TYPE: DNA
<213> ORGANISM: Artificial Sequence
<220> FEATURE:
<223> OTHER INFORMATION: Synthetic Construct

<400> SEQUENCE: 47
gcgttttttt tcgt 14

<210> SEQ ID NO 48
<211> LENGTH: 14
<212> TYPE: DNA
<213> ORGANISM: Artificial Sequence
<220> FEATURE:
<223> OTHER INFORMATION: Synthetic Construct

<400> SEQUENCE: 48
cgtttttttt cgtt 14

<210> SEQ ID NO 49
<211> LENGTH: 14
<212> TYPE: DNA
<213> ORGANISM: Artificial Sequence
<220> FEATURE:
<223> OTHER INFORMATION: Synthetic Construct

<400> SEQUENCE: 49
gttttttttc gttt 14

<210> SEQ ID NO 50
<211> LENGTH: 14

<212> TYPE: DNA
<213> ORGANISM: Artificial Sequence
<220> FEATURE:
<223> OTHER INFORMATION: Synthetic Construct

<400> SEQUENCE: 50
ttttttttcg ttta 14

<210> SEQ ID NO 51
<211> LENGTH: 14
<212> TYPE: DNA
<213> ORGANISM: Artificial Sequence
<220> FEATURE:
<223> OTHER INFORMATION: Synthetic Construct

<400> SEQUENCE: 51
tttttttcgt ttat 14

<210> SEQ ID NO 52
<211> LENGTH: 14
<212> TYPE: DNA
<213> ORGANISM: Artificial Sequence
<220> FEATURE:
<223> OTHER INFORMATION: Synthetic Construct

<400> SEQUENCE: 52
ttttttcgtt tatt 14

<210> SEQ ID NO 53
<211> LENGTH: 14
<212> TYPE: DNA
<213> ORGANISM: Artificial Sequence
<220> FEATURE:
<223> OTHER INFORMATION: Synthetic Construct

<400> SEQUENCE: 53
tttttcgttt attt 14

<210> SEQ ID NO 54
<211> LENGTH: 14
<212> TYPE: DNA
<213> ORGANISM: Artificial Sequence
<220> FEATURE:
<223> OTHER INFORMATION: Synthetic Construct

<400> SEQUENCE: 54
ttttcgttta tttg 14

<210> SEQ ID NO 55
<211> LENGTH: 14
<212> TYPE: DNA
<213> ORGANISM: Artificial Sequence
<220> FEATURE:
<223> OTHER INFORMATION: Synthetic Construct

<400> SEQUENCE: 55
tttcgtttat ttgt 14

<210> SEQ ID NO 56
<211> LENGTH: 14
<212> TYPE: DNA
<213> ORGANISM: Artificial Sequence
<220> FEATURE:
<223> OTHER INFORMATION: Synthetic Construct

<400> SEQUENCE: 56
ttcgtttatt tgtt 14

<210> SEQ ID NO 57
<211> LENGTH: 14
<212> TYPE: DNA
<213> ORGANISM: Artificial Sequence
<220> FEATURE:
<223> OTHER INFORMATION: Synthetic Construct

<400> SEQUENCE: 57
tcgtttattt gttt 14

<210> SEQ ID NO 58
<211> LENGTH: 14
<212> TYPE: DNA
<213> ORGANISM: Artificial Sequence
<220> FEATURE:
<223> OTHER INFORMATION: Synthetic Construct

<400> SEQUENCE: 58
cgtttatttg tttg 14

<210> SEQ ID NO 59
<211> LENGTH: 14
<212> TYPE: DNA
<213> ORGANISM: Artificial Sequence
<220> FEATURE:
<223> OTHER INFORMATION: Synthetic Construct

<400> SEQUENCE: 59
gtttatttgt ttgg 14

<210> SEQ ID NO 60
<211> LENGTH: 14
<212> TYPE: DNA
<213> ORGANISM: Artificial Sequence
<220> FEATURE:
<223> OTHER INFORMATION: Synthetic Construct

<400> SEQUENCE: 60
tttatttgtt tggt 14

<210> SEQ ID NO 61
<211> LENGTH: 14
<212> TYPE: DNA
<213> ORGANISM: Artificial Sequence
<220> FEATURE:
<223> OTHER INFORMATION: Synthetic Construct

<400> SEQUENCE: 61
ttatttgttt ggtt 14

<210> SEQ ID NO 62
<211> LENGTH: 14
<212> TYPE: DNA
<213> ORGANISM: Artificial Sequence
<220> FEATURE:
<223> OTHER INFORMATION: Synthetic Construct

<400> SEQUENCE: 62
tatttgtttg gttt 14

<210> SEQ ID NO 63
<211> LENGTH: 14
<212> TYPE: DNA
<213> ORGANISM: Artificial Sequence -continued
<220> FEATURE:
<223> OTHER INFORMATION: Synthetic Construct

<400> SEQUENCE: 63
ctcgaaactc tacc 14

<210> SEQ ID NO 64
<211> LENGTH: 24
<212> TYPE: DNA
<213> ORGANISM: Artificial Sequence
<220> FEATURE:
<223> OTHER INFORMATION: Synthetic Construct

<400> SEQUENCE: 64
gttgagtcgg cgtttagggt cggg 24

<210> SEQ ID NO 65
<211> LENGTH: 14
<212> TYPE: DNA
<213> ORGANISM: Artificial Sequence
<220> FEATURE:
<223> OTHER INFORMATION: Synthetic Construct

<400> SEQUENCE: 65
atttgtttgg tttg 14

<210> SEQ ID NO 66
<211> LENGTH: 14
<212> TYPE: DNA
<213> ORGANISM: Artificial Sequence
<220> FEATURE:
<223> OTHER INFORMATION: Synthetic Construct

<400> SEQUENCE: 66
tttgtttggt ttgc 14

<210> SEQ ID NO 67
<211> LENGTH: 14
<212> TYPE: DNA
<213> ORGANISM: Artificial Sequence
<220> FEATURE:
<223> OTHER INFORMATION: Synthetic Construct

<400> SEQUENCE: 67
ttgtttggtt tgcg 14

<210> SEQ ID NO 68
<211> LENGTH: 14
<212> TYPE: DNA
<213> ORGANISM: Artificial Sequence
<220> FEATURE:
<223> OTHER INFORMATION: Synthetic Construct

<400> SEQUENCE: 68
tgtttggttt gcgt 14

<210> SEQ ID NO 69
<211> LENGTH: 14
<212> TYPE: DNA
<213> ORGANISM: Artificial Sequence
<220> FEATURE:
<223> OTHER INFORMATION: Synthetic Construct

<400> SEQUENCE: 69
gtttggtttg cgtt 14

<210> SEQ ID NO 70
<211> LENGTH: 14
<212> TYPE: DNA
<213> ORGANISM: Artificial Sequence
<220> FEATURE:
<223> OTHER INFORMATION: Synthetic Construct

<400> SEQUENCE: 70
tttggtttgc gttt 14

<210> SEQ ID NO 71
<211> LENGTH: 14
<212> TYPE: DNA
<213> ORGANISM: Artificial Sequence
<220> FEATURE:
<223> OTHER INFORMATION: Synthetic Construct

<400> SEQUENCE: 71
ttggtttgcg tttt 14

<210> SEQ ID NO 72
<211> LENGTH: 14
<212> TYPE: DNA
<213> ORGANISM: Artificial Sequence
<220> FEATURE:
<223> OTHER INFORMATION: Synthetic Construct

<400> SEQUENCE: 72
tggtttgcgt tttt 14

<210> SEQ ID NO 73
<211> LENGTH: 14
<212> TYPE: DNA
<213> ORGANISM: Artificial Sequence
<220> FEATURE:
<223> OTHER INFORMATION: Synthetic Construct

<400> SEQUENCE: 73
ggtttgcgtt ttta 14

<210> SEQ ID NO 74
<211> LENGTH: 14
<212> TYPE: DNA
<213> ORGANISM: Artificial Sequence
<220> FEATURE:
<223> OTHER INFORMATION: Synthetic Construct

<400> SEQUENCE: 74
gtttgcgttt ttaa 14

<210> SEQ ID NO 75
<211> LENGTH: 14
<212> TYPE: DNA
<213> ORGANISM: Artificial Sequence
<220> FEATURE:
<223> OTHER INFORMATION: Synthetic Construct

<400> SEQUENCE: 75
tttgcgtttt taat 14

<210> SEQ ID NO 76
<211> LENGTH: 14
<212> TYPE: DNA
<213> ORGANISM: Artificial Sequence
<220> FEATURE:
<223> OTHER INFORMATION: Synthetic Construct

<400> SEQUENCE: 76
ttgcgttttt aatt 14

<210> SEQ ID NO 77
<211> LENGTH: 14
<212> TYPE: DNA
<213> ORGANISM: Artificial Sequence
<220> FEATURE:
<223> OTHER INFORMATION: Synthetic Construct

<400> SEQUENCE: 77
tgcgttttta atta 14

<210> SEQ ID NO 78
<211> LENGTH: 14
<212> TYPE: DNA
<213> ORGANISM: Artificial Sequence
<220> FEATURE:
<223> OTHER INFORMATION: Synthetic Construct

<400> SEQUENCE: 78
gcgtttttaa ttac 14

<210> SEQ ID NO 79
<211> LENGTH: 14
<212> TYPE: DNA
<213> ORGANISM: Artificial Sequence
<220> FEATURE:
<223> OTHER INFORMATION: Synthetic Construct

<400> SEQUENCE: 79
cgtttttaat tacg 14

<210> SEQ ID NO 80
<211> LENGTH: 14
<212> TYPE: DNA
<213> ORGANISM: Artificial Sequence
<220> FEATURE:
<223> OTHER INFORMATION: Synthetic Construct

<400> SEQUENCE: 80
gtttttaatt acgc 14

<210> SEQ ID NO 81
<211> LENGTH: 14
<212> TYPE: DNA
<213> ORGANISM: Artificial Sequence
<220> FEATURE:
<223> OTHER INFORMATION: Synthetic Construct

<400> SEQUENCE: 81
tttttaatta cgcg 14

<210> SEQ ID NO 82
<211> LENGTH: 14
<212> TYPE: DNA
<213> ORGANISM: Artificial Sequence
<220> FEATURE:
<223> OTHER INFORMATION: Synthetic Construct

<400> SEQUENCE: 82
ttttaattac gcgg 14

<210> SEQ ID NO 83

<211> LENGTH: 14
<212> TYPE: DNA
<213> ORGANISM: Artificial Sequence
<220> FEATURE:
<223> OTHER INFORMATION: Synthetic Construct

<400> SEQUENCE: 83
tttaattacg cggg 14

<210> SEQ ID NO 84
<211> LENGTH: 14
<212> TYPE: DNA
<213> ORGANISM: Artificial Sequence
<220> FEATURE:
<223> OTHER INFORMATION: Synthetic Construct

<400> SEQUENCE: 84
ttaattacgc gggc 14

<210> SEQ ID NO 85
<211> LENGTH: 14
<212> TYPE: DNA
<213> ORGANISM: Artificial Sequence
<220> FEATURE:
<223> OTHER INFORMATION: Synthetic Construct

<400> SEQUENCE: 85
taattacgcg ggcg 14

<210> SEQ ID NO 86
<211> LENGTH: 14
<212> TYPE: DNA
<213> ORGANISM: Artificial Sequence
<220> FEATURE:
<223> OTHER INFORMATION: Synthetic Construct

<400> SEQUENCE: 86
aattacgcgg gcgg 14

<210> SEQ ID NO 87
<211> LENGTH: 14
<212> TYPE: DNA
<213> ORGANISM: Artificial Sequence
<220> FEATURE:
<223> OTHER INFORMATION: Synthetic Construct

<400> SEQUENCE: 87
attacgcggg cggt 14

<210> SEQ ID NO 88
<211> LENGTH: 14
<212> TYPE: DNA
<213> ORGANISM: Artificial Sequence
<220> FEATURE:
<223> OTHER INFORMATION: Synthetic Construct

<400> SEQUENCE: 88
ttacgcgggc ggtt 14

<210> SEQ ID NO 89
<211> LENGTH: 14
<212> TYPE: DNA
<213> ORGANISM: Artificial Sequence
<220> FEATURE:
<223> OTHER INFORMATION: Synthetic Construct

<400> SEQUENCE: 89
tacgcgggcg gttt 14

<210> SEQ ID NO 90
<211> LENGTH: 14
<212> TYPE: DNA
<213> ORGANISM: Artificial Sequence
<220> FEATURE:
<223> OTHER INFORMATION: Synthetic Construct

<400> SEQUENCE: 90
acgcgggcgg tttc 14

<210> SEQ ID NO 91
<211> LENGTH: 14
<212> TYPE: DNA
<213> ORGANISM: Artificial Sequence
<220> FEATURE:
<223> OTHER INFORMATION: Synthetic Construct

<400> SEQUENCE: 91
cgcgggcggt ttcg 14

<210> SEQ ID NO 92
<211> LENGTH: 14
<212> TYPE: DNA
<213> ORGANISM: Artificial Sequence
<220> FEATURE:
<223> OTHER INFORMATION: Synthetic Construct

<400> SEQUENCE: 92
gcgggcggtt tcga 14

<210> SEQ ID NO 93
<211> LENGTH: 14
<212> TYPE: DNA
<213> ORGANISM: Artificial Sequence
<220> FEATURE:
<223> OTHER INFORMATION: Synthetic Construct

<400> SEQUENCE: 93
cgggcggttt cgag 14

<210> SEQ ID NO 94
<211> LENGTH: 14
<212> TYPE: DNA
<213> ORGANISM: Artificial Sequence
<220> FEATURE:
<223> OTHER INFORMATION: Synthetic Construct

<400> SEQUENCE: 94
gggcggtttc gaga 14

<210> SEQ ID NO 95
<211> LENGTH: 14
<212> TYPE: DNA
<213> ORGANISM: Artificial Sequence
<220> FEATURE:
<223> OTHER INFORMATION: Synthetic Construct

<400> SEQUENCE: 95
ggcggtttcg agat 14

<210> SEQ ID NO 96
<211> LENGTH: 14
<212> TYPE: DNA

<213> ORGANISM: Artificial Sequence
<220> FEATURE:
<223> OTHER INFORMATION: Synthetic Construct

<400> SEQUENCE: 96
gcggtttcga gatt 14

<210> SEQ ID NO 97
<211> LENGTH: 14
<212> TYPE: DNA
<213> ORGANISM: Artificial Sequence
<220> FEATURE:
<223> OTHER INFORMATION: Synthetic Construct

<400> SEQUENCE: 97
cggtttcgag attt 14

<210> SEQ ID NO 98
<211> LENGTH: 14
<212> TYPE: DNA
<213> ORGANISM: Artificial Sequence
<220> FEATURE:
<223> OTHER INFORMATION: Synthetic Construct

<400> SEQUENCE: 98
ggtttcgaga tttc 14

<210> SEQ ID NO 99
<211> LENGTH: 14
<212> TYPE: DNA
<213> ORGANISM: Artificial Sequence
<220> FEATURE:
<223> OTHER INFORMATION: Synthetic Construct

<400> SEQUENCE: 99
gtttcgagat ttcg 14

<210> SEQ ID NO 100
<211> LENGTH: 14
<212> TYPE: DNA
<213> ORGANISM: Artificial Sequence
<220> FEATURE:
<223> OTHER INFORMATION: Synthetic Construct

<400> SEQUENCE: 100
tttcgagatt tcgc 14

<210> SEQ ID NO 101
<211> LENGTH: 14
<212> TYPE: DNA
<213> ORGANISM: Artificial Sequence
<220> FEATURE:
<223> OTHER INFORMATION: Synthetic Construct

<400> SEQUENCE: 101
ttcgagattt cgcg 14

<210> SEQ ID NO 102
<211> LENGTH: 14
<212> TYPE: DNA
<213> ORGANISM: Artificial Sequence
<220> FEATURE:
<223> OTHER INFORMATION: Synthetic Construct

<400> SEQUENCE: 102
tcgagatttc gcgt 14

-continued

<210> SEQ ID NO 103
<211> LENGTH: 14
<212> TYPE: DNA
<213> ORGANISM: Artificial Sequence
<220> FEATURE:
<223> OTHER INFORMATION: Synthetic Construct

<400> SEQUENCE: 103
cgagatttcg cgta 14

<210> SEQ ID NO 104
<211> LENGTH: 14
<212> TYPE: DNA
<213> ORGANISM: Artificial Sequence
<220> FEATURE:
<223> OTHER INFORMATION: Synthetic Construct

<400> SEQUENCE: 104
gagatttcgc gtaa 14

<210> SEQ ID NO 105
<211> LENGTH: 14
<212> TYPE: DNA
<213> ORGANISM: Artificial Sequence
<220> FEATURE:
<223> OTHER INFORMATION: Synthetic Construct

<400> SEQUENCE: 105
agatttcgcg taaa 14

<210> SEQ ID NO 106
<211> LENGTH: 14
<212> TYPE: DNA
<213> ORGANISM: Artificial Sequence
<220> FEATURE:
<223> OTHER INFORMATION: Synthetic Construct

<400> SEQUENCE: 106
gatttcgcgt aaaa 14

<210> SEQ ID NO 107
<211> LENGTH: 14
<212> TYPE: DNA
<213> ORGANISM: Artificial Sequence
<220> FEATURE:
<223> OTHER INFORMATION: Synthetic Construct

<400> SEQUENCE: 107
atttcgcgta aaag 14

<210> SEQ ID NO 108
<211> LENGTH: 14
<212> TYPE: DNA
<213> ORGANISM: Artificial Sequence
<220> FEATURE:
<223> OTHER INFORMATION: Synthetic Construct

<400> SEQUENCE: 108
tttcgcgtaa aagg 14

<210> SEQ ID NO 109
<211> LENGTH: 14
<212> TYPE: DNA
<213> ORGANISM: Artificial Sequence
<220> FEATURE:

<223> OTHER INFORMATION: Synthetic Construct

<400> SEQUENCE: 109
ttcgcgtaaa aggt 14

<210> SEQ ID NO 110
<211> LENGTH: 14
<212> TYPE: DNA
<213> ORGANISM: Artificial Sequence
<220> FEATURE:
<223> OTHER INFORMATION: Synthetic Construct

<400> SEQUENCE: 110
tcgcgtaaaa ggta 14

<210> SEQ ID NO 111
<211> LENGTH: 14
<212> TYPE: DNA
<213> ORGANISM: Artificial Sequence
<220> FEATURE:
<223> OTHER INFORMATION: Synthetic Construct

<400> SEQUENCE: 111
cgcgtaaaag gtag 14

<210> SEQ ID NO 112
<211> LENGTH: 14
<212> TYPE: DNA
<213> ORGANISM: Artificial Sequence
<220> FEATURE:
<223> OTHER INFORMATION: Synthetic Construct

<400> SEQUENCE: 112
gcgtaaaagg tagg 14

<210> SEQ ID NO 113
<211> LENGTH: 14
<212> TYPE: DNA
<213> ORGANISM: Artificial Sequence
<220> FEATURE:
<223> OTHER INFORMATION: Synthetic Construct

<400> SEQUENCE: 113
cgtaaaaggt agga 14

<210> SEQ ID NO 114
<211> LENGTH: 14
<212> TYPE: DNA
<213> ORGANISM: Artificial Sequence
<220> FEATURE:
<223> OTHER INFORMATION: Synthetic Construct

<400> SEQUENCE: 114
gtaaaaggta ggat 14

<210> SEQ ID NO 115
<211> LENGTH: 14
<212> TYPE: DNA
<213> ORGANISM: Artificial Sequence
<220> FEATURE:
<223> OTHER INFORMATION: Synthetic Construct

<400> SEQUENCE: 115
taaaaggtag gatc 14

<210> SEQ ID NO 116
<211> LENGTH: 14
<212> TYPE: DNA
<213> ORGANISM: Artificial Sequence
<220> FEATURE:
<223> OTHER INFORMATION: Synthetic Construct

<400> SEQUENCE: 116
aaaaggtagg atcg 14

<210> SEQ ID NO 117
<211> LENGTH: 14
<212> TYPE: DNA
<213> ORGANISM: Artificial Sequence
<220> FEATURE:
<223> OTHER INFORMATION: Synthetic Construct

<400> SEQUENCE: 117
aaaggtagga tcgc 14

<210> SEQ ID NO 118
<211> LENGTH: 14
<212> TYPE: DNA
<213> ORGANISM: Artificial Sequence
<220> FEATURE:
<223> OTHER INFORMATION: Synthetic Construct

<400> SEQUENCE: 118
aaggtaggat cgcg 14

<210> SEQ ID NO 119
<211> LENGTH: 14
<212> TYPE: DNA
<213> ORGANISM: Artificial Sequence
<220> FEATURE:
<223> OTHER INFORMATION: Synthetic Construct

<400> SEQUENCE: 119
aggtaggatc gcga 14

<210> SEQ ID NO 120
<211> LENGTH: 14
<212> TYPE: DNA
<213> ORGANISM: Artificial Sequence
<220> FEATURE:
<223> OTHER INFORMATION: Synthetic Construct

<400> SEQUENCE: 120
ggtaggatcg cgat 14

<210> SEQ ID NO 121
<211> LENGTH: 14
<212> TYPE: DNA
<213> ORGANISM: Artificial Sequence
<220> FEATURE:
<223> OTHER INFORMATION: Synthetic Construct

<400> SEQUENCE: 121
gtaggatcgc gatt 14

<210> SEQ ID NO 122
<211> LENGTH: 14
<212> TYPE: DNA
<213> ORGANISM: Artificial Sequence
<220> FEATURE:
<223> OTHER INFORMATION: Synthetic Construct

<400> SEQUENCE: 122
taggatcgcg attt 14

<210> SEQ ID NO 123
<211> LENGTH: 14
<212> TYPE: DNA
<213> ORGANISM: Artificial Sequence
<220> FEATURE:
<223> OTHER INFORMATION: Synthetic Construct

<400> SEQUENCE: 123
aggatcgcga tttt 14

<210> SEQ ID NO 124
<211> LENGTH: 14
<212> TYPE: DNA
<213> ORGANISM: Artificial Sequence
<220> FEATURE:
<223> OTHER INFORMATION: Synthetic Construct

<400> SEQUENCE: 124
ggatcgcgat tttt 14

<210> SEQ ID NO 125
<211> LENGTH: 14
<212> TYPE: DNA
<213> ORGANISM: Artificial Sequence
<220> FEATURE:
<223> OTHER INFORMATION: Synthetic Construct

<400> SEQUENCE: 125
gatcgcgatt ttta 14

<210> SEQ ID NO 126
<211> LENGTH: 14
<212> TYPE: DNA
<213> ORGANISM: Artificial Sequence
<220> FEATURE:
<223> OTHER INFORMATION: Synthetic Construct

<400> SEQUENCE: 126
aaaacgatca caaa 14

<210> SEQ ID NO 127
<211> LENGTH: 26
<212> TYPE: DNA
<213> ORGANISM: Artificial Sequence
<220> FEATURE:
<223> OTHER INFORMATION: Synthetic Construct

<400> SEQUENCE: 127
gatttttggc gatcggggag tttgtt 26

<210> SEQ ID NO 128
<211> LENGTH: 14
<212> TYPE: DNA
<213> ORGANISM: Artificial Sequence
<220> FEATURE:
<223> OTHER INFORMATION: Synthetic Construct

<400> SEQUENCE: 128
atcgcgattt ttaa 14

<210> SEQ ID NO 129
<211> LENGTH: 14

<212> TYPE: DNA
<213> ORGANISM: Artificial Sequence
<220> FEATURE:
<223> OTHER INFORMATION: Synthetic Construct

<400> SEQUENCE: 129
tcgcgatttt taat 14

<210> SEQ ID NO 130
<211> LENGTH: 14
<212> TYPE: DNA
<213> ORGANISM: Artificial Sequence
<220> FEATURE:
<223> OTHER INFORMATION: Synthetic Construct

<400> SEQUENCE: 130
cgcgattttt aata 14

<210> SEQ ID NO 131
<211> LENGTH: 14
<212> TYPE: DNA
<213> ORGANISM: Artificial Sequence
<220> FEATURE:
<223> OTHER INFORMATION: Synthetic Construct

<400> SEQUENCE: 131
gcgattttta ataa 14

<210> SEQ ID NO 132
<211> LENGTH: 14
<212> TYPE: DNA
<213> ORGANISM: Artificial Sequence
<220> FEATURE:
<223> OTHER INFORMATION: Synthetic Construct

<400> SEQUENCE: 132
cgatttttaa taat 14

<210> SEQ ID NO 133
<211> LENGTH: 14
<212> TYPE: DNA
<213> ORGANISM: Artificial Sequence
<220> FEATURE:
<223> OTHER INFORMATION: Synthetic Construct

<400> SEQUENCE: 133
gatttttaat aatg 14

<210> SEQ ID NO 134
<211> LENGTH: 14
<212> TYPE: DNA
<213> ORGANISM: Artificial Sequence
<220> FEATURE:
<223> OTHER INFORMATION: Synthetic Construct

<400> SEQUENCE: 134
atttttaata atga 14

<210> SEQ ID NO 135
<211> LENGTH: 14
<212> TYPE: DNA
<213> ORGANISM: Artificial Sequence
<220> FEATURE:
<223> OTHER INFORMATION: Synthetic Construct

<400> SEQUENCE: 135
tttttaataa tgat 14

<210> SEQ ID NO 136
<211> LENGTH: 14
<212> TYPE: DNA
<213> ORGANISM: Artificial Sequence
<220> FEATURE:
<223> OTHER INFORMATION: Synthetic Construct

<400> SEQUENCE: 136
ttttaataat gata 14

<210> SEQ ID NO 137
<211> LENGTH: 14
<212> TYPE: DNA
<213> ORGANISM: Artificial Sequence
<220> FEATURE:
<223> OTHER INFORMATION: Synthetic Construct

<400> SEQUENCE: 137
tttaataatg atat 14

<210> SEQ ID NO 138
<211> LENGTH: 14
<212> TYPE: DNA
<213> ORGANISM: Artificial Sequence
<220> FEATURE:
<223> OTHER INFORMATION: Synthetic Construct

<400> SEQUENCE: 138
ttaataatga tatt 14

<210> SEQ ID NO 139
<211> LENGTH: 14
<212> TYPE: DNA
<213> ORGANISM: Artificial Sequence
<220> FEATURE:
<223> OTHER INFORMATION: Synthetic Construct

<400> SEQUENCE: 139
taataatgat attt 14

<210> SEQ ID NO 140
<211> LENGTH: 14
<212> TYPE: DNA
<213> ORGANISM: Artificial Sequence
<220> FEATURE:
<223> OTHER INFORMATION: Synthetic Construct

<400> SEQUENCE: 140
aataatgata tttt 14

<210> SEQ ID NO 141
<211> LENGTH: 14
<212> TYPE: DNA
<213> ORGANISM: Artificial Sequence
<220> FEATURE:
<223> OTHER INFORMATION: Synthetic Construct

<400> SEQUENCE: 141
ataatgatat tttc 14

<210> SEQ ID NO 142
<211> LENGTH: 14
<212> TYPE: DNA
<213> ORGANISM: Artificial Sequence
<220> FEATURE:
<223> OTHER INFORMATION: Synthetic Construct

<400> SEQUENCE: 142
taatgatatt ttcg 14

<210> SEQ ID NO 143
<211> LENGTH: 14
<212> TYPE: DNA
<213> ORGANISM: Artificial Sequence
<220> FEATURE:
<223> OTHER INFORMATION: Synthetic Construct

<400> SEQUENCE: 143
aatgatattt tcga 14

<210> SEQ ID NO 144
<211> LENGTH: 14
<212> TYPE: DNA
<213> ORGANISM: Artificial Sequence
<220> FEATURE:
<223> OTHER INFORMATION: Synthetic Construct

<400> SEQUENCE: 144
atgatatttt cgaa 14

<210> SEQ ID NO 145
<211> LENGTH: 14
<212> TYPE: DNA
<213> ORGANISM: Artificial Sequence
<220> FEATURE:
<223> OTHER INFORMATION: Synthetic Construct

<400> SEQUENCE: 145
tgatattttc gaaa 14

<210> SEQ ID NO 146
<211> LENGTH: 14
<212> TYPE: DNA
<213> ORGANISM: Artificial Sequence
<220> FEATURE:
<223> OTHER INFORMATION: Synthetic Construct

<400> SEQUENCE: 146
gatattttcg aaat 14

<210> SEQ ID NO 147
<211> LENGTH: 14
<212> TYPE: DNA
<213> ORGANISM: Artificial Sequence
<220> FEATURE:
<223> OTHER INFORMATION: Synthetic Construct

<400> SEQUENCE: 147
atattttcga aata 14

<210> SEQ ID NO 148
<211> LENGTH: 14
<212> TYPE: DNA
<213> ORGANISM: Artificial Sequence
<220> FEATURE:
<223> OTHER INFORMATION: Synthetic Construct

<400> SEQUENCE: 148
tattttcgaa ataa 14

```
<210> SEQ ID NO 149
<211> LENGTH: 14
<212> TYPE: DNA
<213> ORGANISM: Artificial Sequence
<220> FEATURE:
<223> OTHER INFORMATION: Synthetic Construct

<400> SEQUENCE: 149

attttcgaaa taat                                                         14

<210> SEQ ID NO 150
<211> LENGTH: 14
<212> TYPE: DNA
<213> ORGANISM: Artificial Sequence
<220> FEATURE:
<223> OTHER INFORMATION: Synthetic Construct

<400> SEQUENCE: 150

ttttcgaaat aatt                                                         14

<210> SEQ ID NO 151
<211> LENGTH: 14
<212> TYPE: DNA
<213> ORGANISM: Artificial Sequence
<220> FEATURE:
<223> OTHER INFORMATION: Synthetic Construct

<400> SEQUENCE: 151

tttcgaaata attt                                                         14

<210> SEQ ID NO 152
<211> LENGTH: 14
<212> TYPE: DNA
<213> ORGANISM: Artificial Sequence
<220> FEATURE:
<223> OTHER INFORMATION: Synthetic Construct

<400> SEQUENCE: 152

ttcgaaataa tttt                                                         14

<210> SEQ ID NO 153
<211> LENGTH: 14
<212> TYPE: DNA
<213> ORGANISM: Artificial Sequence
<220> FEATURE:
<223> OTHER INFORMATION: Synthetic Construct

<400> SEQUENCE: 153

tcgaaataat tttt                                                         14

<210> SEQ ID NO 154
<211> LENGTH: 14
<212> TYPE: DNA
<213> ORGANISM: Artificial Sequence
<220> FEATURE:
<223> OTHER INFORMATION: Synthetic Construct

<400> SEQUENCE: 154

cgaaataatt tttt                                                         14

<210> SEQ ID NO 155
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 155
gaaataattt tttg 14

<210> SEQ ID NO 156
<211> LENGTH: 14
<212> TYPE: DNA
<213> ORGANISM: Artificial Sequence
<220> FEATURE:
<223> OTHER INFORMATION: Synthetic Construct

<400> SEQUENCE: 156
aaataatttt ttgt 14

<210> SEQ ID NO 157
<211> LENGTH: 14
<212> TYPE: DNA
<213> ORGANISM: Artificial Sequence
<220> FEATURE:
<223> OTHER INFORMATION: Synthetic Construct

<400> SEQUENCE: 157
aataattttt tgtt 14

<210> SEQ ID NO 158
<211> LENGTH: 14
<212> TYPE: DNA
<213> ORGANISM: Artificial Sequence
<220> FEATURE:
<223> OTHER INFORMATION: Synthetic Construct

<400> SEQUENCE: 158
ataatttttt gttg 14

<210> SEQ ID NO 159
<211> LENGTH: 14
<212> TYPE: DNA
<213> ORGANISM: Artificial Sequence
<220> FEATURE:
<223> OTHER INFORMATION: Synthetic Construct

<400> SEQUENCE: 159
taattttttg ttga 14

<210> SEQ ID NO 160
<211> LENGTH: 14
<212> TYPE: DNA
<213> ORGANISM: Artificial Sequence
<220> FEATURE:
<223> OTHER INFORMATION: Synthetic Construct

<400> SEQUENCE: 160
aattttttgt tgag 14

<210> SEQ ID NO 161
<211> LENGTH: 14
<212> TYPE: DNA
<213> ORGANISM: Artificial Sequence
<220> FEATURE:
<223> OTHER INFORMATION: Synthetic Construct

<400> SEQUENCE: 161 atttttgtt gagt 14

<210> SEQ ID NO 162

<211> LENGTH: 14
<212> TYPE: DNA
<213> ORGANISM: Artificial Sequence
<220> FEATURE:
<223> OTHER INFORMATION: Synthetic Construct

<400> SEQUENCE: 162 tttttgttg agtc 14

<210> SEQ ID NO 163
<211> LENGTH: 14
<212> TYPE: DNA
<213> ORGANISM: Artificial Sequence
<220> FEATURE:
<223> OTHER INFORMATION: Synthetic Construct

<400> SEQUENCE: 163
tttttgttga gtcg 14

<210> SEQ ID NO 164
<211> LENGTH: 14
<212> TYPE: DNA
<213> ORGANISM: Artificial Sequence
<220> FEATURE:
<223> OTHER INFORMATION: Synthetic Construct

<400> SEQUENCE: 164
ttttgttgag tcgg 14

<210> SEQ ID NO 165
<211> LENGTH: 14
<212> TYPE: DNA
<213> ORGANISM: Artificial Sequence
<220> FEATURE:
<223> OTHER INFORMATION: Synthetic Construct

<400> SEQUENCE: 165
tttgttgagt cggc 14

<210> SEQ ID NO 166
<211> LENGTH: 14
<212> TYPE: DNA
<213> ORGANISM: Artificial Sequence
<220> FEATURE:
<223> OTHER INFORMATION: Synthetic Construct

<400> SEQUENCE: 166
ttgttgagtc ggcg 14

<210> SEQ ID NO 167
<211> LENGTH: 14
<212> TYPE: DNA
<213> ORGANISM: Artificial Sequence
<220> FEATURE:
<223> OTHER INFORMATION: Synthetic Construct

<400> SEQUENCE: 167
tgttgagtcg gcgt 14

<210> SEQ ID NO 168
<211> LENGTH: 14
<212> TYPE: DNA
<213> ORGANISM: Artificial Sequence
<220> FEATURE:
<223> OTHER INFORMATION: Synthetic Construct

<400> SEQUENCE: 168
gttgagtcgg cgtt 14

<210> SEQ ID NO 169
<211> LENGTH: 14
<212> TYPE: DNA
<213> ORGANISM: Artificial Sequence
<220> FEATURE:
<223> OTHER INFORMATION: Synthetic Construct

<400> SEQUENCE: 169
ttgagtcggc gttt 14

<210> SEQ ID NO 170
<211> LENGTH: 14
<212> TYPE: DNA
<213> ORGANISM: Artificial Sequence
<220> FEATURE:
<223> OTHER INFORMATION: Synthetic Construct

<400> SEQUENCE: 170
tgagtcggcg ttta 14

<210> SEQ ID NO 171
<211> LENGTH: 14
<212> TYPE: DNA
<213> ORGANISM: Artificial Sequence
<220> FEATURE:
<223> OTHER INFORMATION: Synthetic Construct

<400> SEQUENCE: 171
gagtcggcgt ttag 14

<210> SEQ ID NO 172
<211> LENGTH: 14
<212> TYPE: DNA
<213> ORGANISM: Artificial Sequence
<220> FEATURE:
<223> OTHER INFORMATION: Synthetic Construct

<400> SEQUENCE: 172
agtcggcgtt tagg 14

<210> SEQ ID NO 173
<211> LENGTH: 14
<212> TYPE: DNA
<213> ORGANISM: Artificial Sequence
<220> FEATURE:
<223> OTHER INFORMATION: Synthetic Construct

<400> SEQUENCE: 173
gtcggcgttt aggg 14

<210> SEQ ID NO 174
<211> LENGTH: 14
<212> TYPE: DNA
<213> ORGANISM: Artificial Sequence
<220> FEATURE:
<223> OTHER INFORMATION: Synthetic Construct

<400> SEQUENCE: 174
tcggcgttta gggt 14

<210> SEQ ID NO 175
<211> LENGTH: 14
<212> TYPE: DNA

<213> ORGANISM: Artificial Sequence
<220> FEATURE:
<223> OTHER INFORMATION: Synthetic Construct

<400> SEQUENCE: 175
cggcgtttag ggtc 14

<210> SEQ ID NO 176
<211> LENGTH: 14
<212> TYPE: DNA
<213> ORGANISM: Artificial Sequence
<220> FEATURE:
<223> OTHER INFORMATION: Synthetic Construct

<400> SEQUENCE: 176
ggcgtttagg gtcg 14

<210> SEQ ID NO 177
<211> LENGTH: 14
<212> TYPE: DNA
<213> ORGANISM: Artificial Sequence
<220> FEATURE:
<223> OTHER INFORMATION: Synthetic Construct

<400> SEQUENCE: 177
gcgtttaggg tcgg 14

<210> SEQ ID NO 178
<211> LENGTH: 14
<212> TYPE: DNA
<213> ORGANISM: Artificial Sequence
<220> FEATURE:
<223> OTHER INFORMATION: Synthetic Construct

<400> SEQUENCE: 178
cgtttagggt cggg 14

<210> SEQ ID NO 179
<211> LENGTH: 14
<212> TYPE: DNA
<213> ORGANISM: Artificial Sequence
<220> FEATURE:
<223> OTHER INFORMATION: Synthetic Construct

<400> SEQUENCE: 179
gtttagggtc gggg 14

<210> SEQ ID NO 180
<211> LENGTH: 14
<212> TYPE: DNA
<213> ORGANISM: Artificial Sequence
<220> FEATURE:
<223> OTHER INFORMATION: Synthetic Construct

<400> SEQUENCE: 180
tttagggtcg gggg 14

<210> SEQ ID NO 181
<211> LENGTH: 14
<212> TYPE: DNA
<213> ORGANISM: Artificial Sequence
<220> FEATURE:
<223> OTHER INFORMATION: Synthetic Construct

<400> SEQUENCE: 181
ttagggtcgg gggt 14

<210> SEQ ID NO 182
<211> LENGTH: 14
<212> TYPE: DNA
<213> ORGANISM: Artificial Sequence
<220> FEATURE:
<223> OTHER INFORMATION: Synthetic Construct

<400> SEQUENCE: 182
tagggtcggg ggta 14

<210> SEQ ID NO 183
<211> LENGTH: 14
<212> TYPE: DNA
<213> ORGANISM: Artificial Sequence
<220> FEATURE:
<223> OTHER INFORMATION: Synthetic Construct

<400> SEQUENCE: 183
agggtcgggg gtag 14

<210> SEQ ID NO 184
<211> LENGTH: 14
<212> TYPE: DNA
<213> ORGANISM: Artificial Sequence
<220> FEATURE:
<223> OTHER INFORMATION: Synthetic Construct

<400> SEQUENCE: 184
gggtcggggg taga 14

<210> SEQ ID NO 185
<211> LENGTH: 14
<212> TYPE: DNA
<213> ORGANISM: Artificial Sequence
<220> FEATURE:
<223> OTHER INFORMATION: Synthetic Construct

<400> SEQUENCE: 185
ggtcgggggt agag 14

<210> SEQ ID NO 186
<211> LENGTH: 14
<212> TYPE: DNA
<213> ORGANISM: Artificial Sequence
<220> FEATURE:
<223> OTHER INFORMATION: Synthetic Construct

<400> SEQUENCE: 186
gtcgggggta gagt 14

<210> SEQ ID NO 187
<211> LENGTH: 14
<212> TYPE: DNA
<213> ORGANISM: Artificial Sequence
<220> FEATURE:
<223> OTHER INFORMATION: Synthetic Construct

<400> SEQUENCE: 187
tcgggggtag agtt 14

<210> SEQ ID NO 188
<211> LENGTH: 14
<212> TYPE: DNA
<213> ORGANISM: Artificial Sequence
<220> FEATURE:

<223> OTHER INFORMATION: Synthetic Construct

<400> SEQUENCE: 188
cgggggtaga gttt 14

<210> SEQ ID NO 189
<211> LENGTH: 14
<212> TYPE: DNA
<213> ORGANISM: Artificial Sequence
<220> FEATURE:
<223> OTHER INFORMATION: Synthetic Construct

<400> SEQUENCE: 189
actacgaacc acac 14

<210> SEQ ID NO 190
<211> LENGTH: 24
<212> TYPE: DNA
<213> ORGANISM: Artificial Sequence
<220> FEATURE:
<223> OTHER INFORMATION: Synthetic Construct

<400> SEQUENCE: 190
agtttttgtc gcgtgcgtgt tcga 24

<210> SEQ ID NO 191
<211> LENGTH: 14
<212> TYPE: DNA
<213> ORGANISM: Artificial Sequence
<220> FEATURE:
<223> OTHER INFORMATION: Synthetic Construct

<400> SEQUENCE: 191
gggggtagag tttc 14

<210> SEQ ID NO 192
<211> LENGTH: 14
<212> TYPE: DNA
<213> ORGANISM: Artificial Sequence
<220> FEATURE:
<223> OTHER INFORMATION: Synthetic Construct

<400> SEQUENCE: 192
ggggtagagt ttcg 14

<210> SEQ ID NO 193
<211> LENGTH: 14
<212> TYPE: DNA
<213> ORGANISM: Artificial Sequence
<220> FEATURE:
<223> OTHER INFORMATION: Synthetic Construct

<400> SEQUENCE: 193
gggtagagtt tcga 14

<210> SEQ ID NO 194
<211> LENGTH: 14
<212> TYPE: DNA
<213> ORGANISM: Artificial Sequence
<220> FEATURE:
<223> OTHER INFORMATION: Synthetic Construct

<400> SEQUENCE: 194
ggtagagttt cgag 14

-continued

<210> SEQ ID NO 195
<211> LENGTH: 14
<212> TYPE: DNA
<213> ORGANISM: Artificial Sequence
<220> FEATURE:
<223> OTHER INFORMATION: Synthetic Construct

<400> SEQUENCE: 195
gtagagtttc gagt 14

<210> SEQ ID NO 196
<211> LENGTH: 14
<212> TYPE: DNA
<213> ORGANISM: Artificial Sequence
<220> FEATURE:
<223> OTHER INFORMATION: Synthetic Construct

<400> SEQUENCE: 196
tagagtttcg agtt 14

<210> SEQ ID NO 197
<211> LENGTH: 14
<212> TYPE: DNA
<213> ORGANISM: Artificial Sequence
<220> FEATURE:
<223> OTHER INFORMATION: Synthetic Construct

<400> SEQUENCE: 197
agagtttcga gttt 14

<210> SEQ ID NO 198
<211> LENGTH: 14
<212> TYPE: DNA
<213> ORGANISM: Artificial Sequence
<220> FEATURE:
<223> OTHER INFORMATION: Synthetic Construct

<400> SEQUENCE: 198
gagtttcgag tttt 14

<210> SEQ ID NO 199
<211> LENGTH: 14
<212> TYPE: DNA
<213> ORGANISM: Artificial Sequence
<220> FEATURE:
<223> OTHER INFORMATION: Synthetic Construct

<400> SEQUENCE: 199
agtttcgagt tttt 14

<210> SEQ ID NO 200
<211> LENGTH: 14
<212> TYPE: DNA
<213> ORGANISM: Artificial Sequence
<220> FEATURE:
<223> OTHER INFORMATION: Synthetic Construct

<400> SEQUENCE: 200
gtttcgagtt tttt 14

<210> SEQ ID NO 201
<211> LENGTH: 14
<212> TYPE: DNA
<213> ORGANISM: Artificial Sequence
<220> FEATURE:
<223> OTHER INFORMATION: Synthetic Construct

<400> SEQUENCE: 201
tttcgagttt tttt 14

<210> SEQ ID NO 202
<211> LENGTH: 14
<212> TYPE: DNA
<213> ORGANISM: Artificial Sequence
<220> FEATURE:
<223> OTHER INFORMATION: Synthetic Construct

<400> SEQUENCE: 202
ttcgagtttt tttt 14

<210> SEQ ID NO 203
<211> LENGTH: 14
<212> TYPE: DNA
<213> ORGANISM: Artificial Sequence
<220> FEATURE:
<223> OTHER INFORMATION: Synthetic Construct

<400> SEQUENCE: 203
tcgagttttt tttg 14

<210> SEQ ID NO 204
<211> LENGTH: 14
<212> TYPE: DNA
<213> ORGANISM: Artificial Sequence
<220> FEATURE:
<223> OTHER INFORMATION: Synthetic Construct

<400> SEQUENCE: 204
cgagtttttt ttgc 14

<210> SEQ ID NO 205
<211> LENGTH: 14
<212> TYPE: DNA
<213> ORGANISM: Artificial Sequence
<220> FEATURE:
<223> OTHER INFORMATION: Synthetic Construct

<400> SEQUENCE: 205
gagttttttt tgcg 14

<210> SEQ ID NO 206
<211> LENGTH: 14
<212> TYPE: DNA
<213> ORGANISM: Artificial Sequence
<220> FEATURE:
<223> OTHER INFORMATION: Synthetic Construct

<400> SEQUENCE: 206
agtttttttt gcgg 14

<210> SEQ ID NO 207
<211> LENGTH: 14
<212> TYPE: DNA
<213> ORGANISM: Artificial Sequence
<220> FEATURE:
<223> OTHER INFORMATION: Synthetic Construct

<400> SEQUENCE: 207
gttttttttg cgga 14

<210> SEQ ID NO 208
<211> LENGTH: 14

<212> TYPE: DNA
<213> ORGANISM: Artificial Sequence
<220> FEATURE:
<223> OTHER INFORMATION: Synthetic Construct

<400> SEQUENCE: 208
ttttttttgc ggaa 14

<210> SEQ ID NO 209
<211> LENGTH: 14
<212> TYPE: DNA
<213> ORGANISM: Artificial Sequence
<220> FEATURE:
<223> OTHER INFORMATION: Synthetic Construct

<400> SEQUENCE: 209
tttttttgcg gaat 14

<210> SEQ ID NO 210
<211> LENGTH: 14
<212> TYPE: DNA
<213> ORGANISM: Artificial Sequence
<220> FEATURE:
<223> OTHER INFORMATION: Synthetic Construct

<400> SEQUENCE: 210
ttttttgcgg aatt 14

<210> SEQ ID NO 211
<211> LENGTH: 14
<212> TYPE: DNA
<213> ORGANISM: Artificial Sequence
<220> FEATURE:
<223> OTHER INFORMATION: Synthetic Construct

<400> SEQUENCE: 211
tttttgcgga atta 14

<210> SEQ ID NO 212
<211> LENGTH: 14
<212> TYPE: DNA
<213> ORGANISM: Artificial Sequence
<220> FEATURE:
<223> OTHER INFORMATION: Synthetic Construct

<400> SEQUENCE: 212
ttttgcggaa ttaa 14

<210> SEQ ID NO 213
<211> LENGTH: 14
<212> TYPE: DNA
<213> ORGANISM: Artificial Sequence
<220> FEATURE:
<223> OTHER INFORMATION: Synthetic Construct

<400> SEQUENCE: 213
tttgcggaat taag 14

<210> SEQ ID NO 214
<211> LENGTH: 14
<212> TYPE: DNA
<213> ORGANISM: Artificial Sequence
<220> FEATURE:
<223> OTHER INFORMATION: Synthetic Construct

<400> SEQUENCE: 214
ttgcggaatt aagg 14

<210> SEQ ID NO 215
<211> LENGTH: 14
<212> TYPE: DNA
<213> ORGANISM: Artificial Sequence
<220> FEATURE:
<223> OTHER INFORMATION: Synthetic Construct

<400> SEQUENCE: 215
tgcggaatta agga 14

<210> SEQ ID NO 216
<211> LENGTH: 14
<212> TYPE: DNA
<213> ORGANISM: Artificial Sequence
<220> FEATURE:
<223> OTHER INFORMATION: Synthetic Construct

<400> SEQUENCE: 216
gcggaattaa ggag 14

<210> SEQ ID NO 217
<211> LENGTH: 14
<212> TYPE: DNA
<213> ORGANISM: Artificial Sequence
<220> FEATURE:
<223> OTHER INFORMATION: Synthetic Construct

<400> SEQUENCE: 217
cggaattaag gaga 14

<210> SEQ ID NO 218
<211> LENGTH: 14
<212> TYPE: DNA
<213> ORGANISM: Artificial Sequence
<220> FEATURE:
<223> OTHER INFORMATION: Synthetic Construct

<400> SEQUENCE: 218
ggaattaagg agat 14

<210> SEQ ID NO 219
<211> LENGTH: 14
<212> TYPE: DNA
<213> ORGANISM: Artificial Sequence
<220> FEATURE:
<223> OTHER INFORMATION: Synthetic Construct

<400> SEQUENCE: 219
gaattaagga gatt 14

<210> SEQ ID NO 220
<211> LENGTH: 14
<212> TYPE: DNA
<213> ORGANISM: Artificial Sequence
<220> FEATURE:
<223> OTHER INFORMATION: Synthetic Construct

<400> SEQUENCE: 220
aattaaggag attt 14

<210> SEQ ID NO 221
<211> LENGTH: 14
<212> TYPE: DNA
<213> ORGANISM: Artificial Sequence
<220> FEATURE:
<223> OTHER INFORMATION: Synthetic Construct

<400> SEQUENCE: 221
attaaggaga tttt 14

<210> SEQ ID NO 222
<211> LENGTH: 14
<212> TYPE: DNA
<213> ORGANISM: Artificial Sequence
<220> FEATURE:
<223> OTHER INFORMATION: Synthetic Construct

<400> SEQUENCE: 222
ttaaggagat tttt 14

<210> SEQ ID NO 223
<211> LENGTH: 14
<212> TYPE: DNA
<213> ORGANISM: Artificial Sequence
<220> FEATURE:
<223> OTHER INFORMATION: Synthetic Construct

<400> SEQUENCE: 223
taaggagatt tttg 14

<210> SEQ ID NO 224
<211> LENGTH: 14
<212> TYPE: DNA
<213> ORGANISM: Artificial Sequence
<220> FEATURE:
<223> OTHER INFORMATION: Synthetic Construct

<400> SEQUENCE: 224
aaggagattt ttgg 14

<210> SEQ ID NO 225
<211> LENGTH: 14
<212> TYPE: DNA
<213> ORGANISM: Artificial Sequence
<220> FEATURE:
<223> OTHER INFORMATION: Synthetic Construct

<400> SEQUENCE: 225
aggagatttt tggc 14

<210> SEQ ID NO 226
<211> LENGTH: 14
<212> TYPE: DNA
<213> ORGANISM: Artificial Sequence
<220> FEATURE:
<223> OTHER INFORMATION: Synthetic Construct

<400> SEQUENCE: 226
ggagattttt ggcg 14

<210> SEQ ID NO 227
<211> LENGTH: 14
<212> TYPE: DNA
<213> ORGANISM: Artificial Sequence
<220> FEATURE:
<223> OTHER INFORMATION: Synthetic Construct

<400> SEQUENCE: 227
gagatttttg gcga 14

-continued

<210> SEQ ID NO 228
<211> LENGTH: 14
<212> TYPE: DNA
<213> ORGANISM: Artificial Sequence
<220> FEATURE:
<223> OTHER INFORMATION: Synthetic Construct

<400> SEQUENCE: 228
agatttttgg cgat 14

<210> SEQ ID NO 229
<211> LENGTH: 14
<212> TYPE: DNA
<213> ORGANISM: Artificial Sequence
<220> FEATURE:
<223> OTHER INFORMATION: Synthetic Construct

<400> SEQUENCE: 229
gatttttggc gatc 14

<210> SEQ ID NO 230
<211> LENGTH: 14
<212> TYPE: DNA
<213> ORGANISM: Artificial Sequence
<220> FEATURE:
<223> OTHER INFORMATION: Synthetic Construct

<400> SEQUENCE: 230
atttttggcg atcg 14

<210> SEQ ID NO 231
<211> LENGTH: 14
<212> TYPE: DNA
<213> ORGANISM: Artificial Sequence
<220> FEATURE:
<223> OTHER INFORMATION: Synthetic Construct

<400> SEQUENCE: 231
tttttggcga tcgg 14

<210> SEQ ID NO 232
<211> LENGTH: 14
<212> TYPE: DNA
<213> ORGANISM: Artificial Sequence
<220> FEATURE:
<223> OTHER INFORMATION: Synthetic Construct

<400> SEQUENCE: 232
gataataaac ccga 14

<210> SEQ ID NO 233
<211> LENGTH: 25
<212> TYPE: DNA
<213> ORGANISM: Artificial Sequence
<220> FEATURE:
<223> OTHER INFORMATION: Synthetic Construct

<400> SEQUENCE: 233
gtttagggcg gggagagttg gcgat 25

<210> SEQ ID NO 234
<211> LENGTH: 14
<212> TYPE: DNA
<213> ORGANISM: Artificial Sequence
<220> FEATURE:
<223> OTHER INFORMATION: Synthetic Construct

<400> SEQUENCE: 234
ttttggcgat cggg 14

<210> SEQ ID NO 235
<211> LENGTH: 14
<212> TYPE: DNA
<213> ORGANISM: Artificial Sequence
<220> FEATURE:
<223> OTHER INFORMATION: Synthetic Construct

<400> SEQUENCE: 235
tttggcgatc gggg 14

<210> SEQ ID NO 236
<211> LENGTH: 14
<212> TYPE: DNA
<213> ORGANISM: Artificial Sequence
<220> FEATURE:
<223> OTHER INFORMATION: Synthetic Construct

<400> SEQUENCE: 236
ttggcgatcg ggga 14

<210> SEQ ID NO 237
<211> LENGTH: 14
<212> TYPE: DNA
<213> ORGANISM: Artificial Sequence
<220> FEATURE:
<223> OTHER INFORMATION: Synthetic Construct

<400> SEQUENCE: 237
tggcgatcgg ggag 14

<210> SEQ ID NO 238
<211> LENGTH: 14
<212> TYPE: DNA
<213> ORGANISM: Artificial Sequence
<220> FEATURE:
<223> OTHER INFORMATION: Synthetic Construct

<400> SEQUENCE: 238
ggcgatcggg gagt 14

<210> SEQ ID NO 239
<211> LENGTH: 14
<212> TYPE: DNA
<213> ORGANISM: Artificial Sequence
<220> FEATURE:
<223> OTHER INFORMATION: Synthetic Construct

<400> SEQUENCE: 239
gcgatcgggg agtt 14

<210> SEQ ID NO 240
<211> LENGTH: 14
<212> TYPE: DNA
<213> ORGANISM: Artificial Sequence
<220> FEATURE:
<223> OTHER INFORMATION: Synthetic Construct

<400> SEQUENCE: 240
cgatcgggga gttt 14

<210> SEQ ID NO 241

<211> LENGTH: 14
<212> TYPE: DNA
<213> ORGANISM: Artificial Sequence
<220> FEATURE:
<223> OTHER INFORMATION: Synthetic Construct

<400> SEQUENCE: 241
gatcggggag tttg 14

<210> SEQ ID NO 242
<211> LENGTH: 14
<212> TYPE: DNA
<213> ORGANISM: Artificial Sequence
<220> FEATURE:
<223> OTHER INFORMATION: Synthetic Construct

<400> SEQUENCE: 242
atcggggagt ttgt 14

<210> SEQ ID NO 243
<211> LENGTH: 14
<212> TYPE: DNA
<213> ORGANISM: Artificial Sequence
<220> FEATURE:
<223> OTHER INFORMATION: Synthetic Construct

<400> SEQUENCE: 243
tcggggagtt tgtt 14

<210> SEQ ID NO 244
<211> LENGTH: 14
<212> TYPE: DNA
<213> ORGANISM: Artificial Sequence
<220> FEATURE:
<223> OTHER INFORMATION: Synthetic Construct

<400> SEQUENCE: 244
cggggagttt gttt 14

<210> SEQ ID NO 245
<211> LENGTH: 14
<212> TYPE: DNA
<213> ORGANISM: Artificial Sequence
<220> FEATURE:
<223> OTHER INFORMATION: Synthetic Construct

<400> SEQUENCE: 245
ggggagtttg tttt 14

<210> SEQ ID NO 246
<211> LENGTH: 14
<212> TYPE: DNA
<213> ORGANISM: Artificial Sequence
<220> FEATURE:
<223> OTHER INFORMATION: Synthetic Construct

<400> SEQUENCE: 246
gggagtttgt tttt 14

<210> SEQ ID NO 247
<211> LENGTH: 14
<212> TYPE: DNA
<213> ORGANISM: Artificial Sequence
<220> FEATURE:
<223> OTHER INFORMATION: Synthetic Construct

<400> SEQUENCE: 247
ggagtttgtt tttg 14

<210> SEQ ID NO 248
<211> LENGTH: 14
<212> TYPE: DNA
<213> ORGANISM: Artificial Sequence
<220> FEATURE:
<223> OTHER INFORMATION: Synthetic Construct

<400> SEQUENCE: 248
gagtttgttt ttgt 14

<210> SEQ ID NO 249
<211> LENGTH: 14
<212> TYPE: DNA
<213> ORGANISM: Artificial Sequence
<220> FEATURE:
<223> OTHER INFORMATION: Synthetic Construct

<400> SEQUENCE: 249
agtttgtttt tgtg 14

<210> SEQ ID NO 250
<211> LENGTH: 14
<212> TYPE: DNA
<213> ORGANISM: Artificial Sequence
<220> FEATURE:
<223> OTHER INFORMATION: Synthetic Construct

<400> SEQUENCE: 250
gtttgttttt gtga 14

<210> SEQ ID NO 251
<211> LENGTH: 14
<212> TYPE: DNA
<213> ORGANISM: Artificial Sequence
<220> FEATURE:
<223> OTHER INFORMATION: Synthetic Construct

<400> SEQUENCE: 251
tttgtttttg tgat 14

<210> SEQ ID NO 252
<211> LENGTH: 14
<212> TYPE: DNA
<213> ORGANISM: Artificial Sequence
<220> FEATURE:
<223> OTHER INFORMATION: Synthetic Construct

<400> SEQUENCE: 252
ttgtttttgt gatc 14

<210> SEQ ID NO 253
<211> LENGTH: 14
<212> TYPE: DNA
<213> ORGANISM: Artificial Sequence
<220> FEATURE:
<223> OTHER INFORMATION: Synthetic Construct

<400> SEQUENCE: 253
tgtttttgtg atcg 14

<210> SEQ ID NO 254
<211> LENGTH: 14
<212> TYPE: DNA

<213> ORGANISM: Artificial Sequence
<220> FEATURE:
<223> OTHER INFORMATION: Synthetic Construct

<400> SEQUENCE: 254
gtttttgtga tcgt 14

<210> SEQ ID NO 255
<211> LENGTH: 14
<212> TYPE: DNA
<213> ORGANISM: Artificial Sequence
<220> FEATURE:
<223> OTHER INFORMATION: Synthetic Construct

<400> SEQUENCE: 255
tttttgtgat cgtt 14

<210> SEQ ID NO 256
<211> LENGTH: 14
<212> TYPE: DNA
<213> ORGANISM: Artificial Sequence
<220> FEATURE:
<223> OTHER INFORMATION: Synthetic Construct

<400> SEQUENCE: 256
ttttgtgatc gttt 14

<210> SEQ ID NO 257
<211> LENGTH: 14
<212> TYPE: DNA
<213> ORGANISM: Artificial Sequence
<220> FEATURE:
<223> OTHER INFORMATION: Synthetic Construct

<400> SEQUENCE: 257
tttgtgatcg tttt 14

<210> SEQ ID NO 258
<211> LENGTH: 14
<212> TYPE: DNA
<213> ORGANISM: Artificial Sequence
<220> FEATURE:
<223> OTHER INFORMATION: Synthetic Construct

<400> SEQUENCE: 258
ttgtgatcgt ttta 14

<210> SEQ ID NO 259
<211> LENGTH: 14
<212> TYPE: DNA
<213> ORGANISM: Artificial Sequence
<220> FEATURE:
<223> OTHER INFORMATION: Synthetic Construct

<400> SEQUENCE: 259
tgtgatcgtt ttag 14

<210> SEQ ID NO 260
<211> LENGTH: 14
<212> TYPE: DNA
<213> ORGANISM: Artificial Sequence
<220> FEATURE:
<223> OTHER INFORMATION: Synthetic Construct

<400> SEQUENCE: 260
gtgatcgttt tagt 14

-continued

<210> SEQ ID NO 261
<211> LENGTH: 14
<212> TYPE: DNA
<213> ORGANISM: Artificial Sequence
<220> FEATURE:
<223> OTHER INFORMATION: Synthetic Construct

<400> SEQUENCE: 261
tgatcgtttt agta 14

<210> SEQ ID NO 262
<211> LENGTH: 14
<212> TYPE: DNA
<213> ORGANISM: Artificial Sequence
<220> FEATURE:
<223> OTHER INFORMATION: Synthetic Construct

<400> SEQUENCE: 262
gatcgtttta gtag 14

<210> SEQ ID NO 263
<211> LENGTH: 14
<212> TYPE: DNA
<213> ORGANISM: Artificial Sequence
<220> FEATURE:
<223> OTHER INFORMATION: Synthetic Construct

<400> SEQUENCE: 263
atcgttttag tagt 14

<210> SEQ ID NO 264
<211> LENGTH: 14
<212> TYPE: DNA
<213> ORGANISM: Artificial Sequence
<220> FEATURE:
<223> OTHER INFORMATION: Synthetic Construct

<400> SEQUENCE: 264
tcgttttagt agtt 14

<210> SEQ ID NO 265
<211> LENGTH: 14
<212> TYPE: DNA
<213> ORGANISM: Artificial Sequence
<220> FEATURE:
<223> OTHER INFORMATION: Synthetic Construct

<400> SEQUENCE: 265
cgttttagta gttt 14

<210> SEQ ID NO 266
<211> LENGTH: 14
<212> TYPE: DNA
<213> ORGANISM: Artificial Sequence
<220> FEATURE:
<223> OTHER INFORMATION: Synthetic Construct

<400> SEQUENCE: 266
gttttagtag tttt 14

<210> SEQ ID NO 267
<211> LENGTH: 14
<212> TYPE: DNA
<213> ORGANISM: Artificial Sequence
<220> FEATURE:

<223> OTHER INFORMATION: Synthetic Construct

<400> SEQUENCE: 267
ttttagtagt tttt 14

<210> SEQ ID NO 268
<211> LENGTH: 14
<212> TYPE: DNA
<213> ORGANISM: Artificial Sequence
<220> FEATURE:
<223> OTHER INFORMATION: Synthetic Construct

<400> SEQUENCE: 268
tttagtagtt tttg 14

<210> SEQ ID NO 269
<211> LENGTH: 14
<212> TYPE: DNA
<213> ORGANISM: Artificial Sequence
<220> FEATURE:
<223> OTHER INFORMATION: Synthetic Construct

<400> SEQUENCE: 269
ttagtagttt ttgt 14

<210> SEQ ID NO 270
<211> LENGTH: 14
<212> TYPE: DNA
<213> ORGANISM: Artificial Sequence
<220> FEATURE:
<223> OTHER INFORMATION: Synthetic Construct

<400> SEQUENCE: 270
tagtagtttt tgtc 14

<210> SEQ ID NO 271
<211> LENGTH: 14
<212> TYPE: DNA
<213> ORGANISM: Artificial Sequence
<220> FEATURE:
<223> OTHER INFORMATION: Synthetic Construct

<400> SEQUENCE: 271
agtagttttt gtcg 14

<210> SEQ ID NO 272
<211> LENGTH: 14
<212> TYPE: DNA
<213> ORGANISM: Artificial Sequence
<220> FEATURE:
<223> OTHER INFORMATION: Synthetic Construct

<400> SEQUENCE: 272
gtagtttttg tcgc 14

<210> SEQ ID NO 273
<211> LENGTH: 14
<212> TYPE: DNA
<213> ORGANISM: Artificial Sequence
<220> FEATURE:
<223> OTHER INFORMATION: Synthetic Construct

<400> SEQUENCE: 273
tagtttttgt cgcg 14

<210> SEQ ID NO 274
<211> LENGTH: 14
<212> TYPE: DNA
<213> ORGANISM: Artificial Sequence
<220> FEATURE:
<223> OTHER INFORMATION: Synthetic Construct

<400> SEQUENCE: 274
agtttttgtc gcgt 14

<210> SEQ ID NO 275
<211> LENGTH: 14
<212> TYPE: DNA
<213> ORGANISM: Artificial Sequence
<220> FEATURE:
<223> OTHER INFORMATION: Synthetic Construct

<400> SEQUENCE: 275
gtttttgtcg cgtg 14

<210> SEQ ID NO 276
<211> LENGTH: 14
<212> TYPE: DNA
<213> ORGANISM: Artificial Sequence
<220> FEATURE:
<223> OTHER INFORMATION: Synthetic Construct

<400> SEQUENCE: 276
tttttgtcgc gtgc 14

<210> SEQ ID NO 277
<211> LENGTH: 14
<212> TYPE: DNA
<213> ORGANISM: Artificial Sequence
<220> FEATURE:
<223> OTHER INFORMATION: Synthetic Construct

<400> SEQUENCE: 277
ttttgtcgcg tgcg 14

<210> SEQ ID NO 278
<211> LENGTH: 14
<212> TYPE: DNA
<213> ORGANISM: Artificial Sequence
<220> FEATURE:
<223> OTHER INFORMATION: Synthetic Construct

<400> SEQUENCE: 278
tttgtcgcgt gcgt 14

<210> SEQ ID NO 279
<211> LENGTH: 14
<212> TYPE: DNA
<213> ORGANISM: Artificial Sequence
<220> FEATURE:
<223> OTHER INFORMATION: Synthetic Construct

<400> SEQUENCE: 279
ttgtcgcgtg cgtg 14

<210> SEQ ID NO 280
<211> LENGTH: 14
<212> TYPE: DNA
<213> ORGANISM: Artificial Sequence
<220> FEATURE:
<223> OTHER INFORMATION: Synthetic Construct

<400> SEQUENCE: 280
tgtcgcgtgc gtgt 14

<210> SEQ ID NO 281
<211> LENGTH: 14
<212> TYPE: DNA
<213> ORGANISM: Artificial Sequence
<220> FEATURE:
<223> OTHER INFORMATION: Synthetic Construct

<400> SEQUENCE: 281
gtcgcgtgcg tgtt 14

<210> SEQ ID NO 282
<211> LENGTH: 14
<212> TYPE: DNA
<213> ORGANISM: Artificial Sequence
<220> FEATURE:
<223> OTHER INFORMATION: Synthetic Construct

<400> SEQUENCE: 282
tcgcgtgcgt gttc 14

<210> SEQ ID NO 283
<211> LENGTH: 14
<212> TYPE: DNA
<213> ORGANISM: Artificial Sequence
<220> FEATURE:
<223> OTHER INFORMATION: Synthetic Construct

<400> SEQUENCE: 283
cgcgtgcgtg ttcg 14

<210> SEQ ID NO 284
<211> LENGTH: 14
<212> TYPE: DNA
<213> ORGANISM: Artificial Sequence
<220> FEATURE:
<223> OTHER INFORMATION: Synthetic Construct

<400> SEQUENCE: 284
gcgtgcgtgt tcga 14

<210> SEQ ID NO 285
<211> LENGTH: 14
<212> TYPE: DNA
<213> ORGANISM: Artificial Sequence
<220> FEATURE:
<223> OTHER INFORMATION: Synthetic Construct

<400> SEQUENCE: 285
cgtgcgtgtt cgag 14

<210> SEQ ID NO 286
<211> LENGTH: 14
<212> TYPE: DNA
<213> ORGANISM: Artificial Sequence
<220> FEATURE:
<223> OTHER INFORMATION: Synthetic Construct

<400> SEQUENCE: 286
gtgcgtgttc gagt 14

<210> SEQ ID NO 287
<211> LENGTH: 14

<212> TYPE: DNA
<213> ORGANISM: Artificial Sequence
<220> FEATURE:
<223> OTHER INFORMATION: Synthetic Construct

<400> SEQUENCE: 287
tgcgtgttcg agtg 14

<210> SEQ ID NO 288
<211> LENGTH: 14
<212> TYPE: DNA
<213> ORGANISM: Artificial Sequence
<220> FEATURE:
<223> OTHER INFORMATION: Synthetic Construct

<400> SEQUENCE: 288
gcgtgttcga gtgt 14

<210> SEQ ID NO 289
<211> LENGTH: 14
<212> TYPE: DNA
<213> ORGANISM: Artificial Sequence
<220> FEATURE:
<223> OTHER INFORMATION: Synthetic Construct

<400> SEQUENCE: 289
cgtgttcgag tgtg 14

<210> SEQ ID NO 290
<211> LENGTH: 14
<212> TYPE: DNA
<213> ORGANISM: Artificial Sequence
<220> FEATURE:
<223> OTHER INFORMATION: Synthetic Construct

<400> SEQUENCE: 290
gtgttcgagt gtgg 14

<210> SEQ ID NO 291
<211> LENGTH: 14
<212> TYPE: DNA
<213> ORGANISM: Artificial Sequence
<220> FEATURE:
<223> OTHER INFORMATION: Synthetic Construct

<400> SEQUENCE: 291
tgttcgagtg tggt 14

<210> SEQ ID NO 292
<211> LENGTH: 14
<212> TYPE: DNA
<213> ORGANISM: Artificial Sequence
<220> FEATURE:
<223> OTHER INFORMATION: Synthetic Construct

<400> SEQUENCE: 292
gttcgagtgt ggtt 14

<210> SEQ ID NO 293
<211> LENGTH: 14
<212> TYPE: DNA
<213> ORGANISM: Artificial Sequence
<220> FEATURE:
<223> OTHER INFORMATION: Synthetic Construct

<400> SEQUENCE: 293
ttcgagtgtg gttc 14

<210> SEQ ID NO 294
<211> LENGTH: 14
<212> TYPE: DNA
<213> ORGANISM: Artificial Sequence
<220> FEATURE:
<223> OTHER INFORMATION: Synthetic Construct

<400> SEQUENCE: 294
tcgagtgtgg ttcg 14

<210> SEQ ID NO 295
<211> LENGTH: 14
<212> TYPE: DNA
<213> ORGANISM: Artificial Sequence
<220> FEATURE:
<223> OTHER INFORMATION: Synthetic Construct

<400> SEQUENCE: 295
ccacgccgaa cgta 14

<210> SEQ ID NO 296
<211> LENGTH: 25
<212> TYPE: DNA
<213> ORGANISM: Artificial Sequence
<220> FEATURE:
<223> OTHER INFORMATION: Synthetic Construct

<400> SEQUENCE: 296
gtttgattag atggggtgcg gtttt 25

<210> SEQ ID NO 297
<211> LENGTH: 14
<212> TYPE: DNA
<213> ORGANISM: Artificial Sequence
<220> FEATURE:
<223> OTHER INFORMATION: Synthetic Construct

<400> SEQUENCE: 297
cgagtgtggt tcgt 14

<210> SEQ ID NO 298
<211> LENGTH: 14
<212> TYPE: DNA
<213> ORGANISM: Artificial Sequence
<220> FEATURE:
<223> OTHER INFORMATION: Synthetic Construct

<400> SEQUENCE: 298
gagtgtggtt cgta 14

<210> SEQ ID NO 299
<211> LENGTH: 14
<212> TYPE: DNA
<213> ORGANISM: Artificial Sequence
<220> FEATURE:
<223> OTHER INFORMATION: Synthetic Construct

<400> SEQUENCE: 299
agtgtggttc gtag 14

<210> SEQ ID NO 300
<211> LENGTH: 14
<212> TYPE: DNA
<213> ORGANISM: Artificial Sequence
<220> FEATURE:
<223> OTHER INFORMATION: Synthetic Construct

<400> SEQUENCE: 300
gtgtggttcg tagt 14

<210> SEQ ID NO 301
<211> LENGTH: 14
<212> TYPE: DNA
<213> ORGANISM: Artificial Sequence
<220> FEATURE:
<223> OTHER INFORMATION: Synthetic Construct

<400> SEQUENCE: 301
tgtggttcgt agtt 14

<210> SEQ ID NO 302
<211> LENGTH: 14
<212> TYPE: DNA
<213> ORGANISM: Artificial Sequence
<220> FEATURE:
<223> OTHER INFORMATION: Synthetic Construct

<400> SEQUENCE: 302
gtggttcgta gttt 14

<210> SEQ ID NO 303
<211> LENGTH: 14
<212> TYPE: DNA
<213> ORGANISM: Artificial Sequence
<220> FEATURE:
<223> OTHER INFORMATION: Synthetic Construct

<400> SEQUENCE: 303
tggttcgtag tttt 14

<210> SEQ ID NO 304
<211> LENGTH: 14
<212> TYPE: DNA
<213> ORGANISM: Artificial Sequence
<220> FEATURE:
<223> OTHER INFORMATION: Synthetic Construct

<400> SEQUENCE: 304
ggttcgtagt tttt 14

<210> SEQ ID NO 305
<211> LENGTH: 14
<212> TYPE: DNA
<213> ORGANISM: Artificial Sequence
<220> FEATURE:
<223> OTHER INFORMATION: Synthetic Construct

<400> SEQUENCE: 305
gttcgtagtt ttta 14

<210> SEQ ID NO 306
<211> LENGTH: 14
<212> TYPE: DNA
<213> ORGANISM: Artificial Sequence
<220> FEATURE:
<223> OTHER INFORMATION: Synthetic Construct

<400> SEQUENCE: 306
ttcgtagttt ttaa 14

<210> SEQ ID NO 307
<211> LENGTH: 14
<212> TYPE: DNA
<213> ORGANISM: Artificial Sequence
<220> FEATURE:
<223> OTHER INFORMATION: Synthetic Construct

<400> SEQUENCE: 307
tcgtagtttt taaa 14

<210> SEQ ID NO 308
<211> LENGTH: 14
<212> TYPE: DNA
<213> ORGANISM: Artificial Sequence
<220> FEATURE:
<223> OTHER INFORMATION: Synthetic Construct

<400> SEQUENCE: 308
cgtagttttt aaag 14

<210> SEQ ID NO 309
<211> LENGTH: 14
<212> TYPE: DNA
<213> ORGANISM: Artificial Sequence
<220> FEATURE:
<223> OTHER INFORMATION: Synthetic Construct

<400> SEQUENCE: 309
gtagttttta aagt 14

<210> SEQ ID NO 310
<211> LENGTH: 14
<212> TYPE: DNA
<213> ORGANISM: Artificial Sequence
<220> FEATURE:
<223> OTHER INFORMATION: Synthetic Construct

<400> SEQUENCE: 310
tagtttttaa agtt 14

<210> SEQ ID NO 311
<211> LENGTH: 14
<212> TYPE: DNA
<213> ORGANISM: Artificial Sequence
<220> FEATURE:
<223> OTHER INFORMATION: Synthetic Construct

<400> SEQUENCE: 311
agtttttaaa gttt 14

<210> SEQ ID NO 312
<211> LENGTH: 14
<212> TYPE: DNA
<213> ORGANISM: Artificial Sequence
<220> FEATURE:
<223> OTHER INFORMATION: Synthetic Construct

<400> SEQUENCE: 312
gtttttaaag ttta 14

<210> SEQ ID NO 313
<211> LENGTH: 14
<212> TYPE: DNA
<213> ORGANISM: Artificial Sequence
<220> FEATURE:
<223> OTHER INFORMATION: Synthetic Construct

<400> SEQUENCE: 313
tttttaaagt ttag 14

<210> SEQ ID NO 314
<211> LENGTH: 14
<212> TYPE: DNA
<213> ORGANISM: Artificial Sequence
<220> FEATURE:
<223> OTHER INFORMATION: Synthetic Construct

<400> SEQUENCE: 314
ttttaaagtt tagg 14

<210> SEQ ID NO 315
<211> LENGTH: 14
<212> TYPE: DNA
<213> ORGANISM: Artificial Sequence
<220> FEATURE:
<223> OTHER INFORMATION: Synthetic Construct

<400> SEQUENCE: 315
tttaaagttt aggt 14

<210> SEQ ID NO 316
<211> LENGTH: 14
<212> TYPE: DNA
<213> ORGANISM: Artificial Sequence
<220> FEATURE:
<223> OTHER INFORMATION: Synthetic Construct

<400> SEQUENCE: 316
ttaaagttta ggtg 14

<210> SEQ ID NO 317
<211> LENGTH: 14
<212> TYPE: DNA
<213> ORGANISM: Artificial Sequence
<220> FEATURE:
<223> OTHER INFORMATION: Synthetic Construct

<400> SEQUENCE: 317
taaagtttag gtgt 14

<210> SEQ ID NO 318
<211> LENGTH: 14
<212> TYPE: DNA
<213> ORGANISM: Artificial Sequence
<220> FEATURE:
<223> OTHER INFORMATION: Synthetic Construct

<400> SEQUENCE: 318
aaagtttagg tgtg 14

<210> SEQ ID NO 319
<211> LENGTH: 14
<212> TYPE: DNA
<213> ORGANISM: Artificial Sequence
<220> FEATURE:
<223> OTHER INFORMATION: Synthetic Construct

<400> SEQUENCE: 319
aagtttaggt gtgt 14

<210> SEQ ID NO 320

<211> LENGTH: 14
<212> TYPE: DNA
<213> ORGANISM: Artificial Sequence
<220> FEATURE:
<223> OTHER INFORMATION: Synthetic Construct

<400> SEQUENCE: 320
agtttaggtg tgtg 14

<210> SEQ ID NO 321
<211> LENGTH: 14
<212> TYPE: DNA
<213> ORGANISM: Artificial Sequence
<220> FEATURE:
<223> OTHER INFORMATION: Synthetic Construct

<400> SEQUENCE: 321
gtttaggtgt gtgt 14

<210> SEQ ID NO 322
<211> LENGTH: 14
<212> TYPE: DNA
<213> ORGANISM: Artificial Sequence
<220> FEATURE:
<223> OTHER INFORMATION: Synthetic Construct

<400> SEQUENCE: 322
tttaggtgtg tgtg 14

<210> SEQ ID NO 323
<211> LENGTH: 14
<212> TYPE: DNA
<213> ORGANISM: Artificial Sequence
<220> FEATURE:
<223> OTHER INFORMATION: Synthetic Construct

<400> SEQUENCE: 323
ttaggtgtgt gtgg 14

<210> SEQ ID NO 324
<211> LENGTH: 14
<212> TYPE: DNA
<213> ORGANISM: Artificial Sequence
<220> FEATURE:
<223> OTHER INFORMATION: Synthetic Construct

<400> SEQUENCE: 324
taggtgtgtg tggt 14

<210> SEQ ID NO 325
<211> LENGTH: 14
<212> TYPE: DNA
<213> ORGANISM: Artificial Sequence
<220> FEATURE:
<223> OTHER INFORMATION: Synthetic Construct

<400> SEQUENCE: 325
aggtgtgtgt ggtt 14

<210> SEQ ID NO 326
<211> LENGTH: 14
<212> TYPE: DNA
<213> ORGANISM: Artificial Sequence
<220> FEATURE:
<223> OTHER INFORMATION: Synthetic Construct

<400> SEQUENCE: 326
ggtgtgtgtg gttt 14

<210> SEQ ID NO 327
<211> LENGTH: 14
<212> TYPE: DNA
<213> ORGANISM: Artificial Sequence
<220> FEATURE:
<223> OTHER INFORMATION: Synthetic Construct

<400> SEQUENCE: 327
gtgtgtgtgg ttta 14

<210> SEQ ID NO 328
<211> LENGTH: 14
<212> TYPE: DNA
<213> ORGANISM: Artificial Sequence
<220> FEATURE:
<223> OTHER INFORMATION: Synthetic Construct

<400> SEQUENCE: 328
tgtgtgtggt ttag 14

<210> SEQ ID NO 329
<211> LENGTH: 14
<212> TYPE: DNA
<213> ORGANISM: Artificial Sequence
<220> FEATURE:
<223> OTHER INFORMATION: Synthetic Construct

<400> SEQUENCE: 329
gtgtgtggtt tagg 14

<210> SEQ ID NO 330
<211> LENGTH: 14
<212> TYPE: DNA
<213> ORGANISM: Artificial Sequence
<220> FEATURE:
<223> OTHER INFORMATION: Synthetic Construct

<400> SEQUENCE: 330
tgtgtggttt aggg 14

<210> SEQ ID NO 331
<211> LENGTH: 14
<212> TYPE: DNA
<213> ORGANISM: Artificial Sequence
<220> FEATURE:
<223> OTHER INFORMATION: Synthetic Construct

<400> SEQUENCE: 331
gtgtggttta gggc 14

<210> SEQ ID NO 332
<211> LENGTH: 14
<212> TYPE: DNA
<213> ORGANISM: Artificial Sequence
<220> FEATURE:
<223> OTHER INFORMATION: Synthetic Construct

<400> SEQUENCE: 332
tgtggtttag ggcg 14

<210> SEQ ID NO 333
<211> LENGTH: 14
<212> TYPE: DNA

<213> ORGANISM: Artificial Sequence
<220> FEATURE:
<223> OTHER INFORMATION: Synthetic Construct

<400> SEQUENCE: 333
gtggtttagg gcgg 14

<210> SEQ ID NO 334
<211> LENGTH: 14
<212> TYPE: DNA
<213> ORGANISM: Artificial Sequence
<220> FEATURE:
<223> OTHER INFORMATION: Synthetic Construct

<400> SEQUENCE: 334
tggtttaggg cggg 14

<210> SEQ ID NO 335
<211> LENGTH: 14
<212> TYPE: DNA
<213> ORGANISM: Artificial Sequence
<220> FEATURE:
<223> OTHER INFORMATION: Synthetic Construct

<400> SEQUENCE: 335
ggtttagggc gggg 14

<210> SEQ ID NO 336
<211> LENGTH: 14
<212> TYPE: DNA
<213> ORGANISM: Artificial Sequence
<220> FEATURE:
<223> OTHER INFORMATION: Synthetic Construct

<400> SEQUENCE: 336
gtttagggcg ggga 14

<210> SEQ ID NO 337
<211> LENGTH: 14
<212> TYPE: DNA
<213> ORGANISM: Artificial Sequence
<220> FEATURE:
<223> OTHER INFORMATION: Synthetic Construct

<400> SEQUENCE: 337
tttagggcgg ggag 14

<210> SEQ ID NO 338
<211> LENGTH: 14
<212> TYPE: DNA
<213> ORGANISM: Artificial Sequence
<220> FEATURE:
<223> OTHER INFORMATION: Synthetic Construct

<400> SEQUENCE: 338
ttagggcggg gaga 14

<210> SEQ ID NO 339
<211> LENGTH: 14
<212> TYPE: DNA
<213> ORGANISM: Artificial Sequence
<220> FEATURE:
<223> OTHER INFORMATION: Synthetic Construct

<400> SEQUENCE: 339
tagggcgggg agag 14

<210> SEQ ID NO 340
<211> LENGTH: 14
<212> TYPE: DNA
<213> ORGANISM: Artificial Sequence
<220> FEATURE:
<223> OTHER INFORMATION: Synthetic Construct

<400> SEQUENCE: 340
agggcgggga gagt 14

<210> SEQ ID NO 341
<211> LENGTH: 14
<212> TYPE: DNA
<213> ORGANISM: Artificial Sequence
<220> FEATURE:
<223> OTHER INFORMATION: Synthetic Construct

<400> SEQUENCE: 341
gggcggggag agtt 14

<210> SEQ ID NO 342
<211> LENGTH: 14
<212> TYPE: DNA
<213> ORGANISM: Artificial Sequence
<220> FEATURE:
<223> OTHER INFORMATION: Synthetic Construct

<400> SEQUENCE: 342
ggcggggaga gttg 14

<210> SEQ ID NO 343
<211> LENGTH: 14
<212> TYPE: DNA
<213> ORGANISM: Artificial Sequence
<220> FEATURE:
<223> OTHER INFORMATION: Synthetic Construct

<400> SEQUENCE: 343
gcggggagag ttgg 14

<210> SEQ ID NO 344
<211> LENGTH: 14
<212> TYPE: DNA
<213> ORGANISM: Artificial Sequence
<220> FEATURE:
<223> OTHER INFORMATION: Synthetic Construct

<400> SEQUENCE: 344
cggggagagt tggc 14

<210> SEQ ID NO 345
<211> LENGTH: 14
<212> TYPE: DNA
<213> ORGANISM: Artificial Sequence
<220> FEATURE:
<223> OTHER INFORMATION: Synthetic Construct

<400> SEQUENCE: 345
ggggagagtt ggcg 14

<210> SEQ ID NO 346
<211> LENGTH: 14
<212> TYPE: DNA
<213> ORGANISM: Artificial Sequence
<220> FEATURE:

<223> OTHER INFORMATION: Synthetic Construct

<400> SEQUENCE: 346
gggagagttg gcga 14

<210> SEQ ID NO 347
<211> LENGTH: 14
<212> TYPE: DNA
<213> ORGANISM: Artificial Sequence
<220> FEATURE:
<223> OTHER INFORMATION: Synthetic Construct

<400> SEQUENCE: 347
ggagagttgg cgat 14

<210> SEQ ID NO 348
<211> LENGTH: 14
<212> TYPE: DNA
<213> ORGANISM: Artificial Sequence
<220> FEATURE:
<223> OTHER INFORMATION: Synthetic Construct

<400> SEQUENCE: 348
gagagttggc gatt 14

<210> SEQ ID NO 349
<211> LENGTH: 14
<212> TYPE: DNA
<213> ORGANISM: Artificial Sequence
<220> FEATURE:
<223> OTHER INFORMATION: Synthetic Construct

<400> SEQUENCE: 349
agagttggcg attc 14

<210> SEQ ID NO 350
<211> LENGTH: 14
<212> TYPE: DNA
<213> ORGANISM: Artificial Sequence
<220> FEATURE:
<223> OTHER INFORMATION: Synthetic Construct

<400> SEQUENCE: 350
gagttggcga ttcg 14

<210> SEQ ID NO 351
<211> LENGTH: 14
<212> TYPE: DNA
<213> ORGANISM: Artificial Sequence
<220> FEATURE:
<223> OTHER INFORMATION: Synthetic Construct

<400> SEQUENCE: 351
agttggcgat tcgg 14

<210> SEQ ID NO 352
<211> LENGTH: 14
<212> TYPE: DNA
<213> ORGANISM: Artificial Sequence
<220> FEATURE:
<223> OTHER INFORMATION: Synthetic Construct

<400> SEQUENCE: 352
gttggcgatt cggg 14

<210> SEQ ID NO 353
<211> LENGTH: 14
<212> TYPE: DNA
<213> ORGANISM: Artificial Sequence
<220> FEATURE:
<223> OTHER INFORMATION: Synthetic Construct

<400> SEQUENCE: 353
ttggcgattc gggt 14

<210> SEQ ID NO 354
<211> LENGTH: 14
<212> TYPE: DNA
<213> ORGANISM: Artificial Sequence
<220> FEATURE:
<223> OTHER INFORMATION: Synthetic Construct

<400> SEQUENCE: 354
tggcgattcg ggtt 14

<210> SEQ ID NO 355
<211> LENGTH: 14
<212> TYPE: DNA
<213> ORGANISM: Artificial Sequence
<220> FEATURE:
<223> OTHER INFORMATION: Synthetic Construct

<400> SEQUENCE: 355
ggcgattcgg gttt 14

<210> SEQ ID NO 356
<211> LENGTH: 14
<212> TYPE: DNA
<213> ORGANISM: Artificial Sequence
<220> FEATURE:
<223> OTHER INFORMATION: Synthetic Construct

<400> SEQUENCE: 356
gcgattcggg ttta 14

<210> SEQ ID NO 357
<211> LENGTH: 14
<212> TYPE: DNA
<213> ORGANISM: Artificial Sequence
<220> FEATURE:
<223> OTHER INFORMATION: Synthetic Construct

<400> SEQUENCE: 357
cgattcgggt ttat 14

<210> SEQ ID NO 358
<211> LENGTH: 14
<212> TYPE: DNA
<213> ORGANISM: Artificial Sequence
<220> FEATURE:
<223> OTHER INFORMATION: Synthetic Construct

<400> SEQUENCE: 358
tcaaaaattc cgcc 14

<210> SEQ ID NO 359
<211> LENGTH: 26
<212> TYPE: DNA
<213> ORGANISM: Artificial Sequence
<220> FEATURE:
<223> OTHER INFORMATION: Synthetic Construct

<400> SEQUENCE: 359
aagttcggtt ttcgttcgtt ttgcgc 26

<210> SEQ ID NO 360
<211> LENGTH: 14
<212> TYPE: DNA
<213> ORGANISM: Artificial Sequence
<220> FEATURE:
<223> OTHER INFORMATION: Synthetic Construct

<400> SEQUENCE: 360
gattcgggtt tatt 14

<210> SEQ ID NO 361
<211> LENGTH: 14
<212> TYPE: DNA
<213> ORGANISM: Artificial Sequence
<220> FEATURE:
<223> OTHER INFORMATION: Synthetic Construct

<400> SEQUENCE: 361
attcgggttt atta 14

<210> SEQ ID NO 362
<211> LENGTH: 14
<212> TYPE: DNA
<213> ORGANISM: Artificial Sequence
<220> FEATURE:
<223> OTHER INFORMATION: Synthetic Construct

<400> SEQUENCE: 362
ttcgggttta ttat 14

<210> SEQ ID NO 363
<211> LENGTH: 14
<212> TYPE: DNA
<213> ORGANISM: Artificial Sequence
<220> FEATURE:
<223> OTHER INFORMATION: Synthetic Construct

<400> SEQUENCE: 363
tcgggtttat tatc 14

<210> SEQ ID NO 364
<211> LENGTH: 14
<212> TYPE: DNA
<213> ORGANISM: Artificial Sequence
<220> FEATURE:
<223> OTHER INFORMATION: Synthetic Construct

<400> SEQUENCE: 364
cgggtttatt atcg 14

<210> SEQ ID NO 365
<211> LENGTH: 14
<212> TYPE: DNA
<213> ORGANISM: Artificial Sequence
<220> FEATURE:
<223> OTHER INFORMATION: Synthetic Construct

<400> SEQUENCE: 365
gggtttatta tcgt 14

<210> SEQ ID NO 366
<211> LENGTH: 14

-continued

<212> TYPE: DNA
<213> ORGANISM: Artificial Sequence
<220> FEATURE:
<223> OTHER INFORMATION: Synthetic Construct

<400> SEQUENCE: 366
ggtttattat cgtt 14

<210> SEQ ID NO 367
<211> LENGTH: 14
<212> TYPE: DNA
<213> ORGANISM: Artificial Sequence
<220> FEATURE:
<223> OTHER INFORMATION: Synthetic Construct

<400> SEQUENCE: 367
gtttattatc gttt 14

<210> SEQ ID NO 368
<211> LENGTH: 14
<212> TYPE: DNA
<213> ORGANISM: Artificial Sequence
<220> FEATURE:
<223> OTHER INFORMATION: Synthetic Construct

<400> SEQUENCE: 368
tttattatcg tttt 14

<210> SEQ ID NO 369
<211> LENGTH: 14
<212> TYPE: DNA
<213> ORGANISM: Artificial Sequence
<220> FEATURE:
<223> OTHER INFORMATION: Synthetic Construct

<400> SEQUENCE: 369
ttattatcgt ttta 14

<210> SEQ ID NO 370
<211> LENGTH: 14
<212> TYPE: DNA
<213> ORGANISM: Artificial Sequence
<220> FEATURE:
<223> OTHER INFORMATION: Synthetic Construct

<400> SEQUENCE: 370
tattatcgtt ttag 14

<210> SEQ ID NO 371
<211> LENGTH: 14
<212> TYPE: DNA
<213> ORGANISM: Artificial Sequence
<220> FEATURE:
<223> OTHER INFORMATION: Synthetic Construct

<400> SEQUENCE: 371
attatcgttt tagt 14

<210> SEQ ID NO 372
<211> LENGTH: 14
<212> TYPE: DNA
<213> ORGANISM: Artificial Sequence
<220> FEATURE:
<223> OTHER INFORMATION: Synthetic Construct

<400> SEQUENCE: 372
ttatcgtttt agtg 14

<210> SEQ ID NO 373
<211> LENGTH: 14
<212> TYPE: DNA
<213> ORGANISM: Artificial Sequence
<220> FEATURE:
<223> OTHER INFORMATION: Synthetic Construct

<400> SEQUENCE: 373
tatcgtttta gtgt 14

<210> SEQ ID NO 374
<211> LENGTH: 14
<212> TYPE: DNA
<213> ORGANISM: Artificial Sequence
<220> FEATURE:
<223> OTHER INFORMATION: Synthetic Construct

<400> SEQUENCE: 374
atcgttttag tgtt 14

<210> SEQ ID NO 375
<211> LENGTH: 14
<212> TYPE: DNA
<213> ORGANISM: Artificial Sequence
<220> FEATURE:
<223> OTHER INFORMATION: Synthetic Construct

<400> SEQUENCE: 375
tcgttttagt gtta 14

<210> SEQ ID NO 376
<211> LENGTH: 14
<212> TYPE: DNA
<213> ORGANISM: Artificial Sequence
<220> FEATURE:
<223> OTHER INFORMATION: Synthetic Construct

<400> SEQUENCE: 376
cgttttagtg ttat 14

<210> SEQ ID NO 377
<211> LENGTH: 14
<212> TYPE: DNA
<213> ORGANISM: Artificial Sequence
<220> FEATURE:
<223> OTHER INFORMATION: Synthetic Construct

<400> SEQUENCE: 377
gttttagtgt tatc 14

<210> SEQ ID NO 378
<211> LENGTH: 14
<212> TYPE: DNA
<213> ORGANISM: Artificial Sequence
<220> FEATURE:
<223> OTHER INFORMATION: Synthetic Construct

<400> SEQUENCE: 378
ttttagtgtt atcg 14

<210> SEQ ID NO 379
<211> LENGTH: 14
<212> TYPE: DNA
<213> ORGANISM: Artificial Sequence
<220> FEATURE:
<223> OTHER INFORMATION: Synthetic Construct

<400> SEQUENCE: 379
tttagtgtta tcgt 14

<210> SEQ ID NO 380
<211> LENGTH: 14
<212> TYPE: DNA
<213> ORGANISM: Artificial Sequence
<220> FEATURE:
<223> OTHER INFORMATION: Synthetic Construct

<400> SEQUENCE: 380
ttagtgttat cgtt 14

<210> SEQ ID NO 381
<211> LENGTH: 14
<212> TYPE: DNA
<213> ORGANISM: Artificial Sequence
<220> FEATURE:
<223> OTHER INFORMATION: Synthetic Construct

<400> SEQUENCE: 381
tagtgttatc gttt 14

<210> SEQ ID NO 382
<211> LENGTH: 14
<212> TYPE: DNA
<213> ORGANISM: Artificial Sequence
<220> FEATURE:
<223> OTHER INFORMATION: Synthetic Construct

<400> SEQUENCE: 382
agtgttatcg tttt 14

<210> SEQ ID NO 383
<211> LENGTH: 14
<212> TYPE: DNA
<213> ORGANISM: Artificial Sequence
<220> FEATURE:
<223> OTHER INFORMATION: Synthetic Construct

<400> SEQUENCE: 383
gtgttatcgt ttta 14

<210> SEQ ID NO 384
<211> LENGTH: 14
<212> TYPE: DNA
<213> ORGANISM: Artificial Sequence
<220> FEATURE:
<223> OTHER INFORMATION: Synthetic Construct

<400> SEQUENCE: 384
tgttatcgtt ttag 14

<210> SEQ ID NO 385
<211> LENGTH: 14
<212> TYPE: DNA
<213> ORGANISM: Artificial Sequence
<220> FEATURE:
<223> OTHER INFORMATION: Synthetic Construct

<400> SEQUENCE: 385
gttatcgttt tagt 14

-continued

<210> SEQ ID NO 386
<211> LENGTH: 14
<212> TYPE: DNA
<213> ORGANISM: Artificial Sequence
<220> FEATURE:
<223> OTHER INFORMATION: Synthetic Construct

<400> SEQUENCE: 386
ttatcgtttt agtg 14

<210> SEQ ID NO 387
<211> LENGTH: 14
<212> TYPE: DNA
<213> ORGANISM: Artificial Sequence
<220> FEATURE:
<223> OTHER INFORMATION: Synthetic Construct

<400> SEQUENCE: 387
tatcgtttta gtgt 14

<210> SEQ ID NO 388
<211> LENGTH: 14
<212> TYPE: DNA
<213> ORGANISM: Artificial Sequence
<220> FEATURE:
<223> OTHER INFORMATION: Synthetic Construct

<400> SEQUENCE: 388
atcgttttag tgtt 14

<210> SEQ ID NO 389
<211> LENGTH: 14
<212> TYPE: DNA
<213> ORGANISM: Artificial Sequence
<220> FEATURE:
<223> OTHER INFORMATION: Synthetic Construct

<400> SEQUENCE: 389
tcgttttagt gttt 14

<210> SEQ ID NO 390
<211> LENGTH: 14
<212> TYPE: DNA
<213> ORGANISM: Artificial Sequence
<220> FEATURE:
<223> OTHER INFORMATION: Synthetic Construct

<400> SEQUENCE: 390
cgttttagtg tttg 14

<210> SEQ ID NO 391
<211> LENGTH: 14
<212> TYPE: DNA
<213> ORGANISM: Artificial Sequence
<220> FEATURE:
<223> OTHER INFORMATION: Synthetic Construct

<400> SEQUENCE: 391
gttttagtgt ttga 14

<210> SEQ ID NO 392
<211> LENGTH: 14
<212> TYPE: DNA
<213> ORGANISM: Artificial Sequence
<220> FEATURE:
<223> OTHER INFORMATION: Synthetic Construct

<400> SEQUENCE: 392
ttttagtgtt tgat 14

<210> SEQ ID NO 393
<211> LENGTH: 14
<212> TYPE: DNA
<213> ORGANISM: Artificial Sequence
<220> FEATURE:
<223> OTHER INFORMATION: Synthetic Construct

<400> SEQUENCE: 393
tttagtgttt gatt 14

<210> SEQ ID NO 394
<211> LENGTH: 14
<212> TYPE: DNA
<213> ORGANISM: Artificial Sequence
<220> FEATURE:
<223> OTHER INFORMATION: Synthetic Construct

<400> SEQUENCE: 394
ttagtgtttg atta 14

<210> SEQ ID NO 395
<211> LENGTH: 14
<212> TYPE: DNA
<213> ORGANISM: Artificial Sequence
<220> FEATURE:
<223> OTHER INFORMATION: Synthetic Construct

<400> SEQUENCE: 395
tagtgtttga ttag 14

<210> SEQ ID NO 396
<211> LENGTH: 14
<212> TYPE: DNA
<213> ORGANISM: Artificial Sequence
<220> FEATURE:
<223> OTHER INFORMATION: Synthetic Construct

<400> SEQUENCE: 396
agtgtttgat taga 14

<210> SEQ ID NO 397
<211> LENGTH: 14
<212> TYPE: DNA
<213> ORGANISM: Artificial Sequence
<220> FEATURE:
<223> OTHER INFORMATION: Synthetic Construct

<400> SEQUENCE: 397
gtgtttgatt agat 14

<210> SEQ ID NO 398
<211> LENGTH: 14
<212> TYPE: DNA
<213> ORGANISM: Artificial Sequence
<220> FEATURE:
<223> OTHER INFORMATION: Synthetic Construct

<400> SEQUENCE: 398
tgtttgatta gatg 14

<210> SEQ ID NO 399

<211> LENGTH: 14
<212> TYPE: DNA
<213> ORGANISM: Artificial Sequence
<220> FEATURE:
<223> OTHER INFORMATION: Synthetic Construct

<400> SEQUENCE: 399
gtttgattag atgg 14

<210> SEQ ID NO 400
<211> LENGTH: 14
<212> TYPE: DNA
<213> ORGANISM: Artificial Sequence
<220> FEATURE:
<223> OTHER INFORMATION: Synthetic Construct

<400> SEQUENCE: 400
tttgattaga tggg 14

<210> SEQ ID NO 401
<211> LENGTH: 14
<212> TYPE: DNA
<213> ORGANISM: Artificial Sequence
<220> FEATURE:
<223> OTHER INFORMATION: Synthetic Construct

<400> SEQUENCE: 401
ttgattagat gggg 14

<210> SEQ ID NO 402
<211> LENGTH: 14
<212> TYPE: DNA
<213> ORGANISM: Artificial Sequence
<220> FEATURE:
<223> OTHER INFORMATION: Synthetic Construct

<400> SEQUENCE: 402
tgattagatg gggt 14

<210> SEQ ID NO 403
<211> LENGTH: 14
<212> TYPE: DNA
<213> ORGANISM: Artificial Sequence
<220> FEATURE:
<223> OTHER INFORMATION: Synthetic Construct

<400> SEQUENCE: 403
gattagatgg ggtg 14

<210> SEQ ID NO 404
<211> LENGTH: 14
<212> TYPE: DNA
<213> ORGANISM: Artificial Sequence
<220> FEATURE:
<223> OTHER INFORMATION: Synthetic Construct

<400> SEQUENCE: 404
attagatggg gtgc 14

<210> SEQ ID NO 405
<211> LENGTH: 14
<212> TYPE: DNA
<213> ORGANISM: Artificial Sequence
<220> FEATURE:
<223> OTHER INFORMATION: Synthetic Construct

<400> SEQUENCE: 405
ttagatgggg tgcg 14

<210> SEQ ID NO 406
<211> LENGTH: 14
<212> TYPE: DNA
<213> ORGANISM: Artificial Sequence
<220> FEATURE:
<223> OTHER INFORMATION: Synthetic Construct

<400> SEQUENCE: 406
tagatggggt gcgg 14

<210> SEQ ID NO 407
<211> LENGTH: 14
<212> TYPE: DNA
<213> ORGANISM: Artificial Sequence
<220> FEATURE:
<223> OTHER INFORMATION: Synthetic Construct

<400> SEQUENCE: 407
agatggggtg cggt 14

<210> SEQ ID NO 408
<211> LENGTH: 14
<212> TYPE: DNA
<213> ORGANISM: Artificial Sequence
<220> FEATURE:
<223> OTHER INFORMATION: Synthetic Construct

<400> SEQUENCE: 408
gatggggtgc ggtt 14

<210> SEQ ID NO 409
<211> LENGTH: 14
<212> TYPE: DNA
<213> ORGANISM: Artificial Sequence
<220> FEATURE:
<223> OTHER INFORMATION: Synthetic Construct

<400> SEQUENCE: 409
atggggtgcg gttt 14

<210> SEQ ID NO 410
<211> LENGTH: 14
<212> TYPE: DNA
<213> ORGANISM: Artificial Sequence
<220> FEATURE:
<223> OTHER INFORMATION: Synthetic Construct

<400> SEQUENCE: 410
tggggtgcgg tttt 14

<210> SEQ ID NO 411
<211> LENGTH: 14
<212> TYPE: DNA
<213> ORGANISM: Artificial Sequence
<220> FEATURE:
<223> OTHER INFORMATION: Synthetic Construct

<400> SEQUENCE: 411
ggggtgcggt tttt 14

<210> SEQ ID NO 412
<211> LENGTH: 14
<212> TYPE: DNA

<213> ORGANISM: Artificial Sequence
<220> FEATURE:
<223> OTHER INFORMATION: Synthetic Construct

<400> SEQUENCE: 412
gggtgcggtt ttta 14

<210> SEQ ID NO 413
<211> LENGTH: 14
<212> TYPE: DNA
<213> ORGANISM: Artificial Sequence
<220> FEATURE:
<223> OTHER INFORMATION: Synthetic Construct

<400> SEQUENCE: 413
ggtgcggttt ttac 14

<210> SEQ ID NO 414
<211> LENGTH: 14
<212> TYPE: DNA
<213> ORGANISM: Artificial Sequence
<220> FEATURE:
<223> OTHER INFORMATION: Synthetic Construct

<400> SEQUENCE: 414
gtgcggtttt tacg 14

<210> SEQ ID NO 415
<211> LENGTH: 14
<212> TYPE: DNA
<213> ORGANISM: Artificial Sequence
<220> FEATURE:
<223> OTHER INFORMATION: Synthetic Construct

<400> SEQUENCE: 415
tgcggttttt acgt 14

<210> SEQ ID NO 416
<211> LENGTH: 14
<212> TYPE: DNA
<213> ORGANISM: Artificial Sequence
<220> FEATURE:
<223> OTHER INFORMATION: Synthetic Construct

<400> SEQUENCE: 416
gcggttttta cgtt 14

<210> SEQ ID NO 417
<211> LENGTH: 14
<212> TYPE: DNA
<213> ORGANISM: Artificial Sequence
<220> FEATURE:
<223> OTHER INFORMATION: Synthetic Construct

<400> SEQUENCE: 417
cggtttttac gttc 14

<210> SEQ ID NO 418
<211> LENGTH: 14
<212> TYPE: DNA
<213> ORGANISM: Artificial Sequence
<220> FEATURE:
<223> OTHER INFORMATION: Synthetic Construct

<400> SEQUENCE: 418
ggtttttacg ttcg 14

<210> SEQ ID NO 419
<211> LENGTH: 14
<212> TYPE: DNA
<213> ORGANISM: Artificial Sequence
<220> FEATURE:
<223> OTHER INFORMATION: Synthetic Construct

<400> SEQUENCE: 419
gtttttacgt tcgg 14

<210> SEQ ID NO 420
<211> LENGTH: 14
<212> TYPE: DNA
<213> ORGANISM: Artificial Sequence
<220> FEATURE:
<223> OTHER INFORMATION: Synthetic Construct

<400> SEQUENCE: 420
tttttacgtt cggc 14

<210> SEQ ID NO 421
<211> LENGTH: 14
<212> TYPE: DNA
<213> ORGANISM: Artificial Sequence
<220> FEATURE:
<223> OTHER INFORMATION: Synthetic Construct

<400> SEQUENCE: 421
aaaacccatt catt 14

<210> SEQ ID NO 422
<211> LENGTH: 24
<212> TYPE: DNA
<213> ORGANISM: Artificial Sequence
<220> FEATURE:
<223> OTHER INFORMATION: Synthetic Construct

<400> SEQUENCE: 422
gtttcgtttt tttttttgg aagg 24

<210> SEQ ID NO 423
<211> LENGTH: 14
<212> TYPE: DNA
<213> ORGANISM: Artificial Sequence
<220> FEATURE:
<223> OTHER INFORMATION: Synthetic Construct

<400> SEQUENCE: 423
ttttacgttc ggcg 14

<210> SEQ ID NO 424
<211> LENGTH: 14
<212> TYPE: DNA
<213> ORGANISM: Artificial Sequence
<220> FEATURE:
<223> OTHER INFORMATION: Synthetic Construct

<400> SEQUENCE: 424
tttacgttcg gcgt 14

<210> SEQ ID NO 425
<211> LENGTH: 14
<212> TYPE: DNA
<213> ORGANISM: Artificial Sequence
<220> FEATURE:

<223> OTHER INFORMATION: Synthetic Construct

<400> SEQUENCE: 425
ttacgttcgg cgtg 14

<210> SEQ ID NO 426
<211> LENGTH: 14
<212> TYPE: DNA
<213> ORGANISM: Artificial Sequence
<220> FEATURE:
<223> OTHER INFORMATION: Synthetic Construct

<400> SEQUENCE: 426
tacgttcggc gtgg 14

<210> SEQ ID NO 427
<211> LENGTH: 14
<212> TYPE: DNA
<213> ORGANISM: Artificial Sequence
<220> FEATURE:
<223> OTHER INFORMATION: Synthetic Construct

<400> SEQUENCE: 427
acgttcggcg tggt 14

<210> SEQ ID NO 428
<211> LENGTH: 14
<212> TYPE: DNA
<213> ORGANISM: Artificial Sequence
<220> FEATURE:
<223> OTHER INFORMATION: Synthetic Construct

<400> SEQUENCE: 428
cgttcggcgt ggtt 14

<210> SEQ ID NO 429
<211> LENGTH: 14
<212> TYPE: DNA
<213> ORGANISM: Artificial Sequence
<220> FEATURE:
<223> OTHER INFORMATION: Synthetic Construct

<400> SEQUENCE: 429
gttcggcgtg gttt 14

<210> SEQ ID NO 430
<211> LENGTH: 14
<212> TYPE: DNA
<213> ORGANISM: Artificial Sequence
<220> FEATURE:
<223> OTHER INFORMATION: Synthetic Construct

<400> SEQUENCE: 430
ttcggcgtgg tttc 14

<210> SEQ ID NO 431
<211> LENGTH: 14
<212> TYPE: DNA
<213> ORGANISM: Artificial Sequence
<220> FEATURE:
<223> OTHER INFORMATION: Synthetic Construct

<400> SEQUENCE: 431
tcggcgtggt ttcg 14

<210> SEQ ID NO 432
<211> LENGTH: 14
<212> TYPE: DNA
<213> ORGANISM: Artificial Sequence
<220> FEATURE:
<223> OTHER INFORMATION: Synthetic Construct

<400> SEQUENCE: 432
cggcgtggtt tcgt 14

<210> SEQ ID NO 433
<211> LENGTH: 14
<212> TYPE: DNA
<213> ORGANISM: Artificial Sequence
<220> FEATURE:
<223> OTHER INFORMATION: Synthetic Construct

<400> SEQUENCE: 433
ggcgtggttt cgtc 14

<210> SEQ ID NO 434
<211> LENGTH: 14
<212> TYPE: DNA
<213> ORGANISM: Artificial Sequence
<220> FEATURE:
<223> OTHER INFORMATION: Synthetic Construct

<400> SEQUENCE: 434
gcgtggtttc gtcg 14

<210> SEQ ID NO 435
<211> LENGTH: 14
<212> TYPE: DNA
<213> ORGANISM: Artificial Sequence
<220> FEATURE:
<223> OTHER INFORMATION: Synthetic Construct

<400> SEQUENCE: 435
cgtggtttcg tcgt 14

<210> SEQ ID NO 436
<211> LENGTH: 14
<212> TYPE: DNA
<213> ORGANISM: Artificial Sequence
<220> FEATURE:
<223> OTHER INFORMATION: Synthetic Construct

<400> SEQUENCE: 436
gtggtttcgt cgtc 14

<210> SEQ ID NO 437
<211> LENGTH: 14
<212> TYPE: DNA
<213> ORGANISM: Artificial Sequence
<220> FEATURE:
<223> OTHER INFORMATION: Synthetic Construct

<400> SEQUENCE: 437
tggtttcgtc gtcg 14

<210> SEQ ID NO 438
<211> LENGTH: 14
<212> TYPE: DNA
<213> ORGANISM: Artificial Sequence
<220> FEATURE:
<223> OTHER INFORMATION: Synthetic Construct

<400> SEQUENCE: 438
ggtttcgtcg tcgt 14

<210> SEQ ID NO 439
<211> LENGTH: 14
<212> TYPE: DNA
<213> ORGANISM: Artificial Sequence
<220> FEATURE:
<223> OTHER INFORMATION: Synthetic Construct

<400> SEQUENCE: 439
gtttcgtcgt cgtt 14

<210> SEQ ID NO 440
<211> LENGTH: 14
<212> TYPE: DNA
<213> ORGANISM: Artificial Sequence
<220> FEATURE:
<223> OTHER INFORMATION: Synthetic Construct

<400> SEQUENCE: 440
tttcgtcgtc gttt 14

<210> SEQ ID NO 441
<211> LENGTH: 14
<212> TYPE: DNA
<213> ORGANISM: Artificial Sequence
<220> FEATURE:
<223> OTHER INFORMATION: Synthetic Construct

<400> SEQUENCE: 441
ttcgtcgtcg ttta 14

<210> SEQ ID NO 442
<211> LENGTH: 14
<212> TYPE: DNA
<213> ORGANISM: Artificial Sequence
<220> FEATURE:
<223> OTHER INFORMATION: Synthetic Construct

<400> SEQUENCE: 442
tcgtcgtcgt ttag 14

<210> SEQ ID NO 443
<211> LENGTH: 14
<212> TYPE: DNA
<213> ORGANISM: Artificial Sequence
<220> FEATURE:
<223> OTHER INFORMATION: Synthetic Construct

<400> SEQUENCE: 443
cgtcgtcgtt taga 14

<210> SEQ ID NO 444
<211> LENGTH: 14
<212> TYPE: DNA
<213> ORGANISM: Artificial Sequence
<220> FEATURE:
<223> OTHER INFORMATION: Synthetic Construct

<400> SEQUENCE: 444
gtcgtcgttt agat 14

<210> SEQ ID NO 445
<211> LENGTH: 14

<212> TYPE: DNA
<213> ORGANISM: Artificial Sequence
<220> FEATURE:
<223> OTHER INFORMATION: Synthetic Construct

<400> SEQUENCE: 445
tcgtcgttta gatt 14

<210> SEQ ID NO 446
<211> LENGTH: 14
<212> TYPE: DNA
<213> ORGANISM: Artificial Sequence
<220> FEATURE:
<223> OTHER INFORMATION: Synthetic Construct

<400> SEQUENCE: 446
cgtcgtttag attt 14

<210> SEQ ID NO 447
<211> LENGTH: 14
<212> TYPE: DNA
<213> ORGANISM: Artificial Sequence
<220> FEATURE:
<223> OTHER INFORMATION: Synthetic Construct

<400> SEQUENCE: 447
gtcgtttaga tttg 14

<210> SEQ ID NO 448
<211> LENGTH: 14
<212> TYPE: DNA
<213> ORGANISM: Artificial Sequence
<220> FEATURE:
<223> OTHER INFORMATION: Synthetic Construct

<400> SEQUENCE: 448
tcgtttagat ttga 14

<210> SEQ ID NO 449
<211> LENGTH: 14
<212> TYPE: DNA
<213> ORGANISM: Artificial Sequence
<220> FEATURE:
<223> OTHER INFORMATION: Synthetic Construct

<400> SEQUENCE: 449
cgtttagatt tgaa 14

<210> SEQ ID NO 450
<211> LENGTH: 14
<212> TYPE: DNA
<213> ORGANISM: Artificial Sequence
<220> FEATURE:
<223> OTHER INFORMATION: Synthetic Construct

<400> SEQUENCE: 450
gtttagattt gaag 14

<210> SEQ ID NO 451
<211> LENGTH: 14
<212> TYPE: DNA
<213> ORGANISM: Artificial Sequence
<220> FEATURE:
<223> OTHER INFORMATION: Synthetic Construct

<400> SEQUENCE: 451

-continued tttagatttg aagt 14

<210> SEQ ID NO 452
<211> LENGTH: 14
<212> TYPE: DNA
<213> ORGANISM: Artificial Sequence
<220> FEATURE:
<223> OTHER INFORMATION: Synthetic Construct

<400> SEQUENCE: 452
ttagatttga agtt 14

<210> SEQ ID NO 453
<211> LENGTH: 14
<212> TYPE: DNA
<213> ORGANISM: Artificial Sequence
<220> FEATURE:
<223> OTHER INFORMATION: Synthetic Construct

<400> SEQUENCE: 453
tagatttgaa gttc 14

<210> SEQ ID NO 454
<211> LENGTH: 14
<212> TYPE: DNA
<213> ORGANISM: Artificial Sequence
<220> FEATURE:
<223> OTHER INFORMATION: Synthetic Construct

<400> SEQUENCE: 454
agatttgaag ttcg 14

<210> SEQ ID NO 455
<211> LENGTH: 14
<212> TYPE: DNA
<213> ORGANISM: Artificial Sequence
<220> FEATURE:
<223> OTHER INFORMATION: Synthetic Construct

<400> SEQUENCE: 455
gatttgaagt tcgg 14

<210> SEQ ID NO 456
<211> LENGTH: 14
<212> TYPE: DNA
<213> ORGANISM: Artificial Sequence
<220> FEATURE:
<223> OTHER INFORMATION: Synthetic Construct

<400> SEQUENCE: 456
atttgaagtt cggt 14

<210> SEQ ID NO 457
<211> LENGTH: 14
<212> TYPE: DNA
<213> ORGANISM: Artificial Sequence
<220> FEATURE:
<223> OTHER INFORMATION: Synthetic Construct

<400> SEQUENCE: 457
tttgaagttc ggtt 14

<210> SEQ ID NO 458
<211> LENGTH: 14
<212> TYPE: DNA
<213> ORGANISM: Artificial Sequence -continued

```
<220> FEATURE:
<223> OTHER INFORMATION: Synthetic Construct

<400> SEQUENCE: 458

ttgaagttcg gttt                                                    14


<210> SEQ ID NO 459
<211> LENGTH: 23
<212> TYPE: DNA
<213> ORGANISM: Artificial Sequence
<220> FEATURE:
<223> OTHER INFORMATION: Synthetic Construct

<400> SEQUENCE: 459

aattaaggag atttttggcg atc                                          23


<210> SEQ ID NO 460
<211> LENGTH: 19
<212> TYPE: DNA
<213> ORGANISM: Artificial Sequence
<220> FEATURE:
<223> OTHER INFORMATION: Synthetic Construct

<400> SEQUENCE: 460

acgaacacac tcgaacacg                                               19


<210> SEQ ID NO 461
<211> LENGTH: 28
<212> TYPE: DNA
<213> ORGANISM: Artificial Sequence
<220> FEATURE:
<223> OTHER INFORMATION: Synthetic Construct

<400> SEQUENCE: 461

atcgttttag tagtttttgt cgcgtgcg                                     28
```

DIAGNOSIS KIT AND CHIP FOR BLADDER CANCER USING BLADDER CANCER SPECIFIC METHYLATION MARKER GENE

CROSS-REFERENCE TO RELATED APPLICATIONS

This is a continuation-in-part application under 35 U.S.C. §120 of U.S. patent application Ser. No. 15/016,424 filed on Feb. 5, 2016, which in turn is a continuation-in-part application of U.S. patent application Ser. No. 13/627,474, now U.S. Pat. No. 9,365,900, filed on Sep. 26, 2012, which in turn is a divisional application of U.S. patent application Ser. No. 12/744,491 filed on Jun. 24, 2010, now abandoned, entitled "DIAGNOSIS KIT AND CHIP FOR BLADDER CANCER USING BLADDER CANCER SPECIFIC METHYLATION MARKER GENE" in the name of Sung Wan AN, et al, which is a U.S. national stage application under the provisions of 35 U.S.C. §371 of International Patent Application No. PCT/KR2008/007081 filed on Dec. 1, 2008, which claims priority of Korean Patent Application No. 10-2007-0124015 filed on Nov. 30, 2007, all of which are hereby incorporated by reference herein in their entireties.

SEQUENCE LISTING

The instant application contains a Sequence Listing which has been submitted in ASCII format via EFS-Web and is hereby incorporated by reference in its entirety. Said ASCII copy, created on May 3, 2017, is named 322DIV2CIP3_SeqID_ST25_REV.txt and is 112,806 bytes in size.

TECHNICAL FIELD

The present invention relates to a kit and nucleic acid chip for diagnosing bladder cancer using a bladder cancer-specific marker gene, and more particularly to a kit and nucleic acid chip for diagnosing bladder cancer, which can detect the promoter methylation of a bladder cancer-specific gene, the promoter region of which is methylated specifically in transformed cells of bladder cancer.

BACKGROUND ART

Bladder cancer is the most frequent cancer of the urinary system and was found to be caused by many factors. It is known that bladder cancer is mainly caused by smoking or various chemical substances (paints for leather, air pollutants, artificial sweetening agents, nitrates and the like) which irritate the bladder wall while they are excreted as urine after being absorbed in vivo.

As conventional methods for diagnosing bladder cancer, a method of finding abnormal cells in urine is used, but has low accuracy. Also, cystoscopy comprising inserting a catheter into the bladder and collecting suspected tissue from the bladder is an invasive method having relatively high accuracy.

Generally, when bladder cancer is diagnosed at an early stage, the survival rate of bladder cancer patients is increased, but it is not easy to diagnose bladder cancer at an early stage. As a method for diagnosing bladder cancer, a method of incising part of the body is currently being used, but it has difficulty in diagnosing bladder cancer at an early stage.

Bladder cancers are classified, according to invasion into the muscular layer of the bladder, into superficial cancer and invasive cancer. Generally, about 30% of patients upon diagnosis of bladder cancer are invasive bladder cancer patients. Thus, in order to increase the survival period of patients, it is the best method to diagnose bladder cancer at early stage when the bladder cancer lesions are small. Accordingly, there is an urgent need to development a diagnostic method more efficient than various prior diagnostic methods for bladder cancer, that is, a bladder cancer-specific biomarker which allows early diagnosis of bladder cancer, can treat a large amount of samples and has high sensitivity and specificity.

Recently, methods of diagnosing cancer through the measurement of DNA methylation have been suggested. DNA methylation occurs mainly on the cytosine of CpG islands in the promoter region of a specific gene to interfere with the binding of transcription factors, thus silencing the expression of the gene. Thus, detecting the methylation of CpG islands in the promoter of tumor inhibitory genes greatly assists in cancer research. Recently, an attempt has been actively made to determine promoter methylation, by methods such as methylation-specific PCR (hereinafter referred to as MSP) or automatic DNA sequencing, for the diagnosis and screening of cancer.

Although there are disputes on whether the methylation of promoter CpG islands directly induces cancer development or causes a secondary change after cancer development, it has been found that tumor suppressor genes, DNA repair genes, cell cycle regulatory genes and the line in several cancers are hyper-methylated, and thus the expression of these genes are silenced. Particularly, it is known that the hyper-methylation of the promoter region of a specific gene occurs at an early stage of cancer development.

Thus, the methylation of the promoter methylation of tumor-associated genes is an important indication of cancer and can be used in many applications, including the diagnosis and early diagnosis of cancer, the prediction of cancer development, the prediction of prognosis of cancer, follow-up examination after treatment, and the prediction of responses to anticancer therapy. Recently, an actual attempt to examine the promoter methylation of tumor-associated genes in blood, sputum, saliva, feces and to use the examined results for diagnosis and treatment of various cancers has been actively made (Esteller, M. et al., *Cancer Res.,* 59:67, 1999; Sanchez-Cespedez, M. et al., *Cancer Res.,* 60:892, 2000; Ahlquist, D. A. et al., *Gastroenterol.,* 119: 1219, 2000).

Accordingly, the present inventors have made many efforts to develop a diagnostic kit capable of effectively diagnosing bladder cancer and, as a result, have found that bladder cancer can be diagnosed by measuring the methylation degree using as a biomarker the promoter of methylation-associated genes which are expressed specifically in bladder cancer cells, thereby completing the present invention.

SUMMARY OF INVENTION

It is, therefore, an object of the present invention to provide a kit for diagnosing bladder cancer, which comprises the methylated promoter or exon region of a bladder cancer marker gene.

Another object of the present invention is to provide a nucleic acid chip for diagnosing bladder cancer, which comprises a probe capable of hybridizing with a fragment containing the CpG island of the bladder cancer-specific marker gene.

Still another object of the present invention is to provide a method for measuring the methylation of the promoter or exon region of a gene originated from a clinical sample.

To achieve the above objects, the present invention provides a kit for diagnosing bladder cancer, which comprises the methylated promoter or exon region of a bladder cancer marker gene selected from the group consisting of: (1) CDX2 (NM_001265)—caudal type homeobox transcription factor 2; (2) CYP1B1 (NM_000104)—cytochrome P450, family 1, subfamily B, polypeptide 1; (3) VSX1 (NM_199425)—visual system homeobox 1 homolog, CHX10-like (zebrafish); (4) HOXA11 (NM_005523)—homeobox A11; (5) T (NM_003181)—T, brachyury homolog (mouse); (6) TBX5 (NM_080717)—T-box 5; (7) PENK (NM_006211)—proenkephalin; (8) PAQR9 (NM_198504)—progestin and adipoQ receptor family member IV; (9) LHX2 (NM_004789)—LIM Homeobox 2; and (10) SIM2 (U80456)—single-minded homog 2 (*Drosophila*).

The present invention also provides a nucleic acid chip for diagnosing bladder cancer, which comprises a probe capable of hybridizing with a fragment containing the CpG island of the promoter or exon region of the bladder cancer marker gene selected from the group consisting of: (1) CDX2 (NM_001265)—caudal type homeobox transcription factor 2; (2) CYP1B1 (NM_000104)—cytochrome P450, family 1, subfamily B, polypeptide 1; (3) VSX1 (NM_199425)—visual system homeobox 1 homolog, CHX10-like (zebrafish); (4) HOXA11 (NM_005523)—homeobox A11; (5) T (NM_003181)—T, brachyury homolog (mouse); (6) TBX5 (NM_080717)—T-box 5; (7) PENK (NM_006211)—proenkephalin; (8) PAQR9 (NM_198504)—progestin and adipoQ receptor family member IV; (9) LHX2 (NM_004789)—LIM Homeobox 2; and (10) SIM2 (U80456)—single-minded homog 2 (*Drosophila*).

The present invention also provides a method for detecting the methylation of the promoter or exon region of a clinical sample-originated gene selected from the group consisting of CDX2, CYP1B1, VSX1, HOXA11, T, TBX5, PENK, PAQR9, LHX2 and SIM2.

Other features and embodiments of the present invention will be more apparent from the following detailed description and the appended claims.

BRIEF DESCRIPTION OF DRAWINGS

FIG. 3A shows measurement results for the methylation degrees of the CDX2, the CYP1B1 and the T biomarker genes in the urinary cells of normal persons, Cystitis patients, hematuria patients and bladder cancer patients.

FIG. 3B shows measurement results for the methylation degrees of the TBX5, the LHX2 and the SIM2 biomarker genes in the urinary cells of normal persons, Cystitis patients, hematuria patients and bladder cancer patients.

FIG. 3C shows measurement results for the methylation degrees of the VSX1, the HOXA11 and the PENK biomarker genes in the urinary cells of normal persons, Cystitis patients, hematuria patients and bladder cancer patients.

FIG. 3D shows measurement results for the methylation degrees of the PAQR9 biomarker genes in the urinary cells of normal persons, Cystitis patients, hematuria patients and bladder cancer patients.

DETAILED DESCRIPTION OF THE INVENTION, AND PREFERRED EMBODIMENTS

Figure 1:
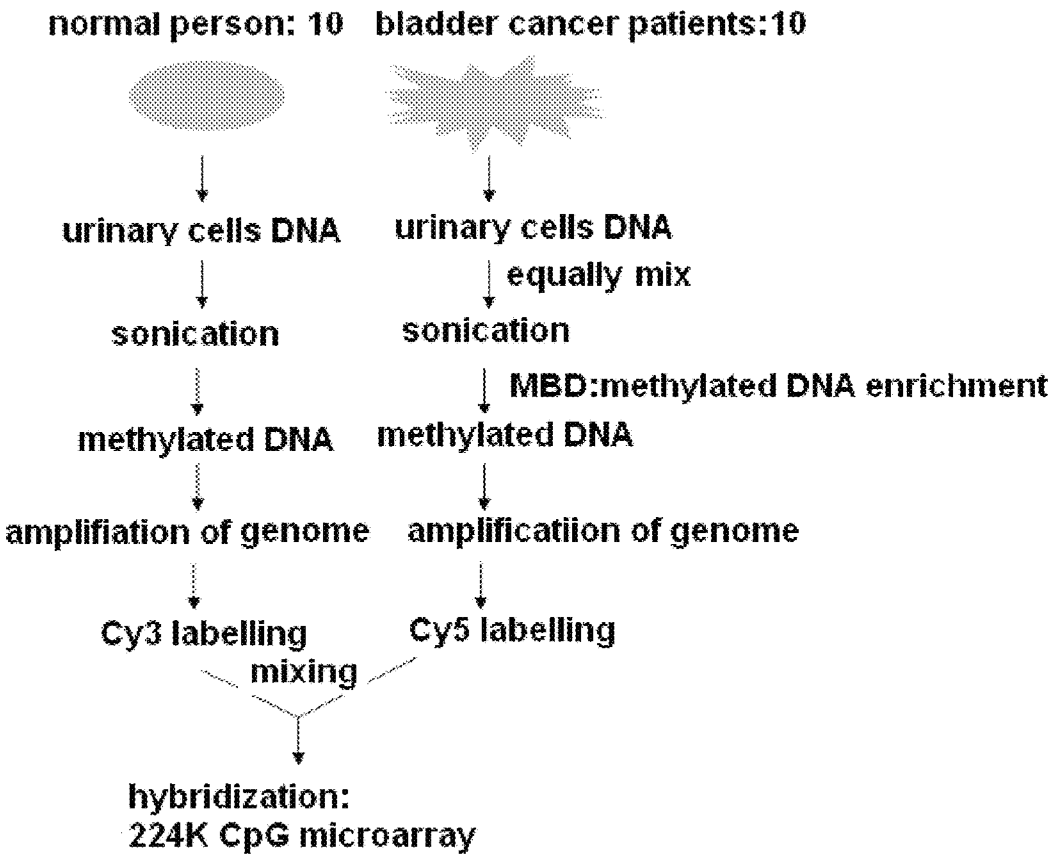
FIG. 1 is a schematic diagram showing a process of discovering a methylated biomarker for diagnosis of bladder cancer from the urinary cells of normal persons and bladder cancer patients through CpG micrroarray analysis.

In one aspect, the present invention relates to a kit for diagnosing bladder cancer, which comprises the methylated promoter or exon region of a bladder cancer marker gene.

In another aspect, the present invention relates to a nucleic acid chip for diagnosing bladder cancer, which comprises a probe capable of hybridizing with a fragment containing the CpG island of the promoter or exon region of a bladder cancer marker gene.

In the present invention, the promoter or exon region may contain at least one methylated CpG dinucleotide. Also, the promoter or exon region is any one of DNA sequences represented in SEQ ID NO: 31 to SEQ ID NO: 40.

In the present invention, the probe preferably has a size ranging from 10 bp to 1 kb, and has a homology with a base sequence containing the CpG island of the promoter or exon region of a bladder cancer marker gene, such that it can hybridize with the base sequence. More preferably, the probe has a size of 10-100 bp, and has a homology with a base sequence containing the CpG island of the promoter or exon region of a bladder cancer marker gene, such that it can hybridize with the base sequence in strict conditions. If the size of the probe is less than 10 bp, non-specific hybridization will occur, and if it is more than 1 kb, the binding between the probes will occur, thus making it difficult to read hybridization results.

A method for screening a methylation marker gene according to the present invention comprises the steps of: (a) isolating genomic DNAs from transformed cells and non-transformed cells; (b) reacting the isolated genomic DNAs to with a protein binding to methylated DNA and isolating methylated DNAs from the genomic DNAs; and (c) amplifying the isolated methylated DNAs, hybridizing the amplified DNAs to CpG microarrays, and selecting a methylation marker gene showing the greatest difference in methylation degree between normal cells and cancer cells among from the hybridized genes.

By the method for screening the methylation biomarker gene, it is possible to screen various genes, which are methylated not only in bladder cancer, but also in various dysplasic stages which progress to bladder cancer. The screened genes are also useful for blood cancer screening, risk assessment, prognosis, disease identification, disease staging, and selection of therapeutic targets.

The identification of the methylated gene in bladder cancer and abnormalities at various stages enables early diagnosis of bladder cancer in an accurate and effective manner, and allows establishment of methylation data using multiple genes and identification of new therapeutic targets. Additionally, methylation data according to the present invention enables establishment of a more accurate system for diagnosing bladder cancer, when it is used together with a method for detecting other non-methylation-associated biomarkers.

The inventive method enables diagnosis of bladder cancer progression at various stages by determining the methylation stage of at least one nucleic acid biomarker obtained from a sample. When the methylation stage of nucleic acid isolated from a sample at each stage of bladder cancer is compared with the methylation stage of at least one nucleic acid obtained from a sample having no abnormality in the cell proliferation of bladder tissue, a certain stage of bladder cancer in the sample can be determined. The methylation stage may be hypermethylation.

In one embodiment of the present invention, nucleic acid can be methylated in the regulatory region of a gene. In another embodiment, since methylation begins from the outer boundary of the regulatory region of a gene and then spreads inward, detection of methylation at the outer boundary of the regulatory region enables early diagnosis of genes which are involved in cell transformation.

In still another embodiment of the present invention, the cell growth abnormality (dysplasia) of bladder tissue can be diagnosed by detecting the methylation of at least one nucleic acid of the following nucleic acids using a kit or a nucleic acid chip: CDX2 (NM_001265, caudal type homeobox transcription factor 2); CYP1B1 (NM_000104, cytochrome P450, family 1, subfamily B, polypeptide 1); VSX1 (NM_199425, visual system homeobox 1 homolog, CHX10-like (zebrafish)); HOXA11 (NM_005523, homeobox A11); T (NM_003181, T, brachyury homolog (mouse)); TBX5 (NM_080717, T-box 5); PENK (NM_006211, proenkephalin); and PAQR9 (NM_198504, progestin and adipoQ receptor family member IV); LHX2 (NM_004789) LIM Homeobox 2; SIM2 (U80456), single-minded homog 2 (*Drosophila*) gene and combination thereof.

The use of the diagnostic kit or nucleic acid chip of the present invention can determine the cell growth abnormality of bladder tissue in a sample. The method for determining the cell growth abnormality of bladder tissue comprises determining the methylation of at least one nucleic acid isolated from a sample. In the method, the methylation stage of at least one nucleic acid is compared with the methylation stage of a nucleic acid isolated from a sample having no cell growth abnormality (dysplasia).

The examples of said nucleic acid are follows: CDX2 (NM_001265, caudal type homeobox transcription factor 2); CYP1B1 (NM_000104, cytochrome P450, family 1, subfamily B, polypeptide 1); VSX1 (NM_199425, visual system homeobox 1 homolog, CHX10-like (zebrafish)); HOXA11 (NM_005523, homeobox A11); T (NM_003181, T, brachyury homolog (mouse)); TBX5 (NM_080717, T-box 5); PENK (NM_006211, proenkephalin); and PAQR9 (NM_198504, progestin and adipoQ receptor family member IV); LHX2 (NM_004789) LIM Homeobox 2; SIM2 (U80456), single-minded homog 2 (*Drosophila*) gene and combination thereof.

In still another embodiment of the present invention, cells capable of forming bladder cancer can be diagnosed at an early stage using the methylation gene marker. When genes confirmed to be methylated in cancer cells are methylated in cells which seem to be normal clinically or morphologically, the cells that seem to be normal are cells, the carcinogenesis of which is in progress. Thus, bladder cancer can be diagnosed at an early stage by detecting the methylation of bladder cancer-specific genes in the cells that seem to be normal.

The use of the methylation marker gene of the present invention enables detection of the cell growth abnormality (dysplasia progression) of bladder tissue in a sample. The method for detecting the cell growth abnormality (dysplasia progression) of bladder tissue comprises bringing at least one nucleic acid isolated from a sample into contact with an agent capable of determining the methylation status of the nucleic acid. The method comprises determining the methylation status of at least one region in at least one nucleic acid, and the methylation status of the nucleic acid differs from the methylation status of the same region in a nucleic acid isolated from a sample having no cell growth abnormality (dysplasia progression) of bladder tissue.

In still another embodiment of the present invention, transformed bladder cancer cells can be detected by examining the methylation of a marker gene using the above-described kit or nucleic acid chip.

In still another embodiment of the present invention, bladder cancer can be diagnosed by examining the methylation of a marker gene using the above-described kit or nucleic acid chip.

In still another embodiment of the present invention, the likelihood of progression to bladder cancer can be diagnosed by examining the methylation of a marker gene with the above-described kit or nucleic acid chip in a sample showing a normal phenotype. The sample may be solid or liquid tissue, cell, urine, serum or plasma.

In still another aspect, the present invention relates to a method for detecting the promoter methylation of a clinical sample-originated gene.

In the present invention, the method for measuring the promoter methylation of a clinical sample-originated gene may be selected from the group consisting of PCR, methylation specific PCR, real-time methylation specific PCR, PCR using a methylated DNA-specific binding protein, quantitative PCR, pyrosequencing and bisulfite sequencing, and the clinical sample is preferably a tissue, cell, blood or urine originated from patients suspected of cancer or subjects to be diagnosed.

In the present invention, the method for detecting the promoter methylation of the gene comprises the steps of: (a) isolating a sample DNA from a clinical sample; (b) amplifying the isolated DNA with primers capable of amplifying a fragment containing the promoter CpG island of a gene selected from the group consisting of CDX2, CYP1B1, VSX1, HOXA11, T, TBX5, PENK, PAQR9, LHX2 and SIM2; and (c) determining the promoter methylation of the DNA on the basis of whether the DNA has been amplified or not in step (b).

In an embodiment of the present disclosure, primer(s) that could amplify a methylated CpG of SIM2 might be used, and such primer(s) comprises at least one or more CpG dinucleotide in a region which hybridizes to the methylated CpG of SIM2 Specifically, the primer(s) for amplifying a methylated CpG of SIM2 comprise sequence(s) having a homology of 50% or more with sequence(s) selected from the group consisting of SEQ ID NOs: 43-44, 46-63, 65-126, 128-189, 191-232, 234-295, 297-358, 360-421, and 423-460. Preferably, the primer(s) for amplifying a methylated CpG of SIM2 comprise sequence(s) having a homology of at least 60%, 70%, 80%, 90%, 91%, 92%, 93%, 94%, 95%, 96%, 97%, 98%, 99% and 100% with sequence(s) selected from the group consisting of SEQ ID NOs: 43-44, 46-63, 65-126, 128-189, 191-232, 234-295, 297-358, 360-421, and 423-460.

If required, probe(s) capable of hybridizing with a methylated CpG of SIM2 might be used. The probe(s) capable of hybridizing with a methylated CpG of SIM2 comprise at least one or more CpG dinucleotide in a region which hybridizes to the methylated CpG of SIM2. Specifically, probe(s) might comprise sequence(s) having a homology of 50% or more with sequence(s) selected from the group consisting of SEQ ID NOs: 45, 64, 127, 190, 233, 296, 359, 422 and 461. Preferably, the probe(s) capable of hybridizing with a methylated CpG of SIM2 comprise sequence(s) having a homology of at least 60%, 70%, 80%, 90%, 91%, 92%, 93%, 94%, 95%, 96%, 97%, 98%, 99% and 100% with sequence(s) selected from the group consisting of SEQ ID NOs: 45, 64, 127, 190, 233, 296, 359, 422 and 461.

In another embodiment of the present invention, the likelihood of development of tissue to bladder cancer can be evaluated by examining the methylation frequency of a gene which is methylated specifically in bladder cancer and determining the methylation frequency of tissue having the likelihood of progression to bladder cancer.

As used herein, "cell conversion" refers to the change in characteristics of a cell from one form to another such as from normal to abnormal, non-tumorous to tumorous, undifferentiated to differentiated, stem cell to non-stem cell. Further, the conversion may be recognized by morphology of the cell, phenotype of the cell, biochemical characteristics and so on.

As used herein, the term "early diagnosis" of cancer refers to discovering the likelihood of cancer before metastasis. Preferably, it refers to discovering the likelihood of cancer before a morphological change in a sample tissue or cell is observed. Additionally, the term "early diagnosis" of transformation the high probability of a cell to undergo transformation in its early stages before the cell is morphologically designated as being transformed.

As used herein, the term "hypermethylation" refers to the methylation of CpG islands.

As used herein, the term "sample" or "biological sample" is referred to in its broadest sense, and includes any biological sample obtained from an individual, body fluid, cell line, tissue culture or other sources, according to the type of analysis that is to be performed. Methods of obtaining body fluid and tissue biopsy from mammals are generally widely known. A preferred source is bladder biopsy.

Screening for Methylation Regulated Biomarkers

The present invention is directed to a method of determining biomarker genes that are methylated when the cell or tissue is converted or changed from one type of cell to another. As used herein, "converted" cell refers to the change in characteristics of a cell or tissue from one form to another such as from normal to abnormal, non-tumorous to tumorous, undifferentiated to differentiated and so on.

In one Example of the present invention, urinary cells were isolated from the urine of normal persons and bladder cancer patients, and then genomic DNAs were isolated from the urinary cells. In order to obtain only methylated DNAs from the genomic DNAs, the genomic DNAs were allowed to react with McrBt binding to methylated DNA, and then methylated DNAs binding to the McrBt protein were isolated. The isolated methylated DNAs binding to the McrBt protein were amplified, and then the DNAs originated from the normal persons were labeled with Cy3, and the DNAs originated from the bladder cancer patients were labeled with Cy5. Then, the DNAs were hybridized to human CpG-island microarrays, and 10 genes showing the greatest difference in methylation degree between the normal persons and the bladder cancer patients were selected as biomarkers.

In the present invention, in order to further confirm whether the 10 biomarkers have been methylated, pyrosequencing was performed.

Specifically, total genomic DNA was isolated from the bladder cell lines RT-4, J82, HT1197 and HT1376 and treated with bisulfite. The genomic DNA converted with bisulfite was amplified. Then, the amplified PCR product was subjected to pyrosequencing in order to measure the methylation degree of the genes. As a result, it could be seen that the 10 biomarkers were all methylated.

Biomarker for Bladder Cancer

The present invention provides a biomarker for diagnosing bladder cancer.

Biomarkers for Bladder Cancer—Using Cancer Cells for Comparison with Normal Cells In one embodiment of the present invention, it is understood that "normal" cells are those that do not show any abnormal morphological or cytological changes. "Tumor" cells mean cancer cells. "Non-tumor" cells are those cells that were part of the diseased tissue but were not considered to be the tumor portion.

In one aspect, the present invention is based on the relationship between bladder cancer and the hypermethylation of the promoter or exon region of the following 10 genes: CDX2 (NM_001265, caudal type homeobox transcription factor 2); CYP1B1 (NM_000104, cytochrome P450, family 1, subfamily B, polypeptide 1); VSX1 (NM_199425, visual system homeobox 1 homolog, CHX10-like (zebrafish)); HOXA11 (NM_005523, homeobox A11); T (NM_003181, T, brachyury homolog (mouse)); TBX5 (NM_080717, T-box 5); PENK (NM_006211, proenkephalin); and PAQR9 (NM_198504, progestin and adipoQ receptor family member IV); LHX2 (NM_004789)—LIM Homeobox 2; and SIM2 (U80456)—single-minded homolog 2 (*Drosophila*); gene.

With other applications of the diagnostic kit or nucleic acid chip of the present invention, the invention can diagnose a cellular proliferative disorder of bladder tissue in a subject by determining the state of methylation of one or more nucleic acids isolated from the subject, wherein the state of methylation of one or more nucleic acids as compared with the state of methylation of one or more nucleic acids from a subject not having the cellular proliferative disorder of bladder tissue is indicative of a cellular proliferative disorder of bladder tissue in the subject. A preferred nucleic acid is a CpG-containing nucleic acid, such as a CpG island.

With other applications of the diagnostic kit or nucleic acid chip of the present invention, the cell growth abnormality of bladder tissue in a subject can be diagnosed comprising determining the methylation of one or more nucleic acids isolated from the subject. Said nucleic acid is preferably encoding the followings: CDX2 (NM_001265, caudal type homeobox transcription factor 2); CYP1B1 (NM_000104, cytochrome P450, family 1, subfamily B, polypeptide 1); VSX1 (NM_199425, visual system homeobox 1 homolog, CHX10-like (zebrafish)); HOXA11 (NM_005523, homeobox A11); T (NM_003181, T, brachyury homolog (mouse)); TBX5 (NM_080717, T-box 5); PENK (NM_006211, proenkephalin); and PAQR9 (NM_198504, progestin and adipoQ receptor family member IV); LHX2 (NM_004789)—LIM Homeobox 2; and SIM2 (U80456)—single-minded homolog 2 (*Drosophila*); gene and combinations thereof. The state of methylation of one or more nucleic acids as compared with the state of methylation of said nucleic acid from a subject not having a predisposition to the cellular proliferative disorder of bladder tissue is indicative of a cell proliferative disorder of bladder tissue in the subject.

As used herein, "predisposition" refers to an increased likelihood that an individual will have a disorder. Although a subject with a predisposition does not yet have the disorder, there exists an increased propensity to the disease.

Another embodiment of the invention provides a method for diagnosing a cellular proliferative disorder of bladder tissue in a subject comprising contacting a nucleic acid-containing specimen from the subject with an agent that provides a determination of the methylation state of nucleic acids in the specimen, and identifying the methylation state of at least one region of at least one nucleic acid, wherein the methylation state of at least one region of at least one nucleic acid that is different from the methylation state of the same region of the same nucleic acid in a subject not having the cellular proliferative disorder is indicative of a cellular proliferative disorder of bladder tissue in the subject.

The inventive method includes determining the state of methylation of one or more regions of one or more nucleic acids isolated from the subject. The phrases "nucleic acid" or "nucleic acid sequence" as used herein refer to an oligonucleotide, nucleotide, polynucleotide, or to a fragment of any of these, to DNA or RNA of genomic or synthetic origin which may be single-stranded or double-stranded, to DNA or RNA of genomic or synthetic origin which may represent a sense or antisense strand, peptide nucleic acid (PNA), or to any DNA-like or RNA-like material of natural or synthetic origin. As will be understood by those of skill in the art, when the nucleic acid is RNA, the deoxynucleotides A, G, C, and T are replaced by ribonucleotides A, G, C, and U, respectively.

The nucleic acid of interest can be any nucleic acid where it is desirable to detect the presence of a differentially methylated CpG island. The CpG island is a CpG rich region of a nucleic acid sequence.

Methylation

Any nucleic acid sample, in purified or nonpurified form, can be utilized in accordance with the present invention, provided it contains or is suspected of containing, a nucleic acid sequence containing a target locus (e.g., CpG-containing nucleic acid). One nucleic acid region capable of being differentially methylated is a CpG island, a sequence of nucleic acid with an increased density relative to other nucleic acid regions of the dinucleotide CpG. The CpG doublet occurs in vertebrate DNA at only about 20% of the frequency that would be expected from the proportion of G*C base pairs. In certain regions, the density of CpG doublets reaches the predicted value; it is increased by ten fold relative to the rest of the genome. CpG islands have an average G*C content of about 60%, and general DNA have an average G*C contents of about 40%. The islands take the form of stretches of DNA typically about one to two kilobases long. There are about 45,000 such islands in the human genome.

In many genes, the CpG islands begin just upstream of a promoter and extend downstream into the transcribed region. Methylation of a CpG island at a promoter usually prevents expression of the gene. The islands can also surround the 5' region of the coding region of the gene as well as the 3' region of the coding region. Thus, CpG islands can be found in multiple regions of a nucleic acid sequence including upstream of coding sequences in a regulatory region including a promoter region, in the coding regions (e.g., exons), in downstream of coding regions, for example, enhancer regions, and in introns.

In general, the CpG-containing nucleic acid is DNA. However, invention methods may employ, for example, samples that contain DNA, or DNA and RNA, including messenger RNA, wherein DNA or RNA may be single stranded or double stranded, or a DNA-RNA hybrid may be included in the sample.

A mixture of nucleic acids may also be employed. The specific nucleic acid sequence to be detected may be a fraction of a larger molecule or can be present initially as a discrete molecule, so that the specific sequence constitutes the entire nucleic acid. It is not necessary that the nucleic acid sequence is present initially in a pure form, the nucleic acid may be a minor fraction of a complex mixture, such as contained in whole human DNA. The nucleic acid-containing sample used for determination of the state of methylation of nucleic acids contained in the sample or detection of methylated CpG islands may be extracted by a variety of techniques such as that described by Sambrook, et al. (Molecular Cloning: A Laboratory Manual, Cold Spring Harbor, N.Y., 1989; incorporated in its entirety herein by reference).

A nucleic acid can contain a regulatory region which is a region of DNA that encodes information or controls transcription of the nucleic acid. Regulatory regions include at least one promoter. A "promoter" is a minimal sequence sufficient to direct transcription, to render promoter-dependent gene expression controllable for cell-type specific, tissue-specific, or inducible by external signals or agents. Promoters may be located in the 5' or 3' regions of the gene. Promoter regions, in whole or in part, of a number of nucleic acids can be examined for sites of CpG-island methylation. Moreover, it is generally recognized that methylation of the target gene promoter proceeds naturally from the outer boundary inward. Therefore, early stage of cell conversion can be detected by assaying for methylation in these outer areas of the promoter region.

Nucleic acids isolated from a subject are obtained in a biological specimen from the subject. If it is desired to detect bladder cancer or stages of bladder cancer progression, the nucleic acid may be isolated from bladder tissue by scraping or taking a biopsy. These specimens may be obtained by various medical procedures known to those of skill in the art.

In one aspect of the invention, the state of methylation in nucleic acids of the sample obtained from a subject is hypermethylation compared with the same regions of the nucleic acid in a subject not having the cellular proliferative disorder of bladder tissue. Hypermethylation, as used herein, is the presence of methylated alleles in one or more nucleic acids. Nucleic acids from a subject not having a cellular proliferative disorder of bladder tissues contain no detectable methylated alleles when the same nucleic acids are examined.

Sample

The present invention describes early diagnosis of bladder cancer and utilizes the methylation of bladder cancer-specific genes. The methylation of bladder cancer-specific genes also occurred in tissue near tumor sites. Therefore, in the method for early diagnosis of bladder cancer, the methylation of bladder cancer-specific genes can be detected by examining all samples including liquid or solid tissue. The samples include, but are not limited to, tissue, cell, urine, serum or plasma.

Individual Genes and Panel

It is understood that the present invention may be practiced using each gene separately as a diagnostic or prognostic marker, or a few marker genes combined into a panel display format so that several marker genes may be detected to increase reliability and efficiency. Further, any of the genes identified in the present application may be used individually or as a set of genes in any combination with any of the other genes that are recited in the application. Also, genes may be ranked and weighted according to their importance together with the number of genes that are methylated, and a level of likelihood of development to cancer can be assigned. Such algorithms are within the scope of the present invention.

Methylation Detection Methods

Methylation Specific PCR

When genomic DNA is treated with bisulfite, the methylated cytosine in the 5'-CpG'-3 region remains without changes, and unmethylated cytosine is changed to uracil. Thus, for a base sequence modified by bisulfite treatment, PCR primers corresponding to regions in which a 5'-CpG-3' base sequence is present were constructed. Herein, two kinds of primers corresponding to the methylated case and the unmethylated case were constructed. When genomic DNA is modified with bisulfite and then subjected to PCR using the two kinds of primers, in the case in which the DNA is methylated, a PCR product is made from the DNA in which the primers corresponding to the methylated base sequence are used. In contrast, in the case in which the gene is unmethylated, a PCR product is made from the DNA in which the primers corresponding to the unmethylated base sequence are used. The methylation of DNA can be qualitatively analyzed using agarose gel electrophoresis.

Real-time Methylation-specific PCR

Real-time methylation-specific PCR is a real-time measurement method modified from methylation-specific PCR, and comprises treating genomic DNA with bisulfite, designing PCR primers corresponding to the methylated case and performing real-time PCR using the primers. Herein, methods of detecting methylation include two methods: a method of performing detection using a TanMan probe complementary to the amplified base sequence, and a method of performing detection using Sybergreen. Thus, real-time methylation-specific PCR selectively quantitatively analyze only DNA. Herein, a standard curve was prepared using an in vitro methylated DNA sample, and for standardization, a gene having no 5'-CpG-3' sequence in the base sequence was also amplified as a negative control group and was quantitatively analyzed for the methylation degree.

Pyrosequencing

Pyrosequencing is a real-time sequencing method modified from a bisulfite sequencing method. In the same manner as bisulfite sequencing, genomic DNA was modified by bisulfite treatment, and then primers corresponding to a region having no 5'-CpG-3' base sequence were constructed. After the genomic DNA had been treated with bisulfite, it was amplified with the PCR primers, and then subjected to real-time sequence analysis using sequencing primers. The amounts of cytosine and thymine in the 5'-CpG-3' region were quantitatively analyzed, and the methylation degree was expressed as a methylation index.

PCR or Quantitative PCR Using Methylated DNA-specific Binding Protein and DNA Chip In a PCR or DNA chip method using a methylated DNA-specific binding protein, when a protein binding specifically only to methylated DNA is mixed with DNA, the protein binds specifically only to methylated DNA, and thus only methylated DNA can be isolated. In the present invention, genomic DNA was mixed with a methylated DNA-specific binding protein, and then only methylated DNA was selectively isolated. The isolated DNA was amplified using PCR primers corresponding to the promoter region thereof, and then the methylation of the DNA was measured by agarose gel electrophoresis.

In addition, the methylation of DNA can also be measured by a quantitative PCR method. Specifically, methylated DNA isolated using a methylated DNA-specific binding protein can be labeled with a fluorescent dye and hybridized to a DNA chip in which complementary probes are integrated, thus measuring the methylation of the DNA. Herein, the methylated DNA-specific binding protein is not limited to McrBt.

Detection of Differential Methylation-Methylation Sensitive Restriction Endonuclease Detection of differential methylation can be accomplished by contacting a nucleic acid sample with a methylation sensitive restriction endonuclease that cleaves only unmethylated CpG sites under conditions and for a time to allow cleavage of unmethylated nucleic acid.

In a separate reaction, the sample is further contacted with an isoschizomer of the methylation sensitive restriction endonuclease that cleaves both methylated and unmethylated CpG-sites under conditions and for a time to allow cleavage of methylated nucleic acid. Specific primers are added to the nucleic acid sample under conditions and for a time to allow nucleic acid amplification to occur by conventional methods. The presence of amplified product in the sample digested with methylation sensitive restriction endonuclease but absence of an amplified product in sample digested with an isoschizomer of the methylation sensitive restriction enzyme endonuclease that cleaves both methylated and unmethylated CpG-sites indicates that methylation has occurred at the nucleic acid region being assayed. However, lack of amplified product in the sample digested with methylation sensitive restriction endonuclease together with lack of an amplified product in the sample digested with an isoschizomer of the methylation sensitive restriction enzyme endonuclease that cleaves both methylated and unmethylated CpG-sites indicates that methylation has not occurred at the nucleic acid region being assayed.

As used herein, a "methylation sensitive restriction endonuclease" is a restriction endonuclease that includes CG as part of its recognition site and has altered activity when the C is methylated as compared to when the C is not methylated (e.g., Sma I). Non-limiting examples of methylation sensitive restriction endonucleases include MspI, HpaII, BssHII, BstUI and Nod. Such enzymes can be used alone or in combination. Other methylation sensitive restriction endonucleases such as SacII and EagI may be applied to the present invention, but are not limited to these enzymes.

An "isoschizomer" of a methylation sensitive restriction endonuclease is a restriction endonuclease that recognizes the same recognition site as a methylation sensitive restriction endonuclease but cleaves both methylated CGs and unmethylated CGs, such as for example, MspI.

Primers of the invention are designed to be "substantially" complementary to each strand of the locus to be amplified and include the appropriate G or C nucleotides as discussed above. This means that the primers must be sufficiently complementary to hybridize with their respective strands under conditions that allow the agent for polymerization to perform. Primers of the invention are employed in the amplification process, which is an enzymatic chain reaction that produces exponentially increasing quantities of target locus relative to the number of reaction steps involved (e.g., polymerase chain reaction (PCR)). Typically, one primer is complementary to the negative (−) strand of the locus (antisense primer) and the other is complementary to the positive (+) strand (sense primer). Annealing the primers to denatured nucleic acid followed by extension with an enzyme, such as the large fragment of DNA Polymerase I (Klenow) and nucleotides, results in newly synthesized+ and − strands containing the target locus sequence. Because these newly synthesized sequences are also templates, repeated cycles of denaturing, primer annealing, and extension results in exponential production of the region (i.e., the target locus sequence) defined by the primer. The product of the chain reaction is a discrete nucleic acid duplex with termini corresponding to the ends of the specific primers employed.

Preferably, the method of amplifying is by PCR, as described herein and as is commonly used by those of ordinary skill in the art. However, alternative methods of amplification have been described and can also be employed such as real time PCR or linear amplification using isothermal enzyme. Multiplex amplification reactions may also be used.

Detection of Differential Methylation-Bifulfite Sequencing Method

Another method for detecting a methylated CpG-containing nucleic acid includes contacting a nucleic acid-containing specimen with an agent that modifies unmethylated cytosine, amplifying the CpG-containing nucleic acid in the specimen by means of CpG-specific oligonucleotide primers, wherein the oligonucleotide primers distinguish between modified methylated and non-methylated nucleic acid and detecting the methylated nucleic acid. The amplification step is optional and although desirable, is not essential. The method relies on the PCR reaction itself to distinguish between modified (e.g., chemically modified) methylated and unmethylated DNA. Such methods are described in U.S. Pat. No. 5,786,146, the contents of which are incorporated herein in their entirety especially as they relate to the bisulfite sequencing method for detection of methylated nucleic acid.

Substrates

Once the target nucleic acid region is amplified, the nucleic acid can be hybridized to a known gene probe immobilized on a solid support to detect the presence of the nucleic acid sequence.

As used herein, "substrate," when used in reference to a substance, structure, surface or material, means a composition comprising a nonbiological, synthetic, nonliving, planar, spherical or flat surface that is not heretofore known to comprise a specific binding, hybridization or catalytic recognition site or a plurality of different recognition sites or a number of different recognition sites which exceeds the number of different molecular species comprising the surface, structure or material. The substrate may include, for example and without limitation, semiconductors, synthetic (organic) metals, synthetic semiconductors, insulators and dopants; metals, alloys, elements, compounds and minerals; synthetic, cleaved, etched, lithographed, printed, machined and microfabricated slides, devices, structures and surfaces; industrial polymers, plastics, membranes; silicon, silicates, glass, metals and ceramics; wood, paper, cardboard, cotton, wool, cloth, woven and nonwoven fibers, materials and fabrics.

Several types of membranes are known to one of skill in the art for adhesion of nucleic acid sequences. Specific non-limiting examples of these membranes include nitrocellulose or other membranes used for detection of gene expression such as polyvinylchloride, diazotized paper and other commercially available membranes such as GENESCREEN™, ZETAPROBE™ (Biorad), and NYTRAN™. Beads, glass, wafer and metal substrates are included. Methods for attaching nucleic acids to these objects are well known to one of skill in the art. Alternatively, screening can be done in liquid phase.

Hybridization Conditions

In nucleic acid hybridization reactions, the conditions used to achieve a particular level of stringency will vary, depending on the nature of the nucleic acids being hybridized. For example, the length, degree of homology, nucleotide sequence composition (e.g., GC/AT content), and nucleic acid type (e.g., RNA, DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically. In general, conditions of high stringency are used for the hybridization of the probe of interest.

Label

The probe of interest can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the probe, or will be able to ascertain such, using routine experimentation.

Kit

In accordance with the present invention, there is provided a kit useful for the detection of a cellular proliferative disorder in a subject. Kits according to the present invention include a carrier means compartmentalized to receive a sample therein, one or more containers comprising a first container containing a reagent which sensitively cleaves unmethylated cytosine, a second container containing primers for amplification of a CpG-containing nucleic acid, and a third container containing a means to detect the presence of cleaved or uncleaved nucleic acid. Primers contemplated for use in accordance with the invention include those set forth in SEQ ID NOS: 1-20, and any functional combination and fragments thereof.

In an embodiment of the present disclosure, primer(s) that could amplify a methylated CpG of SIM2 might be used, and such primer(s) comprises at least one or more CpG dinucleotide in a region which hybridizes to the methylated CpG of SIM2 Specifically, the primer(s) for amplifying a methylated CpG of SIM2 comprise sequence(s) having a homology of 50% or more with sequence(s) selected from the group consisting of SEQ ID NOs: 43-44, 46-63, 65-126, 128-189, 191-232, 234-295, 297-358, 360-421, and 423-460. Preferably, the primer(s) for amplifying a methylated CpG of SIM2 comprise sequence(s) having a homology of at least 60%, 70%, 80%, 90%, 91%, 92%, 93%, 94%, 95%, 96%, 97%, 98%, 99% and 100% with sequence(s) selected from the group consisting of SEQ ID NOs: 43-44, 46-63, 65-126, 128-189, 191-232, 234-295, 297-358, 360-421, and 423-460.

If required, probe(s) capable of hybridizing with a methylated CpG of SIM2 might be used. The probe(s) capable of hybridizing with a methylated CpG of SIM2 comprise at least one or more CpG dinucleotide in a region which hybridizes to the methylated CpG of SIM2. Specifically, probe(s) might comprise sequence(s) having a homology of 50% or more with sequence(s) selected from the group consisting of SEQ ID NOs: 45, 64, 127, 190, 233, 296, 359, 422 and 461. Preferably, the probe(s) capable of hybridizing with a methylated CpG of SIM2 comprise sequence(s) having a homology of at least 60%, 70%, 80%, 90%, 91%, 92%, 93%, 94%, 95%, 96%, 97%, 98%, 99% and 100% with sequence(s) selected from the group consisting of SEQ ID NOs: 45, 64, 127, 190, 233, 296, 359, 422 and 461.

Functional combination or fragment refers to its ability to be used as a primer to detect whether methylation has occurred on the region of the genome sought to be detected.

Carrier means are suited for containing one or more container means such as vials, tubes, and the like, each of the container means comprising one of the separate elements to be used in the method. In view of the description provided herein of invention methods, those of skill in the art can readily determine the apportionment of the necessary reagents among the container means. For example, one of the container means can comprise a container containing methylation sensitive restriction endonuclease. One or more container means can also be included comprising a primer complementary to the nucleic acid locus of interest. In addition, one or more container means can also be included containing an isoschizomer of the methylation sensitive restriction enzyme.

EXAMPLES

Hereinafter, the present invention will be described in further detail with reference to examples. It is to be understood, however, that these examples are for illustrative purposes only and are not to be construed to limit the scope of the present invention.

Example 1

Discovery of Bladder Cancer-specific Methylated Genes

In order to screen biomarkers which are methylated specifically in bladder cancer, about 20 ml of the urine of each of 10 bladder cancer patients and 10 normal persons was centrifuged in a centrifuge (Hanil Science Industrial Co., Ltd., Korea) at 4,200×g for 10 minutes to isolate urinary cells. The supernatant was discarded, and the cell precipitate was washed twice with 5 ml of PBS. Genomic DNA was isolated from the cell precipitate using the QIAamp DNA Mini kit (QIAGEN, USA). 500 ng of the isolated genomic DNA was sonicated (Vibra Cell, SONICS), thus constructing about 200-300-bp-genomic DNA fragments.

To obtain only methylated DNA from the genomic DNA, a methyl binding domain (MBD) known to bind to methylated DNA (Fraga et al., *Nucleic Acid Res.,* 31:1765-1774, 2003) was used. Specifically, 2 μg of 6×His-tagged MBD was pre-incubated with 500 ng of the genomic DNA of *E. coli* JM110 (No. 2638, Biological Resource Center, Korea Research Institute of Bioscience & Biotechnology), and then bound to Ni-NTA magnetic beads (Qiagen, USA). 500 ng of the sonicated genomic DNA isolated from the urinary cells of the normal persons and the bladder cancer patients was allowed to react with the beads in the presence of binding buffer solution (10 mM Tris-HCl (pH 7.5), 50 mM NaCl, 1 mM EDTA, 1 mM DTT, 3 mM $MgCl_2$, 0.1% Triton-X100, 5% glycerol, 25 mg/ml BSA) at 4° C. for 20 minutes. Then, the beads were washed three times with 500 μl of a binding buffer solution containing 700 mM NaCl, and then methylated DNA bound to the MBD was isolated using the QiaQuick PCR purification kit (QIAGEN, USA).

Then, the methylated DNAs bound to the MBD were amplified using a genomic DNA amplification kit (Sigma, USA, Cat. No. WGA2), and 4 μg of the amplified DNAs were labeled with Cy3 for the normal person-originated DNA and with Cy5 for the bladder cancer patient-originated DNA using the BioPrime Total Genomic Labeling system I (Invitrogen Corp., USA). The DNA of the normal persons and the DNA of the bladder patients were mixed with each other, and then hybridized to 244K human CpG microarrays (Agilent, USA) (FIG. 1). After the hybridization, the DNA mixture was subjected to a series of washing processes, and then scanned using an Agilent scanner. The calculation of signal values from the microarray images was performed by calculating the relative difference in signal strength between the normal person sample and the bladder cancer patient sample using Feature Extraction program v. 9.5.3.1 (Agilent).

In order to select unmethylated spots from the normal sample, the whole Cy3 signal values were averaged, and then spots having a signal value of less than 10% of the averaged value were regarded as those unmethylated in the samples of the normal persons. As a result, 41,674 spots having a Cy3 signal value of less than 65 were selected.

In order to select the methylated spots in the samples of the bladder cancer patients from among the 41,674 spots, spots having a Cy5 signal value of more than 130 were regarded as the methylated spots in bladder cancer. As a result, 631 spots having a Cy5 signal value of more than 130 were selected. From these spots, 227 genes corresponding to the promoter region were secured as bladder cancer-specific methylated genes.

From the genes, 10 genes (CDX2, CYP1B1, VSX16, HOXA11, T, TBX5, PENK, PAQR9, LHX2, and SIM2) showing the greatest relative difference between methylation degree of the normal persons and that of the bladder cancer patients were selected, and the presence of CpG islands in the promoter region of the 10 genes was confirmed using MethPrimer. The 10 genes were secured as methylation biomarkers for diagnosis of bladder cancer. The list of the 10 genes and the relative methylation degree thereof in the urinary cells of the bladder patients relative to those of the normal persons are shown in Table 1 below.

TABLE 1

| 10 methylation biomarkers for diagnosis of bladder cancer | | | |
|---|---|---|---|
| Biomarker for bladder cancer | GenBank No. | Description | Relative methylation [a] |
| CDX2 | NM_001265 | caudal type homeobox transcription factor 2 | 11.0 |
| CYP1B1 | NM_000104 | cytochrome P450, family 1, subfamily B, polypeptide 1 | 14.6 |
| VSX1 | NM_199425 | visual system homeobox 1 homolog, CHX10-like (zebrafish) | 33.4 |
| HOXA11 | NM_005523 | homeobox A11 | 14.2 |
| T | NM_003181 | T, brachyury homolog (mouse) | 51.4 |
| TBX5 | NM_080717 | T-box 5 | 18.7 |
| PENK | NM_006211 | Proenkephalin | 12.7 |
| PAQR9 | NM_198504 | progestin and adipoQ receptor family member IX | 4.1 |
| LHX2 | NM_004789 | LIM Homeobox 2 | 5.8 |
| SIM2 | U80456 | Single-minded homolog 2 (*Drosophila*) | 9.5 |

[a] Relative methylation degree between the normal sample and the bladder patient sample, calculated by dividing the average signal (Cy5) value in the bladder cancer patient sample in CpG microarrays by the average signal (Cy5) value in the normal person sample.

Example 2

Measurement of Methylation of Biomarker Genes in Cancer Cell Lines

In order to further determine the methylation status of the 10 genes, bisulfite sequencing for each promoter was performed.

In order to modify unmethylated cytosine to uracil using bisulfite, total genomic DNA was isolated from the bladder cancer cell lines RT-4 (Korean Cell Line Bank (KCLB 30002), J82 (KCLB 30001), HT1197 (KCLB 21473) and HT1376 (KCLB 21472), and 200 ng of the genomic DNA was treated with bisulfite using the EZ DNA methylation-gold kit (Zymo Research, USA). When DNA is treated with bisulfite, unmethylated cytosine is modified to uracil, and the methylated cytosine remains without changes. The DNA treated with bisulfite was eluted in 20 μl of sterile distilled water and subjected to pyrosequencing.

PCR and sequencing primers for performing pyrosequencing for the 10 genes were designed using the PSQ assay design program (Biotage, USA). The PCR and sequencing primers for measuring the methylation of each gene are shown in Tables 2 and 3 below.

TABLE 2

Primers and conditions

| Gene | Primer | Sequence (5'→3') | SEQ ID NO: | CpG position[a] | Amplicon size |
|---|---|---|---|---|---|
| CDX2 | forward | TGGTGTTTGTGTTATTATTAATAG | 1 | -138, -129, | 129 bp |
| | reverse | Biotin-CACCTCCTTCCCACTAAACTA | 2 | -121, -118 | |
| CYP1B1 | forward | GTAAGGGTATGGGAATTGA | 3 | +73, +83 | 90 bp |
| | reverse | Biotin-CCCTTAAAAACCTAACAAAATC | 4 | +105 | |
| VSX1 | forward | GGAGTGGGATTGAGGAGATTT | 5 | -1121, -1114, | 89 bp |
| | reverse | Biotin-AAACCCAACCAACCCTCAT | 6 | -1104, 1100 | |
| HOXA11 | forward | AGTAAGTTTATGGGAGGGGGATT | 7 | -415, -405, | 243 bp |
| | reverse | Biotin-CCCCCATACAACATACTTATACTCA | 8 | -388 | |
| T | forward | GGAGGAATGTTATTGTTTAAAGAGAT | 9 | -95, -89, | 326 bp |
| | reverse | Biotin-CAACCCCTTCTAAAAAATATCC | 10 | -76, -71, -69 | |
| TBX5 | forward | GGGTTTGGAGTTAGGTTATG | 11 | -645, -643, | 95 bp |
| | reverse | Biotin-AAATCTAAACTTACCCCCAACT | 12 | -628, -621 | |
| PENK | forward | ATATTTTATTGTATGGGTTTTTTAATAG | 13 | -150, -148, | 322 bp |
| | reverse | Biotin-ACAACCTCAACAAAAAATC | 14 | -139, -135, -133, | 54 bp |
| PAQR9 | forward | Biotin-AGATAGGGGATAATTTTAT | 15 | -480, -475, | 54 bp |
| | reverse | CCTCCCAAACTAAAATTT | 16 | -471, -469 | |
| LHX2 | forward | GTAGAAGGGAAATAAGGTTGAAA | 17 | +5093, | 233 bp |
| | reverse | Biotin-ACTAAAACCCCAATACTCCCA | 18 | +5102, +5113, +5125, +5127 | |

TABLE 2-continued

Primers and conditions

| Gene | Primer | Sequence (5'→3') | SEQ ID NO: | CpG position[a] | Amplicon size |
|---|---|---|---|---|---|
| SIM2 | forward | Biotin-GTGGATTTAGATTAGGATTTTGT | 19 | -6776, -6774, | 205 bp |
| | reverse | CACCCTCCCCAAATTCTT | 20 | -6747, -6744, | |
| | | | | -6743 | |

[a]distances (nucleotides) from the transcription initiation site (+1): the positions of CpG regions on the genomic DNA used in the measurement of methylation

TABLE 3

Sequences of sequencing primers for methylation marker genes

| Gene | Sequence (5'→3') | SEQ ID NO: |
|---|---|---|
| CDX2 | ATT AAT AGA GTT TTG TAA ATA T | 21 |
| CYP1B1 | AAG GGT ATG GGA ATT G | 22 |
| VSX1 | TTT GGG ATT GGG AAG | 23 |
| HOXA11 | TAG TTT AGG GTA TTT TTT ATT TAT | 24 |
| T | GTG AAA GTA ATG ATA TAG TAG AAA | 25 |
| TBX5 | TTT GGG GGT TGG GGA | 26 |
| PENK | GGG TGT TTTAGG TAG TT | 27 |
| PAQR9 | CCT CCC AAA CTA AAA TTT C | 28 |
| LHX2 | TGG GGG TAG AGG AGA | 29 |
| SIM2 | CCT CCC CAA ATT CTT C | 30 |

20 ng of the genomic DNA modified with bisulfite was amplified by PCR. In the PCR amplification, a PCR reaction solution (20 ng of the genomic DNA modified with bisulfite, 5 μl of 10×PCR buffer (Enzynomics, Korea), 5 units of Taq polymerase (Enzynomics, Korea), 4 μl of 2.5 mM dNTP (Solgent, Korea), and 2 μl (10 pmole/μl) of PCR primers) was used, and the PCR reaction was performed in the following conditions: predenaturation at 95° C. for 5 min, and then 45 cycles of denaturation at 95° C. for 40 sec, annealing at 60° C. for 45 sec and extension at 72° C. for 40 sec, followed by final extension at 72° C. for 5 min. The amplification of the PCR product was confirmed by electrophoresis on 2.0% agarose gel.

The amplified PCR product was treated with PyroGold reagents (Biotage, USA), and then subjected to pyrosequencing using the PSQ96MA system (Biotage, USA). After the pyrosequencing, the methylation degree of the DNA was measured by calculating the methylation index. The methylation index was calculated by determining the average rate of cytosine binding to each CpG island.

Figure 2:
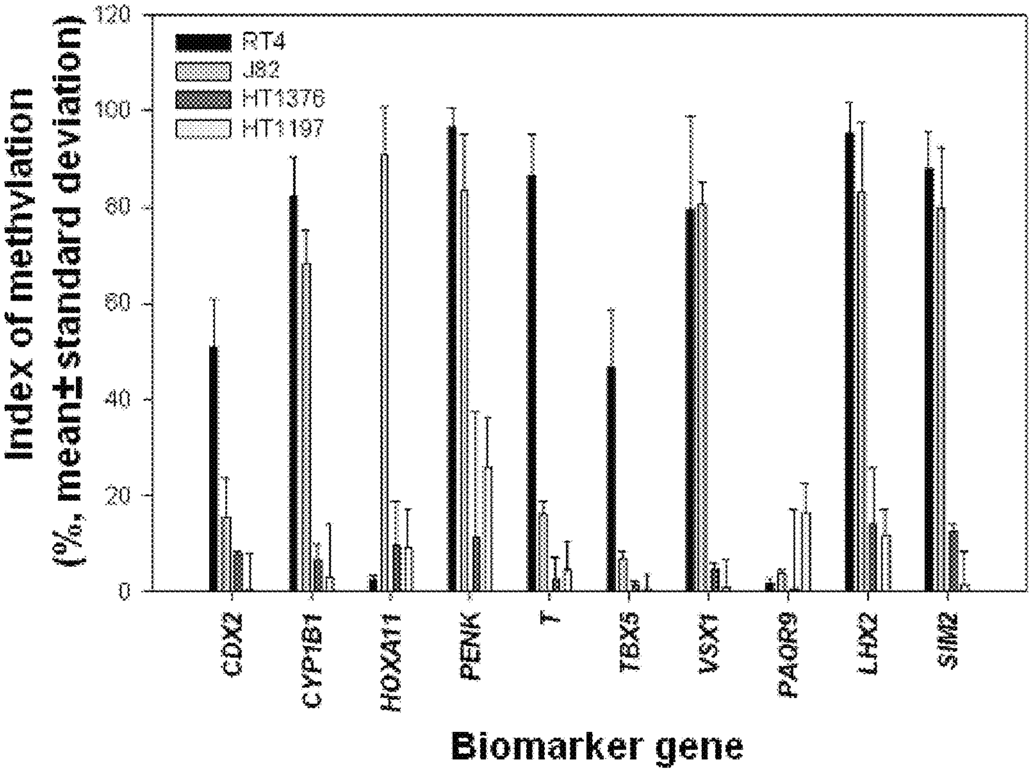
FIG. 2 quantitatively shows the methylation degree obtained through pyrosequencing of 10 methylation biomarkers in bladder cancer cell lines.
Figure 3A:
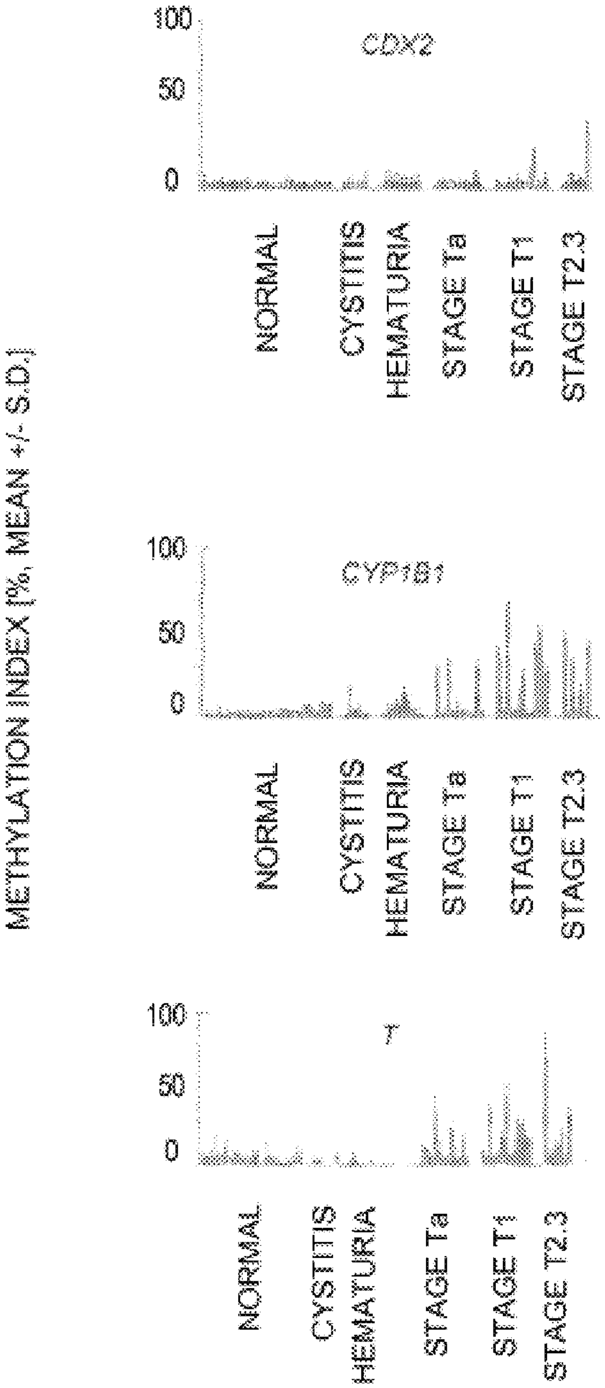
FIG. 3A shows measurement results for the methylation indexes of the CDX2, the CYP1B1 and the T biomarker genes in clinical samples.
Figure 3B:
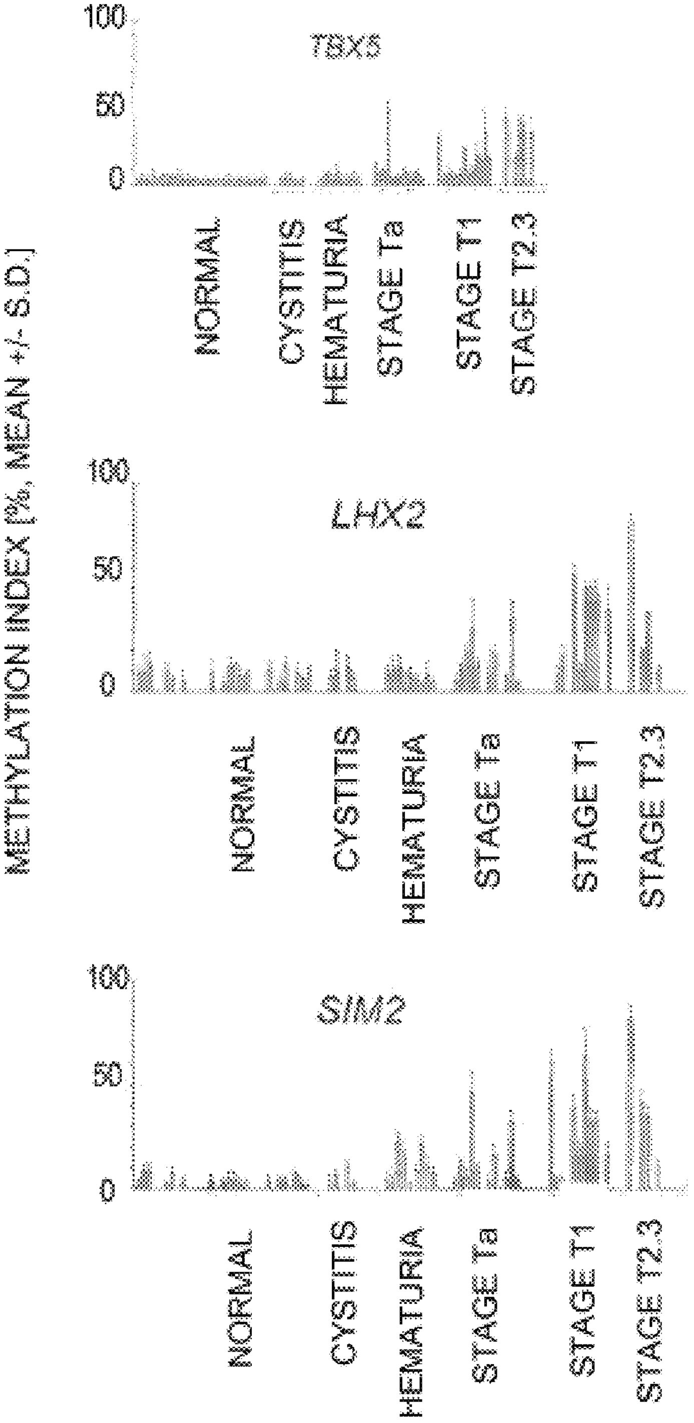
FIG. 3B shows measurement results for the methylation indexes of the TBX5, the LHX2 and the SIM2 biomarker genes in clinical samples.
Figure 3C:
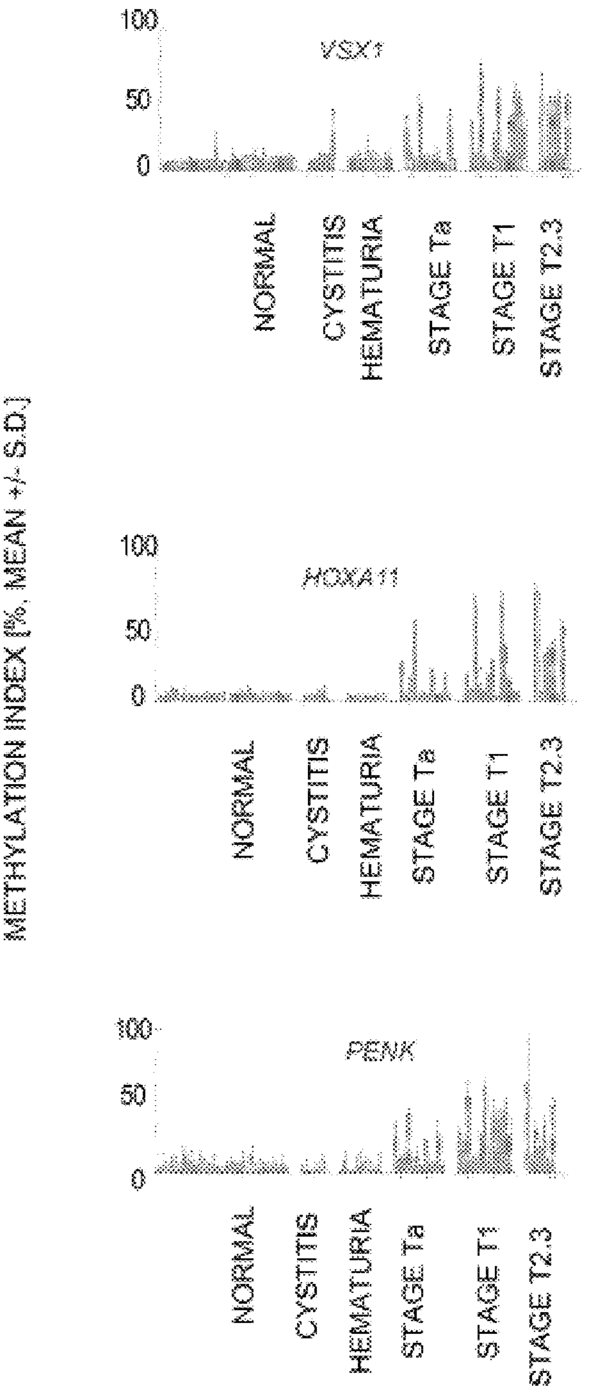
FIG. 3C shows measurement results for the methylation indexes of the VSX1, the HOXA11 and the PENK biomarker genes in clinical samples.
Figure 3D:
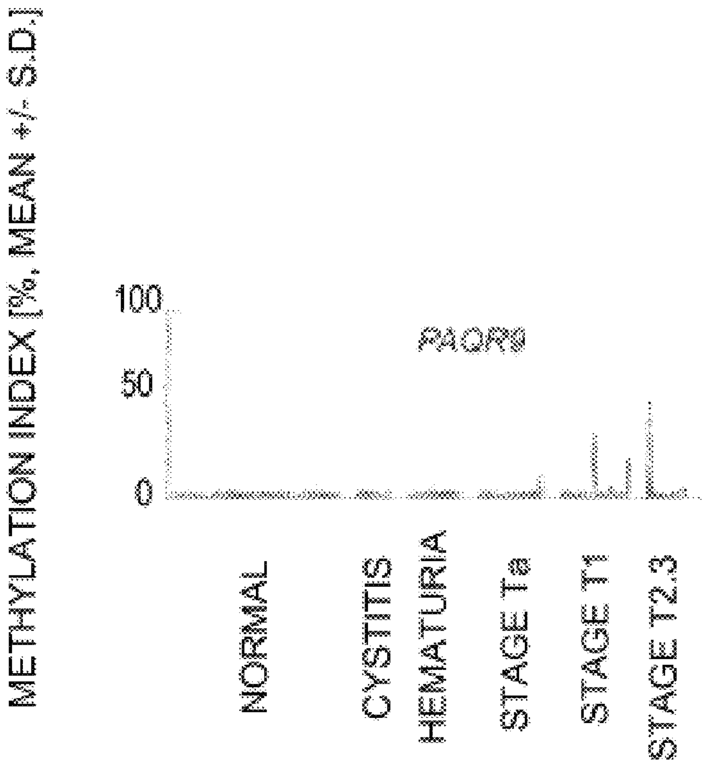
FIG. 3D shows measurement results for the methylation indexes of the PAQR9 biomarker genes in clinical samples.
Figure 4A:
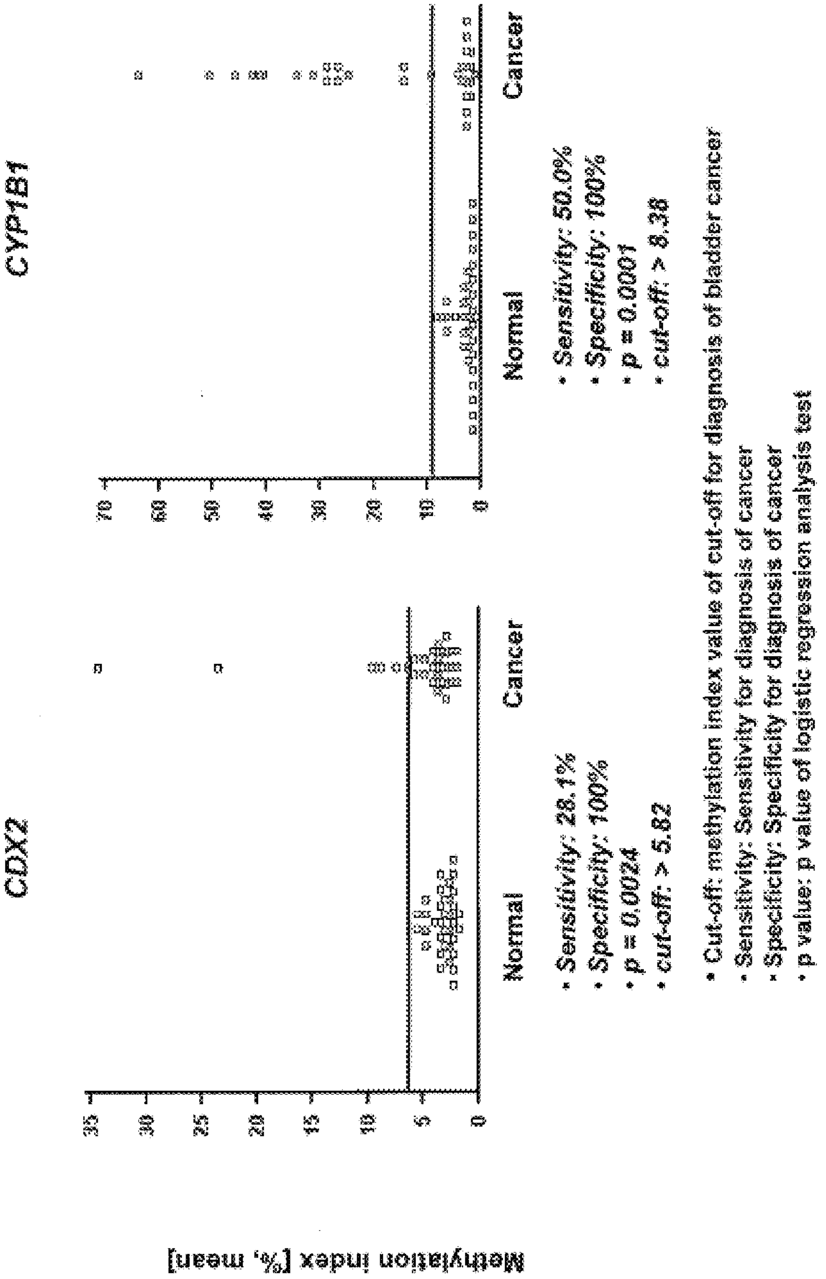
FIG. 4A shows the results of receiver operating characteristic (ROC) curve analysis conducted to measure the sensitivity and specificity of the CDX2 and the CYP1B1 methylation biomarkers for diagnosis of bladder cancer.
Figure 4B:
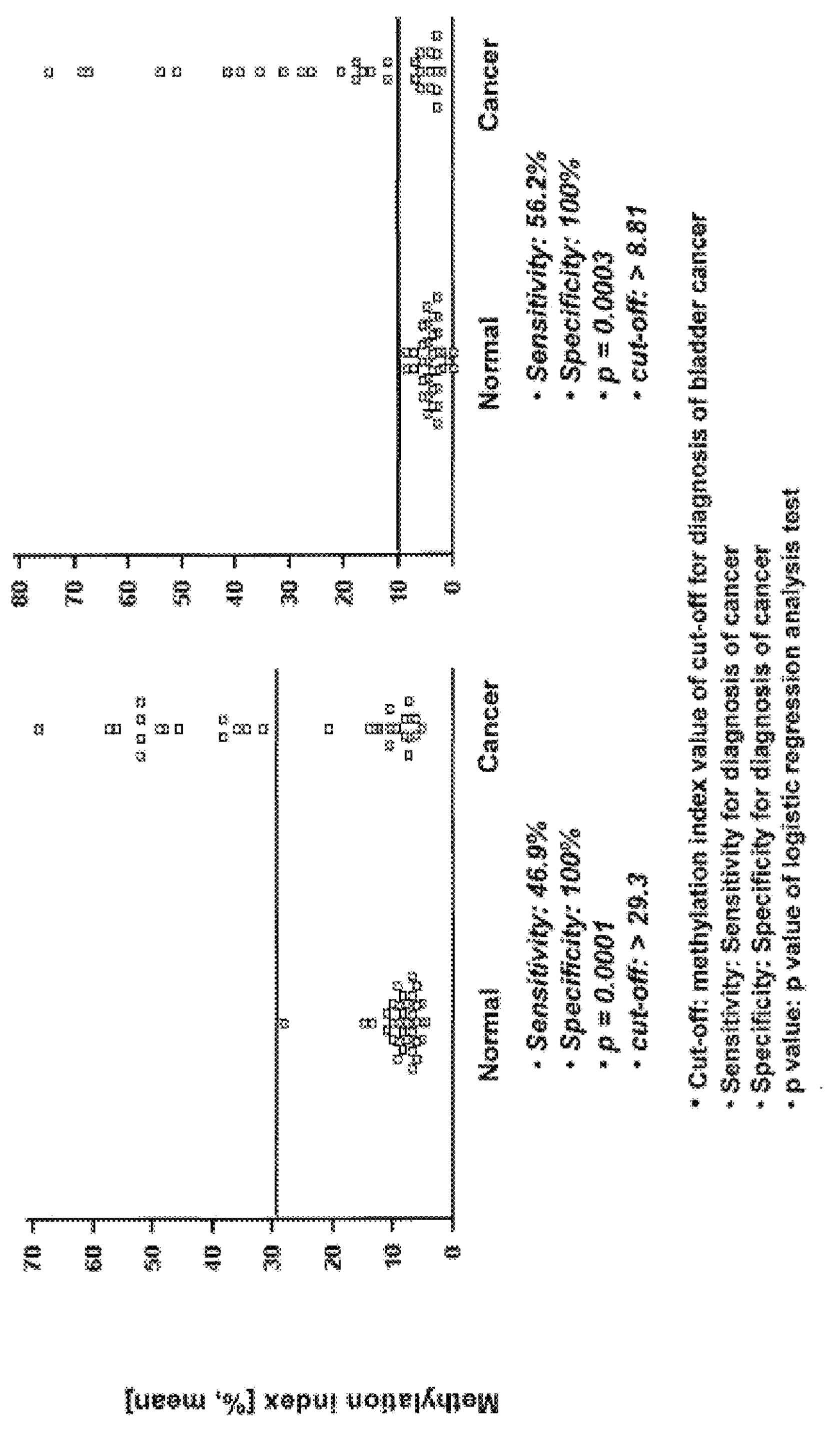
FIG. 4B shows the results of receiver operation characteristic (ROC) curve analysis conducted to measure the sensitivity and specificity of the VSX1 and the HOXA11 methylation biomarkers for diagnosis of bladder cancer.
Figure 4C:
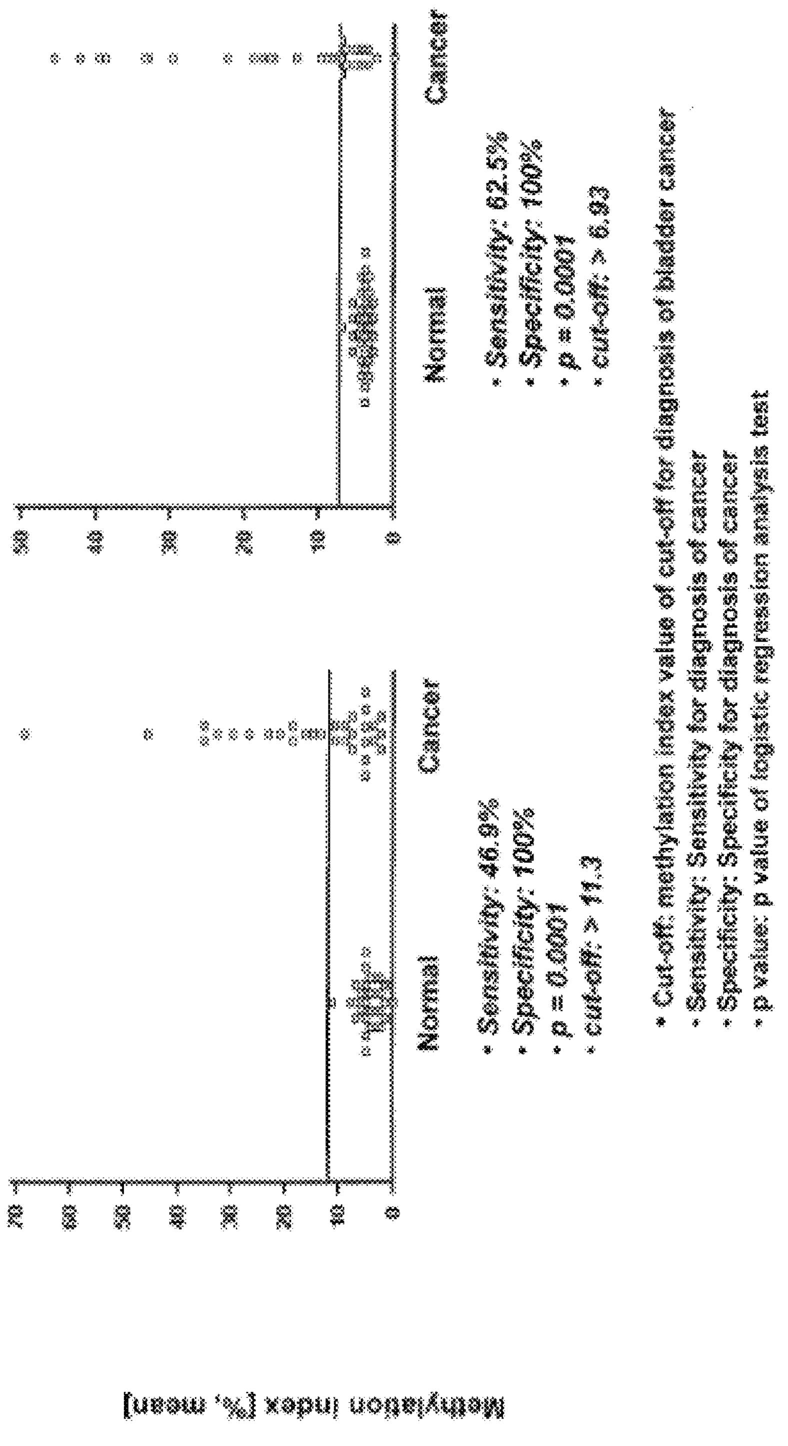
FIG. 4C shows the results of receiver operating characteristic (ROC) curve analysis conducted to measure the sensitivity and specificity of the T and the TBX5 methylation biomarkers for diagnosis of bladder cancer.
Figure 4D:
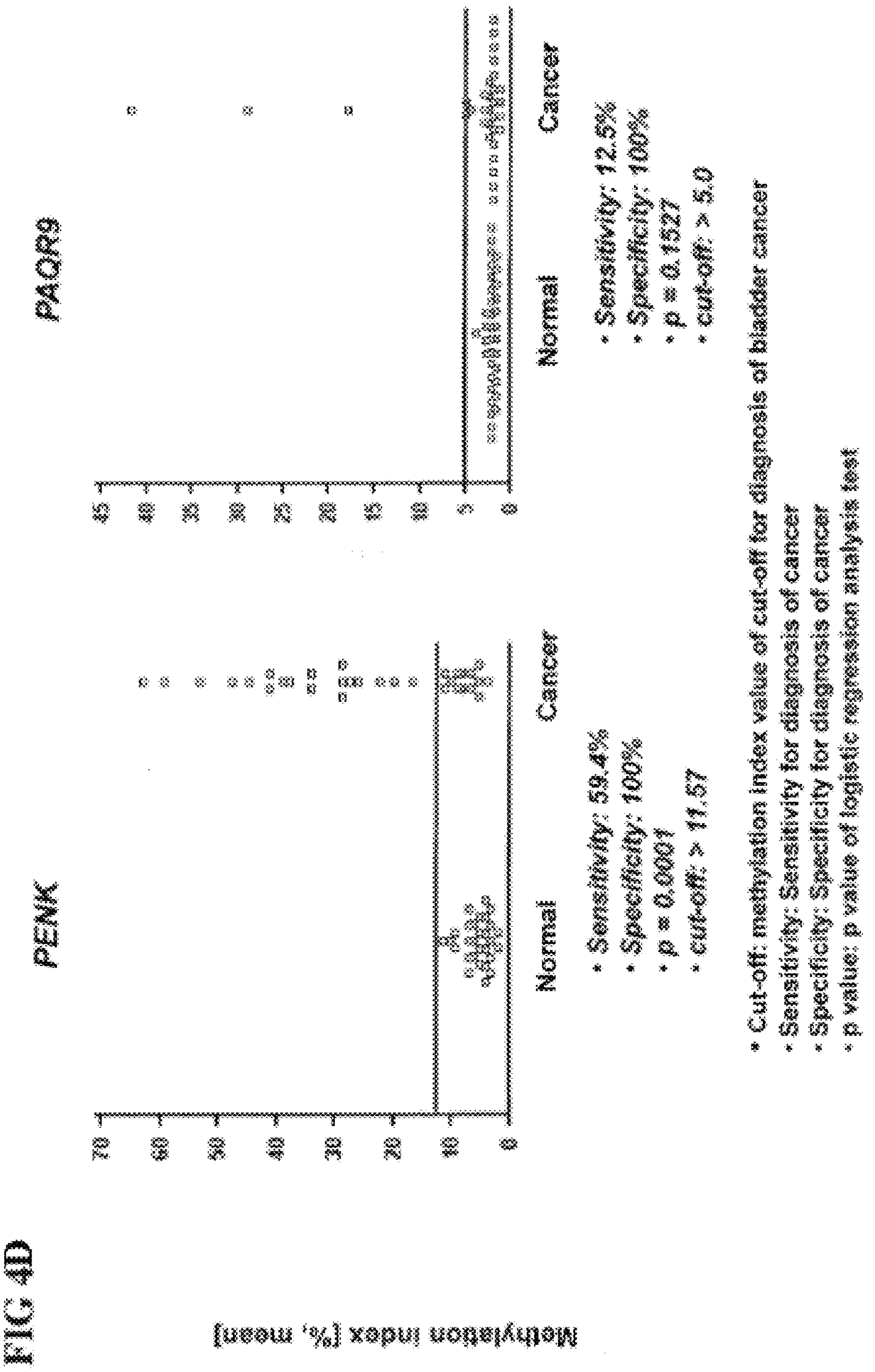
FIG. 4D shows the results of receiver operating characteristic (ROC) curve analysis conducted to measure the sensitivity and specificity of the PENK and the PAQR9 methylation biomarkers for diagnosis of bladder cancer.
Figure 4E:
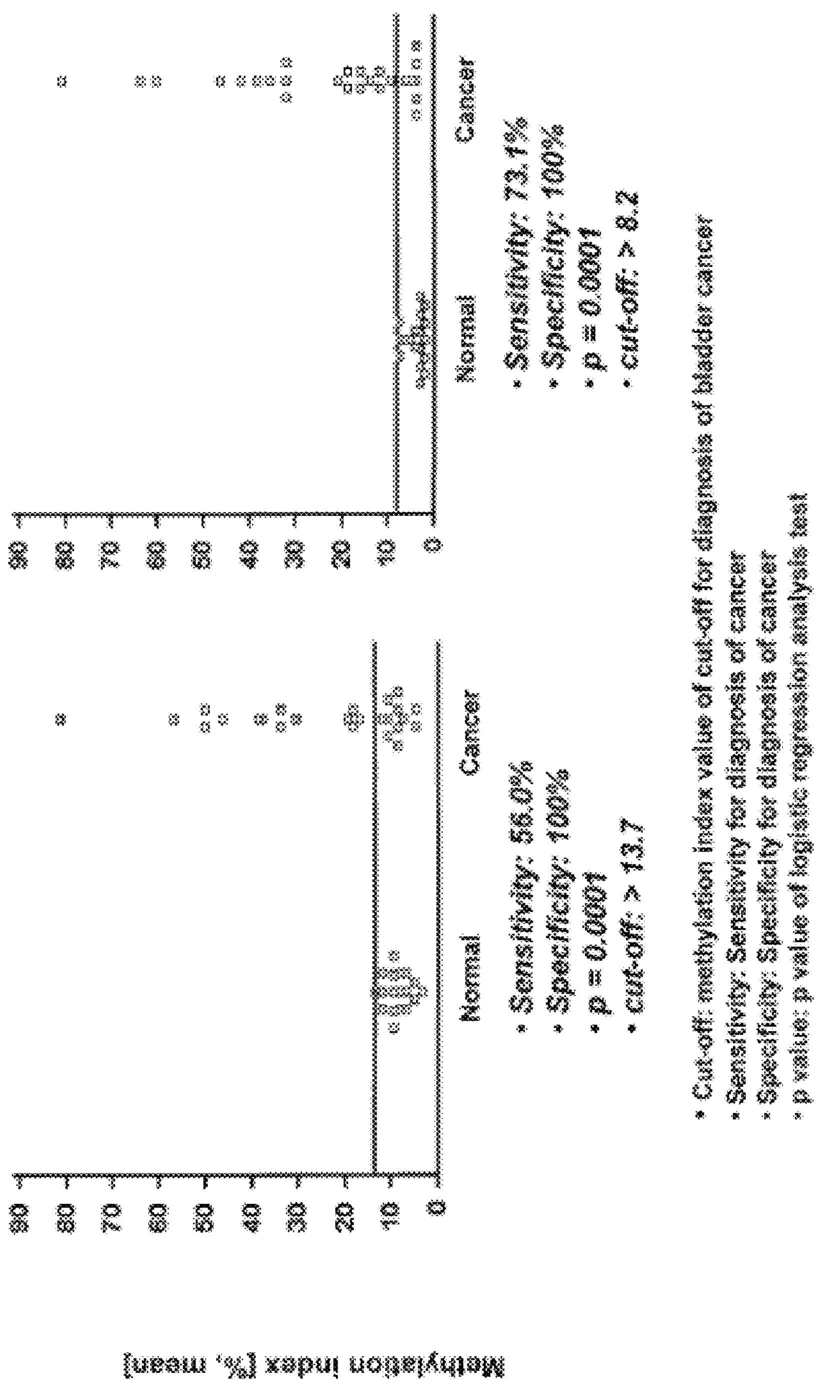
FIG. 4E shows the results of receiver operating characteristic (ROC) curve analysis conducted to measure the sensitivity and specificity of the LHX2 and the SIM2 methylation biomarkers for diagnosis of bladder cancer.

FIG. 2 quantitatively shows the methylation degree of the 10 biomarkers in the bladder cancer cell lines, measured using the pyrosequencing method. As a result, it was shown that the 10 biomarkers were all methylated at high levels in at least one of the cell lines. Table 4 below shows the promoter sequences of the 10 genes.

TABLE 4

Promoter sequences of methylation marker genes

| Gene | SEQ ID NO: |
|---|---|
| CDX2 | 31 |
| CYP1B1 | 32 |
| VSX1 | 33 |
| HOXA11 | 34 |
| T | 35 |
| TBX5 | 36 |
| PENK | 37 |
| PAQR9 | 38 |
| LHX2 | 39 |
| SIM2 | 40 |

Example 3

Measurement of Methylation of Biomarker Genes in Urinary Cells of Bladder Cancer Patients In order to verify whether the 10 genes can be used as biomarkers for diagnosis of bladder cancer, about 20 ml of the urine of each of 20 normal persons and 19 bladder cancer patients was centrifuged in a centrifuge (Hanil Science Industrial Co., Ltd., Korea) at 4,200×g for 10 minutes to isolate cells. The supernatant was discarded, and the cell precipitate was washed twice with 5 ml of PBS. Genomic DNA was isolated from the washed cells using the QIAamp DNA Mini kit (QIAGEN, USA), and 200 ng of the isolated genomic DNA was treated with bisulfite using the EZ DNA methylation-Gold kit (Zymo Research, USA). Then, the DNA was eluted in 20 μl of sterile distilled water and subjected to pyrosequencing.

20 ng of the genomic DNA converted with bisulfite was amplified by PCR. In the PCR amplification, a PCR reaction solution (20 ng of the genomic DNA modified with bisulfite, 5 μl of 10×PCR buffer (Enzynomics, Korea), 5 units of Taq polymerase (Enzynomics, Korea), 4 μl of 2.5 mM dNTP (Solgent, Korea), and 2 μl (10 pmole/μl) of PCR primers) was used, and the PCR reaction was performed in the following conditions: predenaturation at 95° C. for 5 min, and then 45 cycles of denaturation at 95° C. for 40 sec, annealing at 60° C. for 45 sec and extension at 72° C. for 40 sec, followed by final extension at 72° C. for 5 min. The amplification of the PCR product was confirmed by electrophoresis on 2.0% agarose gel.

The amplified PCR product was treated with PyroGold reagents (Biotage, USA), and then subjected to pyrosequencing using the PSQ96MA system (Biotage, USA). After the pyrosequencing, the methylation degree of the DNA was measured by calculating the methylation index thereof. The methylation index was calculated by determining the average rate of cytosine binding to each CpG region. After the methylation index of DNA in the urinary cells of the normal persons and the bladder cancer patients has been measured, a methylation index cut-off value for diagnosis of bladder cancer patients was determined through receiver operating characteristic (ROC) curve analysis.

FIGS. 3A-3D show measurement results for the methylation of the 10 biomarker genes in urinary cells. As can be seen, the methylation degree of the genes was higher in the sample of the bladder cancer patients than in the sample of the normal persons. Meanwhile, the methylation index in the cystitis patients and the hematuria patients was similar to that in the normal control group or was rarely higher than that in the normal control group. FIGS. 4A-4E show ROC analysis results for determining cut-off values for diagnosis of bladder cancer. Also, methylation index cut-off values for the 10 biomarkers, calculated based on the ROC curve analysis results, are shown in Table 5 below.

TABLE 5

Cut-off values for bladder cancer diagnosis of 10 biomarkers

| Gene | cut-off (%)[a] |
|---|---|
| CDX2 | 5.82< |
| CYP1B1 | 8.38< |
| VSX1 | 29.3< |
| HOXA11 | 8.81< |
| T | 11.3< |
| TBX5 | 6.93< |
| PENK | 11.57< |
| PAQR9 | 5.0< |
| LHX2 | 13.7< |
| SIM2 | 8.2< |

In the analysis of the methylation of the 10 biomarkers, the methylation index of each biomarker in the clinical sample was calculated. The case in which the calculated methylation index for diagnosis of bladder cancer was higher than the cut-off value obtained through receiver operating characteristic (ROC) analysis was judged to be methylation-positive, and the case in which the calculated methylation index was lower than the cut-off value was judged to be methylation-negative.

Figure 5:
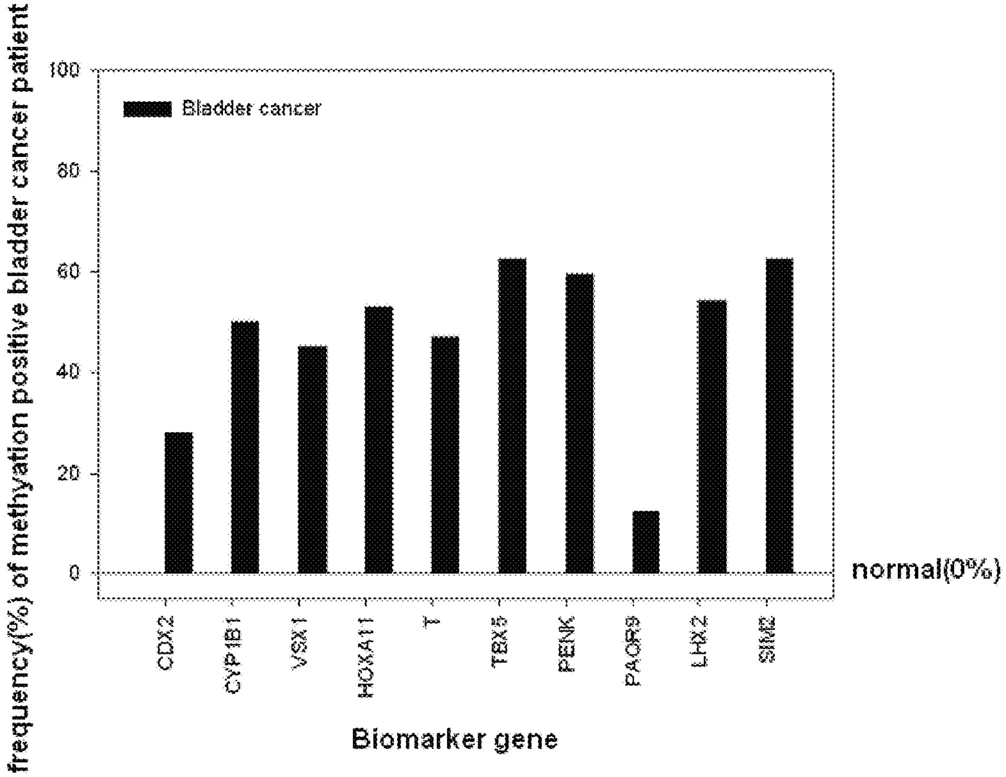
FIG. 5 shows the frequency of methylation in the urinary cells of normal persons and bladder cancer patients.

As shown in Table 6 below and FIG. 5, when judged on the basis of the cut-off value obtained by ROC curve analysis, the urinary cells of the normal persons were methylation-negative for all the 10 biomarkers, but 12.5-62.5% of the samples of the bladder cancer patients were methylation-positive for the 10 biomarkers. Also, statistical analysis was performed and, as a result, it could be seen that 9 of the samples of the bladder cancer samples were methylation-positive for 9 of the 10 biomarkers at a significant level ($p<0.01$) compared to the normal person group. This suggests that 9 of the 10 methylation markers are statistically significantly methylated specifically in bladder cancer and are highly useful for diagnosing bladder cancer.

TABLE 6

Frequency of methylation-positive samples for 10 biomarkers

| Gene | No. of methylation-positive samples/No. of total samples (%)[a] Normal | bladder cancer patient | P value[b] |
|---|---|---|---|
| CDX2 | 0/31 (0) | 9/32 (28.1) | 0.002 |
| CYP1B1 | 0/31 (0) | 16/32 (50.0) | <0.001 |
| VSX1 | 0/31 (0) | 14/32 (45.2) | <0.001 |
| HOXA11 | 0/31 (0) | 17/32 (53.1) | <0.001 |
| T | 0/31 (0) | 15/32 (46.9) | <0.001 |

TABLE 6-continued

Frequency of methylation-positive samples for 10 biomarkers

| Gene | No. of methylation-positive samples/No. of total samples (%)[a] Normal | bladder cancer patient | P value[b] |
|---|---|---|---|
| TBX5 | 0/31 (0) | 20/32 (62.5) | <0.001 |
| PENK | 0/31 (0) | 19/32 (59.4) | <0.001 |
| PAQR9 | 0/31 (0) | 4/32 (12.5) | 0.113 |
| LHX2 | 0/17 (0) | 13/24 (54.2) | <0.001 |
| SIM2 | 0/17 (0) | 15/24 (62.5)0 | <0.001 |

[a]frequency of methylation-positive samples; and
[b]p values obtained through the Chi-Square test

Example 4

Figure 6A:
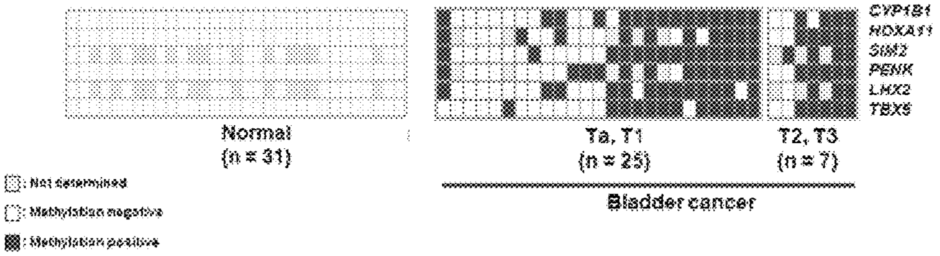
FIGS. 6A-6D shows the methylation profile of an optimal panel of 6 biomarker genes for bladder cancer diagnosis (FIG. 6A), selected from among 10 biomarkers using logistic regression analysis, and shows the sensitivity and specificity of the gene panel for diagnosis of bladder cancer (FIG. 6B-D).
Figure 6B:
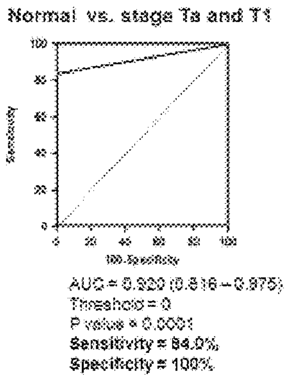
Figure 6C:
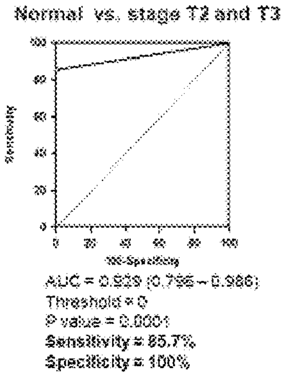
Figure 6D:
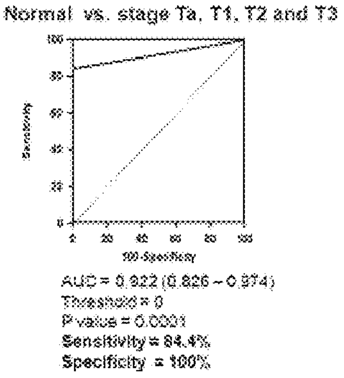

Evaluation of the Ability of 6 Biomarker Panel Genes to Diagnose Bladder Cancer Using the 10 methylation biomarkers, logistic regression analysis was performed. As a result, an optimal panel of 6 genes for diagnosing bladder cancer was established. FIG. 6A shows the methylation status of the 6 biomarkers (CYP1B1, HOXA11, SIM2, PENK, LHX2 and TBX5). Whether samples were methylation-positive or methylation-negative for the 6 genes was judged according to the method described in Example 3. As a result, it could be seen that all the normal samples were methylation-negative for the 6 genes, and only the bladder cancer samples were methylation-positive for the 6 genes. Particularly, early bladder cancer samples were also methylation-positive for the 6 genes at a high frequency, suggesting that the 6 genes are highly useful for early diagnosis of bladder cancer. When the methylation of at least one gene of the gene panel consisting of the six genes was diagnosed as bladder cancer, the sensitivity and specificity of the gene panel for early bladder cancer were as extremely high as 84.0% and 100%, respectively (FIG. 6D). Also, the sensitivity and specificity of the gene panel for advanced bladder cancer were measured to be 85.7% and 100%, respectively (FIG. 6C). In addition, the sensitivity and specificity of the gene panel for all early and advanced bladder cancers were measured to be 84.4% and 100%, respectively (FIG. 6B). This suggests that the methylation of the 6 genes is highly useful for early diagnosis of bladder cancer.

Example 5

Measurement of Methylation of Biomarker Genes Using Methylated DNA-specific Binding Protein In order to measure the methylation of biomarkers which are methylated specifically in bladder cancer, 100 ng of the genomic DNA of each of the bladder cancer cell lines RT24 and HT1197 was sonicated (Vibra Cell, SONICS), thus obtaining about 200-400-bp genomic DNA fragments.

To obtain only methylated DNA from the genomic DNA, MBD known to bind to methylated DNA was used. Specifically, 2 μg of 6×His-tagged MBD was pre-incubated with 500 ng of the genomic DNA of *E. coli* JM110 (No. 2638, Biological Resource Center, Korea Research Institute of Bioscience & Biotechnology), and then bound to Ni-NTA magnetic beads (Qiagen, USA). 100 ng of the sonicated genomic DNA was allowed to react with the beads in the presence of binding buffer solution (10 mM Tris-HCl (pH 7.5), 50 mM NaCl, 1 mM EDTA, 1 mM DTT, 3 mM $MgCl_2$, 0.1% Triton-X100, 5% glycerol, 25 mg/ml BSA) at 4° C. for 20 minutes. Then, the beads were washed three times with 500 μl of a binding buffer solution containing 700 mM NaCl, and then methylated DNA bound to the MBD was isolated using the QiaQuick PCR purification kit (QIAGEN, USA).

Then, the DNA methylated DNA bound to the MBD was amplified by PCR using primers of SEQ ID NOS: 41 and 42 corresponding to the promoter region (from −6842 to −6775 bp) of the SIM2 gene.

```
SEQ ID NO: 41:
5'-TTC TTA TTC TCA CCA GAC ATC TCA ACA CCC-3'

SEQ ID NO: 42:
5'-ATC TCC CAT CCT CCC TCC CAC TCT C-3'
```

The PCR reaction was performed in the following condition: predenaturation at 94° C. for 5 min, and then 40 cycles of denaturation at 94° C. for 30 sec, annealing at 62° C. for 30 sec and extension at 72° C. for 30 sec, followed by final extension at 72° C. for 5 min. The amplification of the PCR product was confirmed by electrophoresis on 2% agarose gel.

Figure 7:
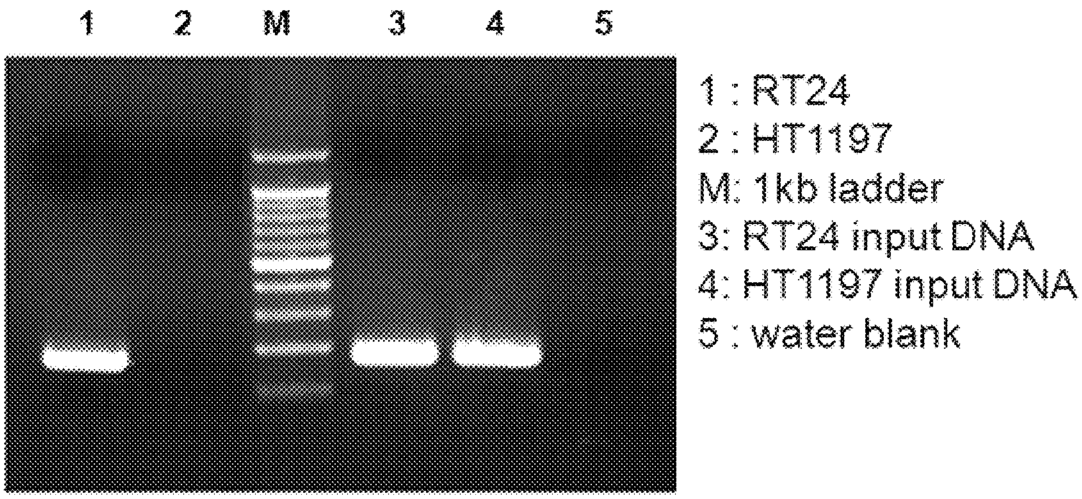
FIG. 7 shows the results of PCR performed using the methylated DNA-specific binding protein MBD in order to measure the methylation of the biomarker SIM2 gene for bladder cancer cell in bladder cancer cell lines.

As a result, it was seen that, for the SIM2 gene, a 168-bp amplified product was detected only in the genomic DNA of the RT24 cell line, suggesting that the gene was methylated, whereas no amplified product was detected in the HT1197 cell line, suggesting that the gene was not methylated in the HT1197 cell line (FIG. 7). Such results were consistent with the methylation measurement results obtained by the pyrosequencing method. Also, such results indicate that the use of MBD enables detection of methylated DNA.

Example 6

Evaluation of the Ability of SIM2 Gene to Diagnose Bladder Cancer by Using qMSP In order to analyze the ability of SIM2 gene to diagnose bladder cancer, 402 sets of primers and probes, which could amplify whole CpG island of SIM2 gene and detect specific methylation sites were designed (Table 7), and methylation specific real time PCR (qMSP) was performed.

First of all, genome DNA of urine cells were isolated from urines, which were obtained from normal control 20 people and 20 bladder cancer patients respectively. Treating bisulfite to the isolated genome DNA by using EZ DNA methylation-Gold kit (Zymo Research, USA) was followed by eluting with 10 μl distilled water, and then was subjected to methylation specific real time PCR (qMSP). qMSP was performed by using bisulfite treated genome DNA as a template and methylation specific primers and probes designed according to Table 1. qMSP was performed by using Rotor-Gene Q PCR equipment (Qiagen). Total 20 μl PCR reaction solution (template DNA, 2 μl; 5× AptaTaq DNA Master (Roche Diagnostics), 4 μl; PCR primers, 2 μl (2 pmole/μl), TaqMan probe, 2 μl (2 pmole/μl); D.W. 10 μl) was prepared. Total 40 times of PCR was performed with a PCR condition that treatment at 95° C. for 5 minutes is followed by treatment at 95° C. for 15 seconds under the proper annealing temperature (58° C.~61° C.) for 1 minute. The amplification of the PCR product was confirmed by measuring the Ct (cycling threshold) value.

Methylated and non-methylated control DNA were tested with sample DNA by using EpiTect PCR control DNA set (Qiagen, cat. no. 59695), and the sensitivity and sensitivity of set of respective primers and probes were calculated with ROC curve analysis (MedCalc Program, Belgium) (Table 8).

TABLE 7

Sequences of primer and probes for SIM2 gene qMSP

| Set | Primer | Sequences (5'→3') | Size of amplification product (bp) | SEQ ID NOs: |
|---|---|---|---|---|
| 1 | F401 | TTGCGTTTTTTTTC | 96 | 43 |
| | R7 | TTATTAAAAATCGC | | 44 |
| | Probe 7 | AGATTTCGCGTAAAAGGTAGGATC | | 45 |
| 2 | F402 | TGCGTTTTTTTTCG | 95 | 46 |
| | R7 | TTATTAAAAATCGC | | 44 |
| | Probe 7 | AGATTTCGCGTAAAAGGTAGGATC | | 45 |
| 3 | F403 | GCGTTTTTTTTCGT | 94 | 47 |
| | R7 | TTATTAAAAATCGC | | 44 |
| | Probe 7 | AGATTTCGCGTAAAAGGTAGGATC | | 45 |
| 4 | F404 | CGTTTTTTTTCGTT | 93 | 48 |
| | R7 | TTATTAAAAATCGC | | 44 |
| | Probe 7 | AGATTTCGCGTAAAAGGTAGGATC | | 45 |
| 5 | F405 | GTTTTTTTTCGTTT | 92 | 49 |
| | R7 | TTATTAAAAATCGC | | 44 |
| | Probe 7 | AGATTTCGCGTAAAAGGTAGGATC | | 45 |
| 6 | F406 | TTTTTTTTCGTTTA | 91 | 50 |
| | R7 | TTATTAAAAATCGC | | 44 |
| | Probe 7 | AGATTTCGCGTAAAAGGTAGGATC | | 45 |
| 7 | F407 | TTTTTTTCGTTTAT | 90 | 51 |
| | R7 | TTATTAAAAATCGC | | 44 |
| | Probe 7 | AGATTTCGCGTAAAAGGTAGGATC | | 45 |

TABLE 7-continued

Sequences of primer and probes for SIM2 gene qMSP

| Set | Primer | Sequences (5'→3') | Size of amplification product (bp) | SEQ ID NOs: |
|---|---|---|---|---|
| 8 | F408 | TTTTTTCGTTTATT | 89 | 52 |
| | R7 | TTATTAAAAATCGC | | 44 |
| | Probe 7 | AGATTTCGCGTAAAAGGTAGGATC | | 45 |
| 9 | F409 | TTTTTCGTTTATTT | 88 | 53 |
| | R7 | TTATTAAAAATCGC | | 44 |
| | Probe 7 | AGATTTCGCGTAAAAGGTAGGATC | | 45 |
| 10 | F410 | TTTTCGTTTATTTG | 87 | 54 |
| | R7 | TTATTAAAAATCGC | | 44 |
| | Probe 7 | AGATTTCGCGTAAAAGGTAGGATC | | 45 |
| 11 | F411 | TTTCGTTTATTTGT | 86 | 55 |
| | R7 | TTATTAAAAATCGC | | 44 |
| | Probe 7 | AGATTTCGCGTAAAAGGTAGGATC | | 45 |
| 12 | F412 | TTCGTTTATTTGTT | 85 | 56 |
| | R7 | TTATTAAAAATCGC | | 44 |
| | Probe 7 | AGATTTCGCGTAAAAGGTAGGATC | | 45 |
| 13 | F413 | TCGTTTATTTGTTT | 84 | 57 |
| | R7 | TTATTAAAAATCGC | | 44 |
| | Probe 7 | AGATTTCGCGTAAAAGGTAGGATC | | 45 |
| 14 | F414 | CGTTTATTTGTTTG | 83 | 58 |
| | R7 | TTATTAAAAATCGC | | 44 |
| | Probe 7 | AGATTTCGCGTAAAAGGTAGGATC | | 45 |
| 15 | F415 | GTTTATTTGTTTGG | 82 | 59 |
| | R7 | TTATTAAAAATCGC | | 44 |
| | Probe 7 | AGATTTCGCGTAAAAGGTAGGATC | | 45 |
| 16 | F416 | TTTATTTGTTTGGT | 81 | 60 |
| | R7 | TTATTAAAAATCGC | | 44 |
| | Probe 7 | AGATTTCGCGTAAAAGGTAGGATC | | 45 |
| 17 | F417 | TTATTTGTTTGGTT | 80 | 61 |
| | R7 | TTATTAAAAATCGC | | 44 |
| | Probe 7 | AGATTTCGCGTAAAAGGTAGGATC | | 45 |
| 18 | F418 | TATTTGTTTGGTTT | 140 | 62 |
| | R8 | CTCGAAACTCTACC | | 63 |
| | Probe 8 | GTTGAGTCGGCGTTTAGGGTCGGG | | 64 |
| 19 | F419 | ATTTGTTTGGTTTG | 139 | 65 |
| | R8 | CTCGAAACTCTACC | | 63 |
| | Probe 8 | GTTGAGTCGGCGTTTAGGGTCGGG | | 64 |
| 20 | F420 | TTTGTTTGGTTTGC | 138 | 66 |
| | R8 | CTCGAAACTCTACC | | 63 |
| | Probe 8 | GTTGAGTCGGCGTTTAGGGTCGGG | | 64 |
| 21 | F421 | TTGTTTGGTTTGCG | 137 | 67 |
| | R8 | CTCGAAACTCTACC | | 63 |
| | Probe 8 | GTTGAGTCGGCGTTTAGGGTCGGG | | 64 |
| 22 | F422 | TGTTTGGTTTGCGT | 136 | 68 |
| | R8 | CTCGAAACTCTACC | | 63 |
| | Probe 8 | GTTGAGTCGGCGTTTAGGGTCGGG | | 64 |
| 23 | F423 | GTTTGGTTTGCGTT | 135 | 69 |
| | R8 | CTCGAAACTCTACC | | 63 |
| | Probe 8 | GTTGAGTCGGCGTTTAGGGTCGGG | | 64 |
| 24 | F424 | TTTGGTTTGCGTTT | 134 | 70 |
| | R8 | CTCGAAACTCTACC | | 63 |
| | Probe 8 | GTTGAGTCGGCGTTTAGGGTCGGG | | 64 |
| 25 | F425 | TTGGTTTGCGTTTT | 133 | 71 |
| | R8 | CTCGAAACTCTACC | | 63 |
| | Probe 8 | GTTGAGTCGGCGTTTAGGGTCGGG | | 64 |

TABLE 7-continued

Sequences of primer and probes for SIM2 gene qMSP

| Set | Primer | Sequences (5'→3') | Size of amplification product (bp) | SEQ ID NOs: |
|---|---|---|---|---|
| 26 | F426 | TGGTTTGCGTTTTT | 132 | 72 |
| | R8 | CTCGAAACTCTACC | | 63 |
| | Probe 8 | GTTGAGTCGGCGTTTAGGGTCGGG | | 64 |
| 27 | F427 | GGTTTGCGTTTTTA | 131 | 73 |
| | R8 | CTCGAAACTCTACC | | 63 |
| | Probe 8 | GTTGAGTCGGCGTTTAGGGTCGGG | | 64 |
| 28 | F428 | GTTTGCGTTTTTAA | 130 | 74 |
| | R8 | CTCGAAACTCTACC | | 63 |
| | Probe 8 | GTTGAGTCGGCGTTTAGGGTCGGG | | 64 |
| 29 | F429 | TTTGCGTTTTTAAT | 129 | 76 |
| | R8 | CTCGAAACTCTACC | | 63 |
| | Probe 8 | GTTGAGTCGGCGTTTAGGGTCGGG | | 64 |
| 30 | F430 | TTGCGTTTTTAATT | 128 | 76 |
| | R8 | CTCGAAACTCTACC | | 63 |
| | Probe 8 | GTTGAGTCGGCGTTTAGGGTCGGG | | 64 |
| 31 | F431 | TGCGTTTTTAATTA | 127 | 77 |
| | R8 | CTCGAAACTCTACC | | 63 |
| | Probe 8 | GTTGAGTCGGCGTTTAGGGTCGGG | | 64 |
| 32 | F432 | GCGTTTTTAATTAC | 126 | 78 |
| | R8 | CTCGAAACTCTACC | | 63 |
| | Probe 8 | GTTGAGTCGGCGTTTAGGGTCGGG | | 64 |
| 33 | F433 | CGTTTTTAATTACG | 125 | 79 |
| | R8 | CTCGAAACTCTACC | | 63 |
| | Probe 8 | GTTGAGTCGGCGTTTAGGGTCGGG | | 64 |
| 34 | F434 | GTTTTTAATTACGC | 124 | 80 |
| | R8 | CTCGAAACTCTACC | | 63 |
| | Probe 8 | GTTGAGTCGGCGTTTAGGGTCGGG | | 64 |
| 35 | F435 | TTTTTAATTACGCG | 123 | 81 |
| | R8 | CTCGAAACTCTACC | | 63 |
| | Probe 8 | GTTGAGTCGGCGTTTAGGGTCGGG | | 64 |
| 36 | F436 | TTTTAATTACGCGG | 122 | 82 |
| | R8 | CTCGAAACTCTACC | | 63 |
| | Probe 8 | GTTGAGTCGGCGTTTAGGGTCGGG | | 64 |
| 37 | F437 | TTTAATTACGCGGG | 121 | 83 |
| | R8 | CTCGAAACTCTACC | | 63 |
| | Probe 8 | GTTGAGTCGGCGTTTAGGGTCGGG | | 64 |
| 38 | F438 | TTAATTACGCGGGC | 120 | 84 |
| | R8 | CTCGAAACTCTACC | | 63 |
| | Probe 8 | GTTGAGTCGGCGTTTAGGGTCGGG | | 64 |
| 39 | F439 | TAATTACGCGGGCG | 119 | 85 |
| | R8 | CTCGAAACTCTACC | | 63 |
| | Probe 8 | GTTGAGTCGGCGTTTAGGGTCGGG | | 64 |
| 40 | F440 | AATTACGCGGGCGG | 118 | 86 |
| | R8 | CTCGAAACTCTACC | | 63 |
| | Probe 8 | GTTGAGTCGGCGTTTAGGGTCGGG | | 64 |
| 41 | F441 | ATTACGCGGGCGGT | 117 | 87 |
| | R8 | CTCGAAACTCTACC | | 63 |
| | Probe 8 | GTTGAGTCGGCGTTTAGGGTCGGG | | 64 |
| 42 | F442 | TTACGCGGGCGGTT | 116 | 88 |
| | R8 | CTCGAAACTCTACC | | 63 |
| | Probe 8 | GTTGAGTCGGCGTTTAGGGTCGGG | | 64 |
| 43 | F443 | TACGCGGGCGGTTT | 115 | 89 |
| | R8 | CTCGAAACTCTACC | | 63 |
| | Probe 8 | GTTGAGTCGGCGTTTAGGGTCGGG | | 64 |

TABLE 7-continued

Sequences of primer and probes for SIM2 gene qMSP

| Set | Primer | Sequences (5'→3') | Size of amplification product (bp) | SEQ ID NOs: |
|---|---|---|---|---|
| 44 | F444 | ACGCGGGCGGTTTC | 114 | 90 |
| | R8 | CTCGAAACTCTACC | | 63 |
| | Probe 8 | GTTGAGTCGGCGTTTAGGGTCGGG | | 64 |
| 45 | F445 | CGCGGGCGGTTTCG | 113 | 91 |
| | R8 | CTCGAAACTCTACC | | 63 |
| | Probe 8 | GTTGAGTCGGCGTTTAGGGTCGGG | | 64 |
| 46 | F446 | GCGGGCGGTTTCGA | 112 | 92 |
| | R8 | CTCGAAACTCTACC | | 63 |
| | Probe 8 | GTTGAGTCGGCGTTTAGGGTCGGG | | 64 |
| 47 | F447 | CGGGCGGTTTCGAG | 111 | 93 |
| | R8 | CTCGAAACTCTACC | | 63 |
| | Probe 8 | GTTGAGTCGGCGTTTAGGGTCGGG | | 64 |
| 48 | F448 | GGGCGGTTTCGAGA | 110 | 94 |
| | R8 | CTCGAAACTCTACC | | 63 |
| | Probe 8 | GTTGAGTCGGCGTTTAGGGTCGGG | | 64 |
| 49 | F449 | GGCGGTTTCGAGAT | 109 | 95 |
| | R8 | CTCGAAACTCTACC | | 63 |
| | Probe 8 | GTTGAGTCGGCGTTTAGGGTCGGG | | 64 |
| 50 | F450 | GCGGTTTCGAGATT | 108 | 96 |
| | R8 | CTCGAAACTCTACC | | 63 |
| | Probe 8 | GTTGAGTCGGCGTTTAGGGTCGGG | | 64 |
| 51 | F451 | CGGTTTCGAGATTT | 107 | 97 |
| | R8 | CTCGAAACTCTACC | | 63 |
| | Probe 8 | GTTGAGTCGGCGTTTAGGGTCGGG | | 64 |
| 52 | F452 | GGTTTCGAGATTTC | 106 | 98 |
| | R8 | CTCGAAACTCTACC | | 63 |
| | Probe 8 | GTTGAGTCGGCGTTTAGGGTCGGG | | 64 |
| 53 | F453 | GTTTCGAGATTTCG | 105 | 99 |
| | R8 | CTCGAAACTCTACC | | 63 |
| | Probe 8 | GTTGAGTCGGCGTTTAGGGTCGGG | | 64 |
| 54 | F454 | TTTCGAGATTTCGC | 104 | 100 |
| | R8 | CTCGAAACTCTACC | | 63 |
| | Probe 8 | GTTGAGTCGGCGTTTAGGGTCGGG | | 64 |
| 55 | F455 | TTCGAGATTTCGCG | 103 | 101 |
| | R8 | CTCGAAACTCTACC | | 63 |
| | Probe 8 | GTTGAGTCGGCGTTTAGGGTCGGG | | 64 |
| 56 | F456 | TCGAGATTTCGCGT | 102 | 102 |
| | R8 | CTCGAAACTCTACC | | 63 |
| | Probe 8 | GTTGAGTCGGCGTTTAGGGTCGGG | | 64 |
| 57 | F457 | CGAGATTTCGCGTA | 101 | 103 |
| | R8 | CTCGAAACTCTACC | | 63 |
| | Probe 8 | GTTGAGTCGGCGTTTAGGGTCGGG | | 64 |
| 58 | F458 | GAGATTTCGCGTAA | 100 | 104 |
| | R8 | CTCGAAACTCTACC | | 63 |
| | Probe 8 | GTTGAGTCGGCGTTTAGGGTCGGG | | 64 |
| 59 | F459 | AGATTTCGCGTAAA | 99 | 105 |
| | R8 | CTCGAAACTCTACC | | 63 |
| | Probe 8 | GTTGAGTCGGCGTTTAGGGTCGGG | | 64 |
| 60 | F460 | GATTTCGCGTAAAA | 98 | 106 |
| | R8 | CTCGAAACTCTACC | | 63 |
| | Probe 8 | GTTGAGTCGGCGTTTAGGGTCGGG | | 64 |
| 61 | F461 | ATTTCGCGTAAAAG | 97 | 107 |
| | R8 | CTCGAAACTCTACC | | 63 |
| | Probe 8 | GTTGAGTCGGCGTTTAGGGTCGGG | | 64 |

TABLE 7-continued

Sequences of primer and probes for SIM2 gene qMSP

| Set | Primer | Sequences (5'→3') | Size of amplification product (bp) | SEQ ID NOs: |
|---|---|---|---|---|
| 62 | F462 | TTTCGCGTAAAAGG | 96 | 108 |
| | R8 | CTCGAAACTCTACC | | 63 |
| | Probe 8 | GTTGAGTCGGCGTTTAGGGTCGGG | | 64 |
| 63 | F463 | TTCGCGTAAAAGGT | 95 | 109 |
| | R8 | CTCGAAACTCTACC | | 63 |
| | Probe 8 | GTTGAGTCGGCGTTTAGGGTCGGG | | 64 |
| 64 | F464 | TCGCGTAAAAGGTA | 94 | 110 |
| | R8 | CTCGAAACTCTACC | | 63 |
| | Probe 8 | GTTGAGTCGGCGTTTAGGGTCGGG | | 64 |
| 65 | F465 | CGCGTAAAAGGTAG | 93 | 111 |
| | R8 | CTCGAAACTCTACC | | 63 |
| | Probe 8 | GTTGAGTCGGCGTTTAGGGTCGGG | | 64 |
| 66 | F466 | GCGTAAAAGGTAGG | 92 | 112 |
| | R8 | CTCGAAACTCTACC | | 63 |
| | Probe 8 | GTTGAGTCGGCGTTTAGGGTCGGG | | 64 |
| 67 | F467 | CGTAAAAGGTAGGA | 91 | 113 |
| | R8 | CTCGAAACTCTACC | | 63 |
| | Probe 8 | GTTGAGTCGGCGTTTAGGGTCGGG | | 64 |
| 68 | F468 | GTAAAAGGTAGGAT | 90 | 114 |
| | R8 | CTCGAAACTCTACC | | 63 |
| | Probe 8 | GTTGAGTCGGCGTTTAGGGTCGGG | | 64 |
| 69 | F469 | TAAAAGGTAGGATC | 89 | 115 |
| | R8 | CTCGAAACTCTACC | | 63 |
| | Probe 8 | GTTGAGTCGGCGTTTAGGGTCGGG | | 64 |
| 70 | F470 | AAAAGGTAGGATCG | 88 | 166 |
| | R8 | CTCGAAACTCTACC | | 63 |
| | Probe 8 | GTTGAGTCGGCGTTTAGGGTCGGG | | 64 |
| 71 | F471 | AAAGGTAGGATCGC | 87 | 117 |
| | R8 | CTCGAAACTCTACC | | 63 |
| | Probe 8 | GTTGAGTCGGCGTTTAGGGTCGGG | | 64 |
| 72 | F472 | AAGGTAGGATCGCG | 86 | 118 |
| | R8 | CTCGAAACTCTACC | | 63 |
| | Probe 8 | GTTGAGTCGGCGTTTAGGGTCGGG | | 64 |
| 73 | F473 | AGGTAGGATCGCGA | 85 | 119 |
| | R8 | CTCGAAACTCTACC | | 63 |
| | Probe 8 | GTTGAGTCGGCGTTTAGGGTCGGG | | 64 |
| 74 | F474 | GGTAGGATCGCGAT | 84 | 120 |
| | R8 | CTCGAAACTCTACC | | 63 |
| | Probe 8 | GTTGAGTCGGCGTTTAGGGTCGGG | | 64 |
| 75 | F475 | GTAGGATCGCGATT | 83 | 121 |
| | R8 | CTCGAAACTCTACC | | 63 |
| | Probe 8 | GTTGAGTCGGCGTTTAGGGTCGGG | | 64 |
| 76 | F476 | TAGGATCGCGATTT | 82 | 122 |
| | R8 | CTCGAAACTCTACC | | 63 |
| | Probe 8 | GTTGAGTCGGCGTTTAGGGTCGGG | | 64 |
| 77 | F477 | AGGATCGCGATTTT | 81 | 123 |
| | R8 | CTCGAAACTCTACC | | 63 |
| | Probe 8 | GTTGAGTCGGCGTTTAGGGTCGGG | | 64 |
| 78 | F478 | GGATCGCGATTTTT | 80 | 124 |
| | R8 | CTCGAAACTCTACC | | 63 |
| | Probe 8 | GTTGAGTCGGCGTTTAGGGTCGGG | | 64 |
| 79 | F479 | GATCGCGATTTTTA | 140 | 125 |
| | R9 | AAAACGATCACAAA | | 126 |
| | Probe 9 | GATTTTTGGCGATCGGGGAGTTTGTT | | 127 |

TABLE 7-continued

Sequences of primer and probes for SIM2 gene qMSP

| Set | Primer | Sequences (5'→3') | Size of amplification product (bp) | SEQ ID NOs: |
|---|---|---|---|---|
| 80 | F480 | ATCGCGATTTTTAA | 139 | 128 |
| | R9 | AAAACGATCACAAA | | 126 |
| | Probe 9 | GATTTTTGGCGATCGGGGAGTTTGTT | | 127 |
| 81 | F481 | TCGCGATTTTTAAT | 138 | 129 |
| | R9 | AAAACGATCACAAA | | 126 |
| | Probe 9 | GATTTTTGGCGATCGGGGAGTTTGTT | | 127 |
| 82 | F482 | CGCGATTTTTAATA | 137 | 130 |
| | R9 | AAAACGATCACAAA | | 126 |
| | Probe 9 | GATTTTTGGCGATCGGGGAGTTTGTT | | 127 |
| 83 | F483 | GCGATTTTTAATAA | 136 | 131 |
| | R9 | AAAACGATCACAAA | | 126 |
| | Probe 9 | GATTTTTGGCGATCGGGGAGTTTGTT | | 127 |
| 84 | F484 | CGATTTTTAATAAT | 135 | 132 |
| | R9 | AAAACGATCACAAA | | 126 |
| | Probe 9 | GATTTTTGGCGATCGGGGAGTTTGTT | | 127 |
| 85 | F485 | GATTTTTAATAATG | 134 | 133 |
| | R9 | AAAACGATCACAAA | | 126 |
| | Probe 9 | GATTTTTGGCGATCGGGGAGTTTGTT | | 127 |
| 86 | F486 | ATTTTTAATAATGA | 133 | 134 |
| | R9 | AAAACGATCACAAA | | 126 |
| | Probe 9 | GATTTTTGGCGATCGGGGAGTTTGTT | | 127 |
| 87 | F487 | TTTTTAATAATGAT | 132 | 135 |
| | R9 | AAAACGATCACAAA | | 126 |
| | Probe 9 | GATTTTTGGCGATCGGGGAGTTTGTT | | 127 |
| 88 | F488 | TTTTAATAATGATA | 131 | 136 |
| | R9 | AAAACGATCACAAA | | 126 |
| | Probe 9 | GATTTTTGGCGATCGGGGAGTTTGTT | | 127 |
| 89 | F489 | TTTAATAATGATAT | 130 | 137 |
| | R9 | AAAACGATCACAAA | | 126 |
| | Probe 9 | GATTTTTGGCGATCGGGGAGTTTGTT | | 127 |
| 90 | F490 | TTAATAATGATATT | 129 | 138 |
| | R9 | AAAACGATCACAAA | | 126 |
| | Probe 9 | GATTTTTGGCGATCGGGGAGTTTGTT | | 127 |
| 91 | F491 | TAATAATGATATTT | 128 | 139 |
| | R9 | AAAACGATCACAAA | | 126 |
| | Probe 9 | GATTTTTGGCGATCGGGGAGTTTGTT | | 127 |
| 92 | F492 | AATAATGATATTTT | 127 | 140 |
| | R9 | AAAACGATCACAAA | | 126 |
| | Probe 9 | GATTTTTGGCGATCGGGGAGTTTGTT | | 127 |
| 93 | F493 | ATAATGATATTTTC | 126 | 141 |
| | R9 | AAAACGATCACAAA | | 126 |
| | Probe 9 | GATTTTTGGCGATCGGGGAGTTTGTT | | 127 |
| 94 | F494 | TAATGATATTTTCG | 125 | 142 |
| | R9 | AAAACGATCACAAA | | 126 |
| | Probe 9 | GATTTTTGGCGATCGGGGAGTTTGTT | | 127 |
| 95 | F495 | AATGATATTTTCGA | 124 | 143 |
| | R9 | AAAACGATCACAAA | | 126 |
| | Probe 9 | GATTTTTGGCGATCGGGGAGTTTGTT | | 127 |
| 96 | F496 | ATGATATTTTCGAA | 123 | 144 |
| | R9 | AAAACGATCACAAA | | 126 |
| | Probe 9 | GATTTTTGGCGATCGGGGAGTTTGTT | | 127 |
| 97 | F497 | TGATATTTTCGAAA | 122 | 145 |
| | R9 | AAAACGATCACAAA | | 126 |
| | Probe 9 | GATTTTTGGCGATCGGGGAGTTTGTT | | 127 |

TABLE 7-continued

Sequences of primer and probes for SIM2 gene qMSP

| Set | Primer | Sequences (5'→3') | Size of amplification product (bp) | SEQ ID NOs: |
|---|---|---|---|---|
| 98 | F498 | GATATTTTCGAAAT | 121 | 146 |
| | R9 | AAAACGATCACAAA | | 126 |
| | Probe 9 | GATTTTTGGCGATCGGGGAGTTTGTT | | 127 |
| 99 | F499 | ATATTTTCGAAATA | 120 | 147 |
| | R9 | AAAACGATCACAAA | | 126 |
| | Probe 9 | GATTTTTGGCGATCGGGGAGTTTGTT | | 127 |
| 100 | F500 | TATTTTCGAAATAA | 119 | 148 |
| | R9 | AAAACGATCACAAA | | 126 |
| | Probe 9 | GATTTTTGGCGATCGGGGAGTTTGTT | | 127 |
| 101 | F501 | ATTTTCGAAATAAT | 118 | 149 |
| | R9 | AAAACGATCACAAA | | 126 |
| | Probe 9 | GATTTTTGGCGATCGGGGAGTTTGTT | | 127 |
| 102 | F502 | TTTTCGAAATAATT | 117 | 150 |
| | R9 | AAAACGATCACAAA | | 126 |
| | Probe 9 | GATTTTTGGCGATCGGGGAGTTTGTT | | 127 |
| 103 | F503 | TTTCGAAATAATTT | 116 | 151 |
| | R9 | AAAACGATCACAAA | | 126 |
| | Probe 9 | GATTTTTGGCGATCGGGGAGTTTGTT | | 127 |
| 104 | F504 | TTCGAAATAATTTT | 115 | 152 |
| | R9 | AAAACGATCACAAA | | 126 |
| | Probe 9 | GATTTTTGGCGATCGGGGAGTTTGTT | | 127 |
| 105 | F505 | TCGAAATAATTTTT | 114 | 153 |
| | R9 | AAAACGATCACAAA | | 126 |
| | Probe 9 | GATTTTTGGCGATCGGGGAGTTTGTT | | 127 |
| 106 | F506 | CGAAATAATTTTTT | 113 | 154 |
| | R9 | AAAACGATCACAAA | | 126 |
| | Probe 9 | GATTTTTGGCGATCGGGGAGTTTGTT | | 127 |
| 107 | F507 | GAAATAATTTTTTG | 112 | 155 |
| | R9 | AAAACGATCACAAA | | 126 |
| | Probe 9 | GATTTTTGGCGATCGGGGAGTTTGTT | | 127 |
| 108 | F508 | AAATAATTTTTTGT | 111 | 156 |
| | R9 | AAAACGATCACAAA | | 126 |
| | Probe 9 | GATTTTTGGCGATCGGGGAGTTTGTT | | 127 |
| 109 | F509 | AATAATTTTTTGTT | 110 | 157 |
| | R9 | AAAACGATCACAAA | | 126 |
| | Probe 9 | GATTTTTGGCGATCGGGGAGTTTGTT | | 127 |
| 110 | F510 | ATAATTTTTTGTTG | 109 | 158 |
| | R9 | AAAACGATCACAAA | | 126 |
| | Probe 9 | GATTTTTGGCGATCGGGGAGTTTGTT | | 127 |
| 111 | F511 | TAATTTTTTGTTGA | 108 | 159 |
| | R9 | AAAACGATCACAAA | | 126 |
| | Probe 9 | GATTTTTGGCGATCGGGGAGTTTGTT | | 127 |
| 112 | F512 | AATTTTTTGTTGAG | 107 | 160 |
| | R9 | AAAACGATCACAAA | | 126 |
| | Probe 9 | GATTTTTGGCGATCGGGGAGTTTGTT | | 127 |
| 113 | F513 | ATTTTTTGTTGAGT | 106 | 161 |
| | R9 | AAAACGATCACAAA | | 126 |
| | Probe 9 | GATTTTTGGCGATCGGGGAGTTTGTT | | 127 |
| 114 | F514 | TTTTTTGTTGAGTC | 105 | 162 |
| | R9 | AAAACGATCACAAA | | 126 |
| | Probe 9 | GATTTTTGGCGATCGGGGAGTTTGTT | | 127 |
| 115 | F515 | TTTTTGTTGAGTCG | 104 | 163 |
| | R9 | AAAACGATCACAAA | | 126 |
| | Probe 9 | GATTTTTGGCGATCGGGGAGTTTGTT | | 127 |

TABLE 7-continued

Sequences of primer and probes for SIM2 gene qMSP

| Set | Primer | Sequences (5'→3') | Size of amplification product (bp) | SEQ ID NOs: |
|---|---|---|---|---|
| 116 | F516 | TTTTGTTGAGTCGG | 103 | 164 |
| | R9 | AAAACGATCACAAA | | 126 |
| | Probe 9 | GATTTTTGGCGATCGGGGAGTTTGTT | | 127 |
| 117 | F517 | TTTGTTGAGTCGGC | 102 | 165 |
| | R9 | AAAACGATCACAAA | | 126 |
| | Probe 9 | GATTTTTGGCGATCGGGGAGTTTGTT | | 127 |
| 118 | F518 | TTGTTGAGTCGGCG | 101 | 166 |
| | R9 | AAAACGATCACAAA | | 126 |
| | Probe 9 | GATTTTTGGCGATCGGGGAGTTTGTT | | 127 |
| 119 | F519 | TGTTGAGTCGGCGT | 100 | 167 |
| | R9 | AAAACGATCACAAA | | 126 |
| | Probe 9 | GATTTTTGGCGATCGGGGAGTTTGTT | | 127 |
| 120 | F520 | GTTGAGTCGGCGTT | 99 | 168 |
| | R9 | AAAACGATCACAAA | | 126 |
| | Probe 9 | GATTTTTGGCGATCGGGGAGTTTGTT | | 127 |
| 121 | F521 | TTGAGTCGGCGTTT | 98 | 169 |
| | R9 | AAAACGATCACAAA | | 126 |
| | Probe 9 | GATTTTTGGCGATCGGGGAGTTTGTT | | 127 |
| 122 | F522 | TGAGTCGGCGTTTA | 97 | 170 |
| | R9 | AAAACGATCACAAA | | 126 |
| | Probe 9 | GATTTTTGGCGATCGGGGAGTTTGTT | | 127 |
| 123 | F523 | GAGTCGGCGTTTAG | 96 | 171 |
| | R9 | AAAACGATCACAAA | | 126 |
| | Probe 9 | GATTTTTGGCGATCGGGGAGTTTGTT | | 127 |
| 124 | F524 | AGTCGGCGTTTAGG | 95 | 172 |
| | R9 | AAAACGATCACAAA | | 126 |
| | Probe 9 | GATTTTTGGCGATCGGGGAGTTTGTT | | 127 |
| 125 | F525 | GTCGGCGTTTAGGG | 94 | 173 |
| | R9 | AAAACGATCACAAA | | 126 |
| | Probe 9 | GATTTTTGGCGATCGGGGAGTTTGTT | | 127 |
| 126 | F526 | TCGGCGTTTAGGGT | 93 | 174 |
| | R9 | AAAACGATCACAAA | | 126 |
| | Probe 9 | GATTTTTGGCGATCGGGGAGTTTGTT | | 127 |
| 127 | F527 | CGGCGTTTAGGGTC | 92 | 175 |
| | R9 | AAAACGATCACAAA | | 126 |
| | Probe 9 | GATTTTTGGCGATCGGGGAGTTTGTT | | 127 |
| 128 | F528 | GGCGTTTAGGGTCG | 91 | 176 |
| | R9 | AAAACGATCACAAA | | 126 |
| | Probe 9 | GATTTTTGGCGATCGGGGAGTTTGTT | | 127 |
| 129 | F529 | GCGTTTAGGGTCGG | 90 | 177 |
| | R9 | AAAACGATCACAAA | | 126 |
| | Probe 9 | GATTTTTGGCGATCGGGGAGTTTGTT | | 127 |
| 130 | F530 | CGTTTAGGGTCGGG | 89 | 178 |
| | R9 | AAAACGATCACAAA | | 126 |
| | Probe 9 | GATTTTTGGCGATCGGGGAGTTTGTT | | 127 |
| 131 | F531 | GTTTAGGGTCGGGG | 88 | 179 |
| | R9 | AAAACGATCACAAA | | 126 |
| | Probe 9 | GATTTTTGGCGATCGGGGAGTTTGTT | | 127 |
| 132 | F532 | TTTAGGGTCGGGGG | 87 | 180 |
| | R9 | AAAACGATCACAAA | | 126 |
| | Probe 9 | GATTTTTGGCGATCGGGGAGTTTGTT | | 127 |
| 133 | F533 | TTAGGGTCGGGGGT | 86 | 181 |
| | R9 | AAAACGATCACAAA | | 126 |
| | Probe 9 | GATTTTTGGCGATCGGGGAGTTTGTT | | 127 |

TABLE 7-continued

Sequences of primer and probes for SIM2 gene qMSP

| Set | Primer | Sequences (5'→3') | Size of amplification product (bp) | SEQ ID NOs: |
|---|---|---|---|---|
| 134 | F534 | TAGGGTCGGGGGTA | 85 | 182 |
| | R9 | AAAACGATCACAAA | | 126 |
| | Probe 9 | GATTTTTGGCGATCGGGGAGTTTGTT | | 127 |
| 135 | F535 | AGGGTCGGGGGTAG | 84 | 183 |
| | R9 | AAAACGATCACAAA | | 126 |
| | Probe 9 | GATTTTTGGCGATCGGGGAGTTTGTT | | 127 |
| 136 | F536 | GGGTCGGGGGTAGA | 83 | 184 |
| | R9 | AAAACGATCACAAA | | 126 |
| | Probe 9 | GATTTTTGGCGATCGGGGAGTTTGTT | | 127 |
| 137 | F537 | GGTCGGGGGTAGAG | 82 | 185 |
| | R9 | AAAACGATCACAAA | | 126 |
| | Probe 9 | GATTTTTGGCGATCGGGGAGTTTGTT | | 127 |
| 138 | F538 | GTCGGGGGTAGAGT | 81 | 186 |
| | R9 | AAAACGATCACAAA | | 126 |
| | Probe 9 | GATTTTTGGCGATCGGGGAGTTTGTT | | 127 |
| 139 | F539 | TCGGGGGTAGAGTT | 80 | 187 |
| | R9 | AAAACGATCACAAA | | 126 |
| | Probe 9 | GATTTTTGGCGATCGGGGAGTTTGTT | | 127 |
| 140 | F540 | CGGGGGTAGAGTTT | 120 | 188 |
| | R10 | ACTACGAACCACAC | | 189 |
| | Probe 10 | AGTTTTTGTCGCGTGCGTGTTCGA | | 190 |
| 141 | F541 | GGGGGTAGAGTTTC | 119 | 191 |
| | R10 | ACTACGAACCACAC | | 189 |
| | Probe 10 | AGTTTTTGTCGCGTGCGTGTTCGA | | 190 |
| 142 | F542 | GGGGTAGAGTTTCG | 118 | 192 |
| | R10 | ACTACGAACCACAC | | 189 |
| | Probe 10 | AGTTTTTGTCGCGTGCGTGTTCGA | | 190 |
| 143 | F543 | GGGTAGAGTTTCGA | 117 | 193 |
| | R10 | ACTACGAACCACAC | | 189 |
| | Probe 10 | AGTTTTTGTCGCGTGCGTGTTCGA | | 190 |
| 144 | F544 | GGTAGAGTTTCGAG | 116 | 194 |
| | R10 | ACTACGAACCACAC | | 189 |
| | Probe 10 | AGTTTTTGTCGCGTGCGTGTTCGA | | 190 |
| 145 | F545 | GTAGAGTTTCGAGT | 115 | 195 |
| | R10 | ACTACGAACCACAC | | 189 |
| | Probe 10 | AGTTTTTGTCGCGTGCGTGTTCGA | | 190 |
| 146 | F546 | TAGAGTTTCGAGTT | 114 | 196 |
| | R10 | ACTACGAACCACAC | | 189 |
| | Probe 10 | AGTTTTTGTCGCGTGCGTGTTCGA | | 190 |
| 147 | F547 | AGAGTTTCGAGTTT | 113 | 197 |
| | R10 | ACTACGAACCACAC | | 189 |
| | Probe 10 | AGTTTTTGTCGCGTGCGTGTTCGA | | 190 |
| 148 | F548 | GAGTTTCGAGTTTT | 112 | 198 |
| | R10 | ACTACGAACCACAC | | 189 |
| | Probe 10 | AGTTTTTGTCGCGTGCGTGTTCGA | | 190 |
| 149 | F549 | AGTTTCGAGTTTTT | 111 | 199 |
| | R10 | ACTACGAACCACAC | | 189 |
| | Probe 10 | AGTTTTTGTCGCGTGCGTGTTCGA | | 190 |
| 150 | F550 | GTTTCGAGTTTTTT | 110 | 200 |
| | R10 | ACTACGAACCACAC | | 189 |
| | Probe 10 | AGTTTTTGTCGCGTGCGTGTTCGA | | 190 |
| 151 | F551 | TTTCGAGTTTTTTT | 109 | 201 |
| | R10 | ACTACGAACCACAC | | 189 |
| | Probe 10 | AGTTTTTGTCGCGTGCGTGTTCGA | | 190 |

TABLE 7-continued

Sequences of primer and probes for SIM2 gene qMSP

| Set | Primer | Sequences (5'→3') | Size of amplification product (bp) | SEQ ID NOs: |
|---|---|---|---|---|
| 152 | F552 | TTCGAGTTTTTTTT | 108 | 202 |
| | R10 | ACTACGAACCACAC | | 189 |
| | Probe 10 | AGTTTTTGTCGCGTGCGTGTTCGA | | 190 |
| 153 | F553 | TCGAGTTTTTTTTG | 107 | 203 |
| | R10 | ACTACGAACCACAC | | 189 |
| | Probe 10 | AGTTTTTGTCGCGTGCGTGTTCGA | | 190 |
| 154 | F554 | CGAGTTTTTTTTGC | 106 | 204 |
| | R10 | ACTACGAACCACAC | | 189 |
| | Probe 10 | AGTTTTTGTCGCGTGCGTGTTCGA | | 190 |
| 155 | F555 | GAGTTTTTTTTGCG | 105 | 205 |
| | R10 | ACTACGAACCACAC | | 189 |
| | Probe 10 | AGTTTTTGTCGCGTGCGTGTTCGA | | 190 |
| 156 | F556 | AGTTTTTTTTGCGG | 104 | 206 |
| | R10 | ACTACGAACCACAC | | 189 |
| | Probe 10 | AGTTTTTGTCGCGTGCGTGTTCGA | | 190 |
| 157 | F557 | GTTTTTTTTGCGGA | 103 | 207 |
| | R10 | ACTACGAACCACAC | | 189 |
| | Probe 10 | AGTTTTTGTCGCGTGCGTGTTCGA | | 190 |
| 158 | F558 | TTTTTTTTGCGGAA | 102 | 208 |
| | R10 | ACTACGAACCACAC | | 189 |
| | Probe 10 | AGTTTTTGTCGCGTGCGTGTTCGA | | 190 |
| 159 | F559 | TTTTTTTGCGGAAT | 101 | 209 |
| | R10 | ACTACGAACCACAC | | 189 |
| | Probe 10 | AGTTTTTGTCGCGTGCGTGTTCGA | | 190 |
| 160 | F560 | TTTTTTGCGGAATT | 100 | 210 |
| | R10 | ACTACGAACCACAC | | 189 |
| | Probe 10 | AGTTTTTGTCGCGTGCGTGTTCGA | | 190 |
| 161 | F561 | TTTTTGCGGAATTA | 99 | 211 |
| | R10 | ACTACGAACCACAC | | 189 |
| | Probe 10 | AGTTTTTGTCGCGTGCGTGTTCGA | | 190 |
| 162 | F562 | TTTTGCGGAATTAA | 98 | 212 |
| | R10 | ACTACGAACCACAC | | 189 |
| | Probe 10 | AGTTTTTGTCGCGTGCGTGTTCGA | | 190 |
| 163 | F563 | TTTGCGGAATTAAG | 97 | 213 |
| | R10 | ACTACGAACCACAC | | 189 |
| | Probe 10 | AGTTTTTGTCGCGTGCGTGTTCGA | | 190 |
| 164 | F564 | TTGCGGAATTAAGG | 96 | 214 |
| | R10 | ACTACGAACCACAC | | 189 |
| | Probe 10 | AGTTTTTGTCGCGTGCGTGTTCGA | | 190 |
| 165 | F565 | TGCGGAATTAAGGA | 95 | 215 |
| | R10 | ACTACGAACCACAC | | 189 |
| | Probe 10 | AGTTTTTGTCGCGTGCGTGTTCGA | | 190 |
| 166 | F566 | GCGGAATTAAGGAG | 94 | 216 |
| | R10 | ACTACGAACCACAC | | 189 |
| | Probe 10 | AGTTTTTGTCGCGTGCGTGTTCGA | | 190 |
| 167 | F567 | CGGAATTAAGGAGA | 93 | 217 |
| | R10 | ACTACGAACCACAC | | 189 |
| | Probe 10 | AGTTTTTGTCGCGTGCGTGTTCGA | | 190 |
| 168 | F568 | GGAATTAAGGAGAT | 92 | 218 |
| | R10 | ACTACGAACCACAC | | 189 |
| | Probe 10 | AGTTTTTGTCGCGTGCGTGTTCGA | | 190 |
| 169 | F569 | GAATTAAGGAGATT | 91 | 219 |
| | R10 | ACTACGAACCACAC | | 189 |
| | Probe 10 | AGTTTTTGTCGCGTGCGTGTTCGA | | 190 |

TABLE 7-continued

Sequences of primer and probes for SIM2 gene qMSP

| Set | Primer | Sequences (5'→3') | Size of amplification product (bp) | SEQ ID NOs: |
|---|---|---|---|---|
| 170 | F570 | AATTAAGGAGATTT | 90 | 220 |
| | R10 | ACTACGAACCACAC | | 189 |
| | Probe 10 | AGTTTTTGTCGCGTGCGTGTTCGA | | 190 |
| 171 | F571 | ATTAAGGAGATTTT | 89 | 221 |
| | R10 | ACTACGAACCACAC | | 189 |
| | Probe 10 | AGTTTTTGTCGCGTGCGTGTTCGA | | 190 |
| 172 | F572 | TTAAGGAGATTTTT | 88 | 222 |
| | R10 | ACTACGAACCACAC | | 189 |
| | Probe 10 | AGTTTTTGTCGCGTGCGTGTTCGA | | 190 |
| 173 | F573 | TAAGGAGATTTTTG | 87 | 223 |
| | R10 | ACTACGAACCACAC | | 189 |
| | Probe 10 | AGTTTTTGTCGCGTGCGTGTTCGA | | 190 |
| 174 | F574 | AAGGAGATTTTTGG | 86 | 224 |
| | R10 | ACTACGAACCACAC | | 189 |
| | Probe 10 | AGTTTTTGTCGCGTGCGTGTTCGA | | 190 |
| 175 | F575 | AGGAGATTTTTGGC | 85 | 225 |
| | R10 | ACTACGAACCACAC | | 189 |
| | Probe 10 | AGTTTTTGTCGCGTGCGTGTTCGA | | 190 |
| 176 | F576 | GGAGATTTTTGGCG | 84 | 226 |
| | R10 | ACTACGAACCACAC | | 189 |
| | Probe 10 | AGTTTTTGTCGCGTGCGTGTTCGA | | 190 |
| 177 | F577 | GAGATTTTTGGCGA | 83 | 227 |
| | R10 | ACTACGAACCACAC | | 189 |
| | Probe 10 | AGTTTTTGTCGCGTGCGTGTTCGA | | 190 |
| 178 | F578 | AGATTTTTGGCGAT | 82 | 228 |
| | R10 | ACTACGAACCACAC | | 189 |
| | Probe 10 | AGTTTTTGTCGCGTGCGTGTTCGA | | 190 |
| 179 | F579 | GATTTTTGGCGATC | 81 | 229 |
| | R10 | ACTACGAACCACAC | | 189 |
| | Probe 10 | AGTTTTTGTCGCGTGCGTGTTCGA | | 190 |
| 180 | F580 | ATTTTTGGCGATCG | 80 | 230 |
| | R10 | ACTACGAACCACAC | | 189 |
| | Probe 10 | AGTTTTTGTCGCGTGCGTGTTCGA | | 190 |
| 181 | F581 | TTTTTGGCGATCGG | 140 | 231 |
| | R11 | GATAATAAACCCGA | | 232 |
| | Probe 11 | GTTTAGGGCGGGGAGAGTTGGCGAT | | 233 |
| 182 | F582 | TTTTGGCGATCGGG | 139 | 234 |
| | R11 | GATAATAAACCCGA | | 232 |
| | Probe 11 | GTTTAGGGCGGGGAGAGTTGGCGAT | | 233 |
| 183 | F583 | TTTGGCGATCGGGG | 138 | 235 |
| | R11 | GATAATAAACCCGA | | 232 |
| | Probe 11 | GTTTAGGGCGGGGAGAGTTGGCGAT | | 233 |
| 184 | F584 | TTGGCGATCGGGGA | 137 | 236 |
| | R11 | GATAATAAACCCGA | | 232 |
| | Probe 11 | GTTTAGGGCGGGGAGAGTTGGCGAT | | 233 |
| 185 | F585 | TGGCGATCGGGGAG | 136 | 237 |
| | R11 | GATAATAAACCCGA | | 232 |
| | Probe 11 | GTTTAGGGCGGGGAGAGTTGGCGAT | | 233 |
| 186 | F586 | GGCGATCGGGGAGT | 135 | 238 |
| | R11 | GATAATAAACCCGA | | 232 |
| | Probe 11 | GTTTAGGGCGGGGAGAGTTGGCGAT | | 233 |
| 187 | F587 | GCGATCGGGGAGTT | 239 | 232 |
| | R11 | GATAATAAACCCGA | 134 | |
| | Probe 11 | GTTTAGGGCGGGGAGAGTTGGCGAT | 233 | |

TABLE 7-continued

Sequences of primer and probes for SIM2 gene qMSP

| Set | Primer | Sequences (5'→3') | Size of amplification product (bp) | SEQ ID NOs: |
|---|---|---|---|---|
| 188 | F588 | CGATCGGGGAGTTT | 133 | 240 |
| | R11 | GATAATAAACCCGA | | 232 |
| | Probe 11 | GTTTAGGGCGGGGAGAGTTGGCGAT | | 233 |
| 189 | F589 | GATCGGGGAGTTTG | 132 | 241 |
| | R11 | GATAATAAACCCGA | | 232 |
| | Probe 11 | GTTTAGGGCGGGGAGAGTTGGCGAT | | 233 |
| 190 | F590 | ATCGGGGAGTTTGT | 131 | 242 |
| | R11 | GATAATAAACCCGA | | 232 |
| | Probe 11 | GTTTAGGGCGGGGAGAGTTGGCGAT | | 233 |
| 191 | F591 | TCGGGGAGTTTGTT | 130 | 243 |
| | R11 | GATAATAAACCCGA | | 232 |
| | Probe 11 | GTTTAGGGCGGGGAGAGTTGGCGAT | | 233 |
| 192 | F592 | CGGGGAGTTTGTTT | 129 | 244 |
| | R11 | GATAATAAACCCGA | | 232 |
| | Probe 11 | GTTTAGGGCGGGGAGAGTTGGCGAT | | 233 |
| 193 | F593 | GGGGAGTTTGTTTT | 128 | 245 |
| | R11 | GATAATAAACCCGA | | 232 |
| | Probe 11 | GTTTAGGGCGGGGAGAGTTGGCGAT | | 233 |
| 194 | F594 | GGGAGTTTGTTTTT | 127 | 246 |
| | R11 | GATAATAAACCCGA | | 232 |
| | Probe 11 | GTTTAGGGCGGGGAGAGTTGGCGAT | | 233 |
| 195 | F595 | GGAGTTTGTTTTTG | 126 | 247 |
| | R11 | GATAATAAACCCGA | | 232 |
| | Probe 11 | GTTTAGGGCGGGGAGAGTTGGCGAT | | 233 |
| 196 | F596 | GAGTTTGTTTTTGT | 125 | 248 |
| | R11 | GATAATAAACCCGA | | 232 |
| | Probe 11 | GTTTAGGGCGGGGAGAGTTGGCGAT | | 233 |
| 197 | F597 | AGTTTGTTTTTGTG | 124 | 249 |
| | R11 | GATAATAAACCCGA | | 232 |
| | Probe 11 | GTTTAGGGCGGGGAGAGTTGGCGAT | | 233 |
| 198 | F598 | GTTTGTTTTTGTGA | 123 | 250 |
| | R11 | GATAATAAACCCGA | | 232 |
| | Probe 11 | GTTTAGGGCGGGGAGAGTTGGCGAT | | 233 |
| 199 | F599 | TTTGTTTTTGTGAT | 122 | 251 |
| | R11 | GATAATAAACCCGA | | 232 |
| | Probe 11 | GTTTAGGGCGGGGAGAGTTGGCGAT | | 233 |
| 200 | F600 | TTGTTTTTGTGATC | 121 | 252 |
| | R11 | GATAATAAACCCGA | | 232 |
| | Probe 11 | GTTTAGGGCGGGGAGAGTTGGCGAT | | 233 |
| 201 | F601 | TGTTTTTGTGATCG | 120 | 253 |
| | R11 | GATAATAAACCCGA | | 232 |
| | Probe 11 | GTTTAGGGCGGGGAGAGTTGGCGAT | | 233 |
| 202 | F602 | GTTTTTGTGATCGT | 119 | 254 |
| | R11 | GATAATAAACCCGA | | 232 |
| | Probe 11 | GTTTAGGGCGGGGAGAGTTGGCGAT | | 233 |
| 203 | F603 | TTTTTGTGATCGTT | 118 | 255 |
| | R11 | GATAATAAACCCGA | | 232 |
| | Probe 11 | GTTTAGGGCGGGGAGAGTTGGCGAT | | 233 |
| 204 | F604 | TTTTGTGATCGTTT | 117 | 256 |
| | R11 | GATAATAAACCCGA | | 232 |
| | Probe 11 | GTTTAGGGCGGGGAGAGTTGGCGAT | | 233 |
| 205 | F605 | TTTGTGATCGTTTT | 116 | 257 |
| | R11 | GATAATAAACCCGA | | 232 |
| | Probe 11 | GTTTAGGGCGGGGAGAGTTGGCGAT | | 233 |

TABLE 7-continued

| Set | Primer | Sequences (5'→3') | Size of amplification product (bp) | SEQ ID NOs: |
|---|---|---|---|---|
| Sequences of primer and probes for SIM2 gene qMSP | | | | |
| 206 | F606 | TTGTGATCGTTTTA | 115 | 258 |
| | R11 | GATAATAAACCCGA | | 232 |
| | Probe 11 | GTTTAGGGCGGGGAGAGTTGGCGAT | | 233 |
| 207 | F607 | TGTGATCGTTTTAG | 114 | 259 |
| | R11 | GATAATAAACCCGA | | 232 |
| | Probe 11 | GTTTAGGGCGGGGAGAGTTGGCGAT | | 233 |
| 208 | F608 | GTGATCGTTTTAGT | 113 | 260 |
| | R11 | GATAATAAACCCGA | | 232 |
| | Probe 11 | GTTTAGGGCGGGGAGAGTTGGCGAT | | 233 |
| 209 | F609 | TGATCGTTTTAGTA | 112 | 261 |
| | R11 | GATAATAAACCCGA | | 232 |
| | Probe 11 | GTTTAGGGCGGGGAGAGTTGGCGAT | | 233 |
| 210 | F610 | GATCGTTTTAGTAG | 111 | 262 |
| | R11 | GATAATAAACCCGA | | 232 |
| | Probe 11 | GTTTAGGGCGGGGAGAGTTGGCGAT | | 233 |
| 211 | F611 | ATCGTTTTAGTAGT | 110 | 263 |
| | R11 | GATAATAAACCCGA | | 232 |
| | Probe 11 | GTTTAGGGCGGGGAGAGTTGGCGAT | | 233 |
| 212 | F612 | TCGTTTTAGTAGTT | 109 | 264 |
| | R11 | GATAATAAACCCGA | | 232 |
| | Probe 11 | GTTTAGGGCGGGGAGAGTTGGCGAT | | 233 |
| 213 | F613 | CGTTTTAGTAGTTT | 108 | 265 |
| | R11 | GATAATAAACCCGA | | 232 |
| | Probe 11 | GTTTAGGGCGGGGAGAGTTGGCGAT | | 233 |
| 214 | F614 | GTTTTAGTAGTTTT | 107 | 266 |
| | R11 | GATAATAAACCCGA | | 232 |
| | Probe 11 | GTTTAGGGCGGGGAGAGTTGGCGAT | | 233 |
| 215 | F615 | TTTTAGTAGTTTTT | 106 | 267 |
| | R11 | GATAATAAACCCGA | | 232 |
| | Probe 11 | GTTTAGGGCGGGGAGAGTTGGCGAT | | 233 |
| 216 | F616 | TTTAGTAGTTTTTG | 105 | 268 |
| | R11 | GATAATAAACCCGA | | 232 |
| | Probe 11 | GTTTAGGGCGGGGAGAGTTGGCGAT | | 233 |
| 217 | F617 | TTAGTAGTTTTTGT | 104 | 269 |
| | R11 | GATAATAAACCCGA | | 232 |
| | Probe 11 | GTTTAGGGCGGGGAGAGTTGGCGAT | | 233 |
| 218 | F618 | TAGTAGTTTTTGTC | 103 | 270 |
| | R11 | GATAATAAACCCGA | | 232 |
| | Probe 11 | GTTTAGGGCGGGGAGAGTTGGCGAT | | 233 |
| 219 | F619 | AGTAGTTTTTGTCG | 102 | 271 |
| | R11 | GATAATAAACCCGA | | 232 |
| | Probe 11 | GTTTAGGGCGGGGAGAGTTGGCGAT | | 233 |
| 220 | F620 | GTAGTTTTTGTCGC | 101 | 272 |
| | R11 | GATAATAAACCCGA | | 232 |
| | Probe 11 | GTTTAGGGCGGGGAGAGTTGGCGAT | | 233 |
| 221 | F621 | TAGTTTTTGTCGCG | 100 | 273 |
| | R11 | GATAATAAACCCGA | | 232 |
| | Probe 11 | GTTTAGGGCGGGGAGAGTTGGCGAT | | 233 |
| 222 | F622 | AGTTTTTGTCGCGT | 99 | 274 |
| | R11 | GATAATAAACCCGA | | 232 |
| | Probe 11 | GTTTAGGGCGGGGAGAGTTGGCGAT | | 233 |
| 223 | F623 | GTTTTTGTCGCGTG | 98 | 275 |
| | R11 | GATAATAAACCCGA | | 232 |
| | Probe 11 | GTTTAGGGCGGGGAGAGTTGGCGAT | | 233 |

TABLE 7-continued

Sequences of primer and probes for SIM2 gene qMSP

| Set | Primer | Sequences (5'→3') | Size of amplification product (bp) | SEQ ID NOs: |
|---|---|---|---|---|
| 224 | F624 | TTTTTGTCGCGTGC | 97 | 276 |
| | R11 | GATAATAAACCCGA | | 232 |
| | Probe 11 | GTTTAGGGCGGGGAGAGTTGGCGAT | | 233 |
| 225 | F625 | TTTTGTCGCGTGCG | 96 | 277 |
| | R11 | GATAATAAACCCGA | | 232 |
| | Probe 11 | GTTTAGGGCGGGGAGAGTTGGCGAT | | 233 |
| 226 | F626 | TTTGTCGCGTGCGT | 95 | 278 |
| | R11 | GATAATAAACCCGA | | 232 |
| | Probe 11 | GTTTAGGGCGGGGAGAGTTGGCGAT | | 233 |
| 227 | F627 | TTGTCGCGTGCGTG | 94 | 279 |
| | R11 | GATAATAAACCCGA | | 233 |
| | Probe 11 | GTTTAGGGCGGGGAGAGTTGGCGAT | | 233 |
| 228 | F628 | TGTCGCGTGCGTGT | 93 | 280 |
| | R11 | GATAATAAACCCGA | | 232 |
| | Probe 11 | GTTTAGGGCGGGGAGAGTTGGCGAT | | 233 |
| 229 | F629 | GTCGCGTGCGTGTT | 92 | 281 |
| | R11 | GATAATAAACCCGA | | 232 |
| | Probe 11 | GTTTAGGGCGGGGAGAGTTGGCGAT | | 233 |
| 230 | F630 | TCGCGTGCGTGTTC | 91 | 282 |
| | R11 | GATAATAAACCCGA | | 232 |
| | Probe 11 | GTTTAGGGCGGGGAGAGTTGGCGAT | | 233 |
| 231 | F631 | CGCGTGCGTGTTCG | 90 | 283 |
| | R11 | GATAATAAACCCGA | | 232 |
| | Probe 11 | GTTTAGGGCGGGGAGAGTTGGCGAT | | 233 |
| 232 | F632 | GCGTGCGTGTTCGA | 89 | 284 |
| | R11 | GATAATAAACCCGA | | 232 |
| | Probe 11 | GTTTAGGGCGGGGAGAGTTGGCGAT | | 233 |
| 233 | F633 | CGTGCGTGTTCGAG | 88 | 285 |
| | R11 | GATAATAAACCCGA | | 232 |
| | Probe 11 | GTTTAGGGCGGGGAGAGTTGGCGAT | | 233 |
| 234 | F634 | GTGCGTGTTCGAGT | 87 | 286 |
| | R11 | GATAATAAACCCGA | | 232 |
| | Probe 11 | GTTTAGGGCGGGGAGAGTTGGCGAT | | 233 |
| 235 | F635 | TGCGTGTTCGAGTG | 86 | 287 |
| | R11 | GATAATAAACCCGA | | 232 |
| | Probe 11 | GTTTAGGGCGGGGAGAGTTGGCGAT | | 233 |
| 236 | F636 | GCGTGTTCGAGTGT | 85 | 288 |
| | R11 | GATAATAAACCCGA | | 232 |
| | Probe 11 | GTTTAGGGCGGGGAGAGTTGGCGAT | | 233 |
| 237 | F637 | CGTGTTCGAGTGTG | 84 | 289 |
| | R11 | GATAATAAACCCGA | | 232 |
| | Probe 11 | GTTTAGGGCGGGGAGAGTTGGCGAT | | 233 |
| 238 | F638 | GTGTTCGAGTGTGG | 83 | 290 |
| | R11 | GATAATAAACCCGA | | 232 |
| | Probe 11 | GTTTAGGGCGGGGAGAGTTGGCGAT | | 233 |
| 239 | F639 | TGTTCGAGTGTGGT | 82 | 291 |
| | R11 | GATAATAAACCCGA | | 232 |
| | Probe 11 | GTTTAGGGCGGGGAGAGTTGGCGAT | | 233 |
| 240 | F640 | GTTCGAGTGTGGTT | 81 | 292 |
| | R11 | GATAATAAACCCGA | | 232 |
| | Probe 11 | GTTTAGGGCGGGGAGAGTTGGCGAT | | 233 |
| 241 | F641 | TTCGAGTGTGGTTC | 80 | 293 |
| | R11 | GATAATAAACCCGA | | 232 |
| | Probe 11 | GTTTAGGGCGGGGAGAGTTGGCGAT | | 233 |

TABLE 7-continued

Sequences of primer and probes for SIM2 gene qMSP

| Set | Primer | Sequences (5'→3') | Size of amplification product (bp) | SEQ ID NOs: |
|---|---|---|---|---|
| 242 | F642 | TCGAGTGTGGTTCG | 140 | 294 |
| | R12 | CCACGCCGAACGTA | | 295 |
| | Probe 12 | GTTTGATTAGATGGGGTGCGGTTTT | | 296 |
| 243 | F643 | CGAGTGTGGTTCGT | 139 | 297 |
| | R12 | CCACGCCGAACGTA | | 295 |
| | Probe 12 | GTTTGATTAGATGGGGTGCGGTTTT | | 296 |
| 244 | F644 | GAGTGTGGTTCGTA | 138 | 298 |
| | R12 | CCACGCCGAACGTA | | 295 |
| | Probe 12 | GTTTGATTAGATGGGGTGCGGTTTT | | 296 |
| 245 | F645 | AGTGTGGTTCGTAG | 137 | 299 |
| | R12 | CCACGCCGAACGTA | | 295 |
| | Probe 12 | GTTTGATTAGATGGGGTGCGGTTTT | | 296 |
| 246 | F646 | GTGTGGTTCGTAGT | 136 | 300 |
| | R12 | CCACGCCGAACGTA | | 295 |
| | Probe 12 | GTTTGATTAGATGGGGTGCGGTTTT | | 269 |
| 247 | F647 | TGTGGTTCGTAGTT | 135 | 301 |
| | R12 | CCACGCCGAACGTA | | 295 |
| | Probe 12 | GTTTGATTAGATGGGGTGCGGTTTT | | 296 |
| 248 | F648 | GTGGTTCGTAGTTT | 134 | 302 |
| | R12 | CCACGCCGAACGTA | | 295 |
| | Probe 12 | GTTTGATTAGATGGGGTGCGGTTTT | | 296 |
| 249 | F649 | TGGTTCGTAGTTTT | 133 | 303 |
| | R12 | CCACGCCGAACGTA | | 295 |
| | Probe 12 | GTTTGATTAGATGGGGTGCGGTTTT | | 296 |
| 250 | F650 | GGTTCGTAGTTTTT | 132 | 304 |
| | R12 | CCACGCCGAACGTA | | 295 |
| | Probe 12 | GTTTGATTAGATGGGGTGCGGTTTT | | 296 |
| 251 | F651 | GTTCGTAGTTTTTA | 131 | 305 |
| | R12 | CCACGCCGAACGTA | | 295 |
| | Probe 12 | GTTTGATTAGATGGGGTGCGGTTTT | | 296 |
| 252 | F652 | TTCGTAGTTTTTAA | 130 | 306 |
| | R12 | CCACGCCGAACGTA | | 295 |
| | Probe 12 | GTTTGATTAGATGGGGTGCGGTTTT | | 296 |
| 253 | F653 | TCGTAGTTTTTAAA | 129 | 307 |
| | R12 | CCACGCCGAACGTA | | 295 |
| | Probe 12 | GTTTGATTAGATGGGGTGCGGTTTT | | 296 |
| 254 | F654 | CGTAGTTTTTAAAG | 128 | 307 |
| | R12 | CCACGCCGAACGTA | | 295 |
| | Probe 12 | GTTTGATTAGATGGGGTGCGGTTTT | | 296 |
| 255 | F655 | GTAGTTTTTAAAGT | 127 | 309 |
| | R12 | CCACGCCGAACGTA | | 295 |
| | Probe 12 | GTTTGATTAGATGGGGTGCGGTTTT | | 296 |
| 256 | F656 | TAGTTTTTAAAGTT | 126 | 310 |
| | R12 | CCACGCCGAACGTA | | 295 |
| | Probe 12 | GTTTGATTAGATGGGGTGCGGTTTT | | 296 |
| 257 | F657 | AGTTTTTAAAGTTT | 125 | 311 |
| | R12 | CCACGCCGAACGTA | | 295 |
| | Probe 12 | GTTTGATTAGATGGGGTGCGGTTTT | | 296 |
| 258 | F658 | GTTTTTAAAGTTTA | 124 | 312 |
| | R12 | CCACGCCGAACGTA | | 295 |
| | Probe 12 | GTTTGATTAGATGGGGTGCGGTTTT | | 296 |
| 259 | F659 | TTTTTAAAGTTTAG | 123 | 313 |
| | R12 | CCACGCCGAACGTA | | 295 |
| | Probe 12 | GTTTGATTAGATGGGGTGCGGTTTT | | 296 |

TABLE 7-continued

Sequences of primer and probes for SIM2 gene qMSP

| Set | Primer | Sequences (5'→3') | Size of amplification product (bp) | SEQ ID NOs: |
|---|---|---|---|---|
| 260 | F660 | TTTTAAAGTTTAGG | 122 | 314 |
| | R12 | CCACGCCGAACGTA | | 295 |
| | Probe 12 | GTTTGATTAGATGGGGTGCGGTTTT | | 296 |
| 261 | F661 | TTTAAAGTTTAGGT | 121 | 315 |
| | R12 | CCACGCCGAACGTA | | 295 |
| | Probe 12 | GTTTGATTAGATGGGGTGCGGTTTT | | 296 |
| 262 | F662 | TTAAAGTTTAGGTG | 120 | 316 |
| | R12 | CCACGCCGAACGTA | | 295 |
| | Probe 12 | GTTTGATTAGATGGGGTGCGGTTTT | | 296 |
| 263 | F663 | TAAAGTTTAGGTGT | 119 | 317 |
| | R12 | CCACGCCGAACGTA | | 295 |
| | Probe 12 | GTTTGATTAGATGGGGTGCGGTTTT | | 296 |
| 264 | F664 | AAAGTTTAGGTGTG | 118 | 318 |
| | R12 | CCACGCCGAACGTA | | 295 |
| | Probe 12 | GTTTGATTAGATGGGGTGCGGTTTT | | 296 |
| 265 | F665 | AAGTTTAGGTGTGT | 117 | 319 |
| | R12 | CCACGCCGAACGTA | | 295 |
| | Probe 12 | GTTTGATTAGATGGGGTGCGGTTTT | | 296 |
| 266 | F666 | AGTTTAGGTGTGTG | 116 | 320 |
| | R12 | CCACGCCGAACGTA | | 295 |
| | Probe 12 | GTTTGATTAGATGGGGTGCGGTTTT | | 296 |
| 267 | F667 | GTTTAGGTGTGTGT | 115 | 321 |
| | R12 | CCACGCCGAACGTA | | 295 |
| | Probe 12 | GTTTGATTAGATGGGGTGCGGTTTT | | 296 |
| 268 | F668 | TTTAGGTGTGTGTG | 114 | 322 |
| | R12 | CCACGCCGAACGTA | | 295 |
| | Probe 12 | GTTTGATTAGATGGGGTGCGGTTTT | | 296 |
| 269 | F669 | TTAGGTGTGTGTGG | 113 | 323 |
| | R12 | CCACGCCGAACGTA | | 295 |
| | Probe 12 | GTTTGATTAGATGGGGTGCGGTTTT | | 296 |
| 270 | F670 | TAGGTGTGTGTGGT | 112 | 324 |
| | R12 | CCACGCCGAACGTA | | 295 |
| | Probe 12 | GTTTGATTAGATGGGGTGCGGTTTT | | 296 |
| 271 | F671 | AGGTGTGTGTGGTT | 111 | 325 |
| | R12 | CCACGCCGAACGTA | | 295 |
| | Probe 12 | GTTTGATTAGATGGGGTGCGGTTTT | | 296 |
| 272 | F672 | GGTGTGTGTGGTTT | 110 | 326 |
| | R12 | CCACGCCGAACGTA | | 295 |
| | Probe 12 | GTTTGATTAGATGGGGTGCGGTTTT | | 296 |
| 273 | F673 | GTGTGTGTGGTTTA | 109 | 327 |
| | R12 | CCACGCCGAACGTA | | 295 |
| | Probe 12 | GTTTGATTAGATGGGGTGCGGTTTT | | 296 |
| 274 | F674 | TGTGTGTGGTTTAG | 108 | 328 |
| | R12 | CCACGCCGAACGTA | | 295 |
| | Probe 12 | GTTTGATTAGATGGGGTGCGGTTTT | | 296 |
| 275 | F675 | GTGTGTGGTTTAGG | 107 | 329 |
| | R12 | CCACGCCGAACGTA | | 295 |
| | Probe 12 | GTTTGATTAGATGGGGTGCGGTTTT | | 296 |
| 276 | F676 | TGTGTGGTTTAGGG | 106 | 330 |
| | R12 | CCACGCCGAACGTA | | 295 |
| | Probe 12 | GTTTGATTAGATGGGGTGCGGTTTT | | 296 |
| 277 | F677 | GTGTGGTTTAGGGC | 105 | 331 |
| | R12 | CCACGCCGAACGTA | | 295 |
| | Probe 12 | GTTTGATTAGATGGGGTGCGGTTTT | | 296 |

TABLE 7-continued

Sequences of primer and probes for SIM2 gene qMSP

| Set | Primer | Sequences (5'→3') | Size of amplification product (bp) | SEQ ID NOs: |
|---|---|---|---|---|
| 278 | F678 | TGTGGTTTAGGGCG | 104 | 332 |
| | R12 | CCACGCCGAACGTA | | 295 |
| | Probe 12 | GTTTGATTAGATGGGGTGCGGTTTT | | 296 |
| 279 | F679 | GTGGTTTAGGGCGG | 103 | 333 |
| | R12 | CCACGCCGAACGTA | | 295 |
| | Probe 12 | GTTTGATTAGATGGGGTGCGGTTTT | | 296 |
| 280 | F680 | TGGTTTAGGGCGGG | 102 | 334 |
| | R12 | CCACGCCGAACGTA | | 295 |
| | Probe 12 | GTTTGATTAGATGGGGTGCGGTTTT | | 296 |
| 281 | F681 | GGTTTAGGGCGGGG | 101 | 335 |
| | R12 | CCACGCCGAACGTA | | 295 |
| | Probe 12 | GTTTGATTAGATGGGGTGCGGTTTT | | 296 |
| 282 | F682 | GTTTAGGGCGGGGA | 100 | 336 |
| | R12 | CCACGCCGAACGTA | | 295 |
| | Probe 12 | GTTTGATTAGATGGGGTGCGGTTTT | | 296 |
| 283 | F683 | TTTAGGGCGGGGAG | 99 | 337 |
| | R12 | CCACGCCGAACGTA | | 295 |
| | Probe 12 | GTTTGATTAGATGGGGTGCGGTTTT | | 296 |
| 284 | F684 | TTAGGGCGGGGAGA | 98 | 338 |
| | R12 | CCACGCCGAACGTA | | 295 |
| | Probe 12 | GTTTGATTAGATGGGGTGCGGTTTT | | 296 |
| 285 | F685 | TAGGGCGGGGAGAG | 97 | 339 |
| | R12 | CCACGCCGAACGTA | | 295 |
| | Probe 12 | GTTTGATTAGATGGGGTGCGGTTTT | | 296 |
| 286 | F686 | AGGGCGGGGAGAGT | 96 | 340 |
| | R12 | CCACGCCGAACGTA | | 295 |
| | Probe 12 | GTTTGATTAGATGGGGTGCGGTTTT | | 296 |
| 287 | F687 | GGGCGGGGAGAGTT | 95 | 341 |
| | R12 | CCACGCCGAACGTA | | 295 |
| | Probe 12 | GTTTGATTAGATGGGGTGCGGTTTT | | 296 |
| 288 | F688 | GGCGGGGAGAGTTG | 94 | 342 |
| | R12 | CCACGCCGAACGTA | | 295 |
| | Probe 12 | GTTTGATTAGATGGGGTGCGGTTTT | | 296 |
| 289 | F689 | GCGGGGAGAGTTGG | 93 | 343 |
| | R12 | CCACGCCGAACGTA | | 295 |
| | Probe 12 | GTTTGATTAGATGGGGTGCGGTTTT | | 296 |
| 290 | F690 | CGGGGAGAGTTGGC | 92 | 344 |
| | R12 | CCACGCCGAACGTA | | 295 |
| | Probe 12 | GTTTGATTAGATGGGGTGCGGTTTT | | 296 |
| 291 | F691 | GGGGAGAGTTGGCG | 91 | 345 |
| | R12 | CCACGCCGAACGTA | | 295 |
| | Probe 12 | GTTTGATTAGATGGGGTGCGGTTTT | | 296 |
| 292 | F692 | GGGAGAGTTGGCGA | 90 | 346 |
| | R12 | CCACGCCGAACGTA | | 295 |
| | Probe 12 | GTTTGATTAGATGGGGTGCGGTTTT | | 296 |
| 293 | F693 | GGAGAGTTGGCGAT | 89 | 347 |
| | R12 | CCACGCCGAACGTA | | 295 |
| | Probe 12 | GTTTGATTAGATGGGGTGCGGTTTT | | 296 |
| 294 | F694 | GAGAGTTGGCGATT | 88 | 348 |
| | R12 | CCACGCCGAACGTA | | 295 |
| | Probe 12 | GTTTGATTAGATGGGGTGCGGTTTT | | 296 |
| 295 | F695 | AGAGTTGGCGATTC | 87 | 349 |
| | R12 | CCACGCCGAACGTA | | 295 |
| | Probe 12 | GTTTGATTAGATGGGGTGCGGTTTT | | 296 |

TABLE 7-continued

Sequences of primer and probes for SIM2 gene qMSP

| Set | Primer | Sequences (5'→3') | Size of amplification product (bp) | SEQ ID NOs: |
|---|---|---|---|---|
| 296 | F696 | GAGTTGGCGATTCG | 86 | 350 |
| | R12 | CCACGCCGAACGTA | | 295 |
| | Probe 12 | GTTTGATTAGATGGGGTGCGGTTTT | | 296 |
| 297 | F697 | AGTTGGCGATTCGG | 85 | 351 |
| | R12 | CCACGCCGAACGTA | | 295 |
| | Probe 12 | GTTTGATTAGATGGGGTGCGGTTTT | | 296 |
| 298 | F698 | GTTGGCGATTCGGG | 84 | 352 |
| | R12 | CCACGCCGAACGTA | | 295 |
| | Probe 12 | GTTTGATTAGATGGGGTGCGGTTTT | | 296 |
| 299 | F699 | TTGGCGATTCGGGT | 83 | 353 |
| | R12 | CCACGCCGAACGTA | | 295 |
| | Probe 12 | GTTTGATTAGATGGGGTGCGGTTTT | | 296 |
| 300 | F700 | TGGCGATTCGGGTT | 82 | 354 |
| | R12 | CCACGCCGAACGTA | | 295 |
| | Probe 12 | GTTTGATTAGATGGGGTGCGGTTTT | | 296 |
| 301 | F701 | GGCGATTCGGGTTT | 81 | 355 |
| | R12 | CCACGCCGAACGTA | | 295 |
| | Probe 12 | GTTTGATTAGATGGGGTGCGGTTTT | | 296 |
| 302 | F702 | GCGATTCGGGTTTA | 80 | 356 |
| | R12 | CCACGCCGAACGTA | | 295 |
| | Probe 12 | GTTTGATTAGATGGGGTGCGGTTTT | | 296 |
| 303 | F703 | CGATTCGGGTTTAT | 140 | 357 |
| | R13 | TCAAAAATTCCGCC | | 358 |
| | Probe 13 | AAGTTCGGTTTTCGTTCGTTTTGCGC | | 359 |
| 304 | F704 | GATTCGGGTTTATT | 139 | 360 |
| | R13 | TCAAAAATTCCGCC | | 358 |
| | Probe 13 | AAGTTCGGTTTTCGTTCGTTTTGCGC | | 359 |
| 305 | F705 | ATTCGGGTTTATTA | 138 | 361 |
| | R13 | TCAAAAATTCCGCC | | 358 |
| | Probe 13 | AAGTTCGGTTTTCGTTCGTTTTGCGC | | 359 |
| 306 | F706 | TTCGGGTTTATTAT | 137 | 362 |
| | R13 | TCAAAAATTCCGCC | | 358 |
| | Probe 13 | AAGTTCGGTTTTCGTTCGTTTTGCGC | | 359 |
| 307 | F707 | TCGGGTTTATTATC | 136 | 363 |
| | R13 | TCAAAAATTCCGCC | | 358 |
| | Probe 13 | AAGTTCGGTTTTCGTTCGTTTTGCGC | | 359 |
| 308 | F708 | CGGGTTTATTATCG | 135 | 364 |
| | R13 | TCAAAAATTCCGCC | | 358 |
| | Probe 13 | AAGTTCGGTTTTCGTTCGTTTTGCGC | | 359 |
| 309 | F709 | GGGTTTATTATCGT | 134 | 365 |
| | R13 | TCAAAAATTCCGCC | | 358 |
| | Probe 13 | AAGTTCGGTTTTCGTTCGTTTTGCGC | | 359 |
| 310 | F710 | GGTTTATTATCGTT | 133 | 366 |
| | R13 | TCAAAAATTCCGCC | | 358 |
| | Probe 13 | AAGTTCGGTTTTCGTTCGTTTTGCGC | | 359 |
| 311 | F711 | GTTTATTATCGTTT | 132 | 367 |
| | R13 | TCAAAAATTCCGCC | | 358 |
| | Probe 13 | AAGTTCGGTTTTCGTTCGTTTTGCGC | | 359 |
| 312 | F712 | TTTATTATCGTTTT | 131 | 368 |
| | R13 | TCAAAAATTCCGCC | | 358 |
| | Probe 13 | AAGTTCGGTTTTCGTTCGTTTTGCGC | | 359 |
| 313 | F713 | TTATTATCGTTTTA | 130 | 369 |
| | R13 | TCAAAAATTCCGCC | | 358 |
| | Probe 13 | AAGTTCGGTTTTCGTTCGTTTTGCGC | | 359 |

TABLE 7-continued

Sequences of primer and probes for SIM2 gene qMSP

| Set | Primer | Sequences (5'→3') | Size of amplification product (bp) | SEQ ID NOs: |
|---|---|---|---|---|
| 314 | F714 | TATTATCGTTTTAG | 129 | 370 |
| | R13 | TCAAAAATTCCGCC | | 358 |
| | Probe 13 | AAGTTCGGTTTTCGTTCGTTTTGCGC | | 359 |
| 315 | F715 | ATTATCGTTTTAGT | 128 | 371 |
| | R13 | TCAAAAATTCCGCC | | 358 |
| | Probe 13 | AAGTTCGGTTTTCGTTCGTTTTGCGC | | 359 |
| 316 | F716 | TTATCGTTTTAGTG | 127 | 372 |
| | R13 | TCAAAAATTCCGCC | | 358 |
| | Probe 13 | AAGTTCGGTTTTCGTTCGTTTTGCGC | | 359 |
| 317 | F717 | TATCGTTTTAGTGT | 126 | 373 |
| | R13 | TCAAAAATTCCGCC | | 358 |
| | Probe 13 | AAGTTCGGTTTTCGTTCGTTTTGCGC | | 359 |
| 318 | F718 | ATCGTTTTAGTGTT | 125 | 374 |
| | R13 | TCAAAAATTCCGCC | | 358 |
| | Probe 13 | AAGTTCGGTTTTCGTTCGTTTTGCGC | | 359 |
| 319 | F719 | TCGTTTTAGTGTTA | 124 | 375 |
| | R13 | TCAAAAATTCCGCC | | 358 |
| | Probe 13 | AAGTTCGGTTTTCGTTCGTTTTGCGC | | 359 |
| 320 | F720 | CGTTTTAGTGTTAT | 123 | 376 |
| | R13 | TCAAAAATTCCGCC | | 358 |
| | Probe 13 | AAGTTCGGTTTTCGTTCGTTTTGCGC | | 359 |
| 321 | F721 | GTTTTAGTGTTATC | 122 | 377 |
| | R13 | TCAAAAATTCCGCC | | 358 |
| | Probe 13 | AAGTTCGGTTTTCGTTCGTTTTGCGC | | 359 |
| 322 | F722 | TTTTAGTGTTATCG | 121 | 378 |
| | R13 | TCAAAAATTCCGCC | | 358 |
| | Probe 13 | AAGTTCGGTTTTCGTTCGTTTTGCGC | | 359 |
| 323 | F723 | TTTAGTGTTATCGT | 120 | 379 |
| | R13 | TCAAAAATTCCGCC | | 358 |
| | Probe 13 | AAGTTCGGTTTTCGTTCGTTTTGCGC | | 359 |
| 324 | F724 | TTAGTGTTATCGTT | 119 | 380 |
| | R13 | TCAAAAATTCCGCC | | 358 |
| | Probe 13 | AAGTTCGGTTTTCGTTCGTTTTGCGC | | 359 |
| 325 | F725 | TAGTGTTATCGTTT | 118 | 381 |
| | R13 | TCAAAAATTCCGCC | | 358 |
| | Probe 13 | AAGTTCGGTTTTCGTTCGTTTTGCGC | | 359 |
| 326 | F726 | AGTGTTATCGTTTT | 117 | 382 |
| | R13 | TCAAAAATTCCGCC | | 358 |
| | Probe 13 | AAGTTCGGTTTTCGTTCGTTTTGCGC | | 359 |
| 327 | F727 | GTGTTATCGTTTTA | 116 | 383 |
| | R13 | TCAAAAATTCCGCC | | 358 |
| | Probe 13 | AAGTTCGGTTTTCGTTCGTTTTGCGC | | 359 |
| 328 | F728 | TGTTATCGTTTTAG | 115 | 384 |
| | R13 | TCAAAAATTCCGCC | | 358 |
| | Probe 13 | AAGTTCGGTTTTCGTTCGTTTTGCGC | | 359 |
| 329 | F729 | GTTATCGTTTTAGT | 114 | 385 |
| | R13 | TCAAAAATTCCGCC | | 358 |
| | Probe 13 | AAGTTCGGTTTTCGTTCGTTTTGCGC | | 359 |
| 330 | F730 | TTATCGTTTTAGTG | 113 | 386 |
| | R13 | TCAAAAATTCCGCC | | 358 |
| | Probe 13 | AAGTTCGGTTTTCGTTCGTTTTGCGC | | 359 |
| 331 | F731 | TATCGTTTTAGTGT | 112 | 387 |
| | R13 | TCAAAAATTCCGCC | | 358 |
| | Probe 13 | AAGTTCGGTTTTCGTTCGTTTTGCGC | | 359 |

TABLE 7-continued

Sequences of primer and probes for SIM2 gene qMSP

| Set | Primer | Sequences (5'→3') | Size of amplification product (bp) | SEQ ID NOs: |
|---|---|---|---|---|
| 332 | F732 | ATCGTTTTAGTGTT | 111 | 388 |
| | R13 | TCAAAAATTCCGCC | | 358 |
| | Probe 13 | AAGTTCGGTTTTCGTTCGTTTTGCGC | | 359 |
| 333 | F733 | TCGTTTTAGTGTTT | 110 | 389 |
| | R13 | TCAAAAATTCCGCC | | 358 |
| | Probe 13 | AAGTTCGGTTTTCGTTCGTTTTGCGC | | 359 |
| 334 | F734 | CGTTTTAGTGTTTG | 109 | 390 |
| | R13 | TCAAAAATTCCGCC | | 358 |
| | Probe 13 | AAGTTCGGTTTTCGTTCGTTTTGCGC | | 359 |
| 335 | F735 | GTTTTAGTGTTTGA | 108 | 391 |
| | R13 | TCAAAAATTCCGCC | | 358 |
| | Probe 13 | AAGTTCGGTTTTCGTTCGTTTTGCGC | | 359 |
| 336 | F736 | TTTTAGTGTTTGAT | 107 | 392 |
| | R13 | TCAAAAATTCCGCC | | 358 |
| | Probe 13 | AAGTTCGGTTTTCGTTCGTTTTGCGC | | 359 |
| 337 | F737 | TTTAGTGTTTGATT | 106 | 393 |
| | R13 | TCAAAAATTCCGCC | | 358 |
| | Probe 13 | AAGTTCGGTTTTCGTTCGTTTTGCGC | | 359 |
| 338 | F738 | TTAGTGTTTGATTA | 105 | 394 |
| | R13 | TCAAAAATTCCGCC | | 358 |
| | Probe 13 | AAGTTCGGTTTTCGTTCGTTTTGCGC | | 359 |
| 339 | F739 | TAGTGTTTGATTAG | 104 | 395 |
| | R13 | TCAAAAATTCCGCC | | 358 |
| | Probe 13 | AAGTTCGGTTTTCGTTCGTTTTGCGC | | 359 |
| 340 | F740 | AGTGTTTGATTAGA | 103 | 396 |
| | R13 | TCAAAAATTCCGCC | | 358 |
| | Probe 13 | AAGTTCGGTTTTCGTTCGTTTTGCGC | | 359 |
| 341 | F741 | GTGTTTGATTAGAT | 102 | 397 |
| | R13 | TCAAAAATTCCGCC | | 358 |
| | Probe 13 | AAGTTCGGTTTTCGTTCGTTTTGCGC | | 359 |
| 342 | F742 | TGTTTGATTAGATG | 101 | 398 |
| | R13 | TCAAAAATTCCGCC | | 358 |
| | Probe 13 | AAGTTCGGTTTTCGTTCGTTTTGCGC | | 359 |
| 343 | F743 | GTTTGATTAGATGG | 100 | 399 |
| | R13 | TCAAAAATTCCGCC | | 358 |
| | Probe 13 | AAGTTCGGTTTTCGTTCGTTTTGCGC | | 359 |
| 344 | F744 | TTTGATTAGATGGG | 99 | 400 |
| | R13 | TCAAAAATTCCGCC | | 358 |
| | Probe 13 | AAGTTCGGTTTTCGTTCGTTTTGCGC | | 359 |
| 345 | F745 | TTGATTAGATGGGG | 98 | 401 |
| | R13 | TCAAAAATTCCGCC | | 358 |
| | Probe 13 | AAGTTCGGTTTTCGTTCGTTTTGCGC | | 359 |
| 346 | F746 | TGATTAGATGGGGT | 97 | 402 |
| | R13 | TCAAAAATTCCGCC | | 358 |
| | Probe 13 | AAGTTCGGTTTTCGTTCGTTTTGCGC | | 359 |
| 347 | F747 | GATTAGATGGGGTG | 96 | 403 |
| | R13 | TCAAAAATTCCGCC | | 358 |
| | Probe 13 | AAGTTCGGTTTTCGTTCGTTTTGCGC | | 359 |
| 348 | F748 | ATTAGATGGGGTGC | 95 | 404 |
| | R13 | TCAAAAATTCCGCC | | 358 |
| | Probe 13 | AAGTTCGGTTTTCGTTCGTTTTGCGC | | 359 |
| 349 | F749 | TTAGATGGGGTGCG | 94 | 405 |
| | R13 | TCAAAAATTCCGCC | | 358 |
| | Probe 13 | AAGTTCGGTTTTCGTTCGTTTTGCGC | | 359 |

TABLE 7-continued

Sequences of primer and probes for SIM2 gene qMSP

| Set | Primer | Sequences (5'→3') | Size of amplification product (bp) | SEQ ID NOs: |
|---|---|---|---|---|
| 350 | F750 | TAGATGGGGTGCGG | 93 | 406 |
| | R13 | TCAAAAATTCCGCC | | 358 |
| | Probe 13 | AAGTTCGGTTTTCGTTCGTTTTGCGC | | 359 |
| 351 | F751 | AGATGGGGTGCGGT | 92 | 407 |
| | R13 | TCAAAAATTCCGCC | | 358 |
| | Probe 13 | AAGTTCGGTTTTCGTTCGTTTTGCGC | | 359 |
| 352 | F752 | GATGGGGTGCGGTT | 91 | 408 |
| | R13 | TCAAAAATTCCGCC | | 358 |
| | Probe 13 | AAGTTCGGTTTTCGTTCGTTTTGCGC | | 359 |
| 353 | F753 | ATGGGGTGCGGTTT | 90 | 409 |
| | R13 | TCAAAAATTCCGCC | | 358 |
| | Probe 13 | AAGTTCGGTTTTCGTTCGTTTTGCGC | | 359 |
| 354 | F754 | TGGGGTGCGGTTTT | 89 | 410 |
| | R13 | TCAAAAATTCCGCC | | 358 |
| | Probe 13 | AAGTTCGGTTTTCGTTCGTTTTGCGC | | 359 |
| 355 | F755 | GGGGTGCGGTTTTT | 88 | 411 |
| | R13 | TCAAAAATTCCGCC | | 358 |
| | Probe 13 | AAGTTCGGTTTTCGTTCGTTTTGCGC | | 359 |
| 356 | F756 | GGGTGCGGTTTTTA | 87 | 412 |
| | R13 | TCAAAAATTCCGCC | | 358 |
| | Probe 13 | AAGTTCGGTTTTCGTTCGTTTTGCGC | | 359 |
| 357 | F757 | GGTGCGGTTTTTAC | 86 | 412 |
| | R13 | TCAAAAATTCCGCC | | 358 |
| | Probe 13 | AAGTTCGGTTTTCGTTCGTTTTGCGC | | 359 |
| 358 | F758 | GTGCGGTTTTTACG | 85 | 414 |
| | R13 | TCAAAAATTCCGCC | | 358 |
| | Probe 13 | AAGTTCGGTTTTCGTTCGTTTTGCGC | | 359 |
| 359 | F759 | TGCGGTTTTTACGT | 84 | 415 |
| | R13 | TCAAAAATTCCGCC | | 358 |
| | Probe 13 | AAGTTCGGTTTTCGTTCGTTTTGCGC | | 359 |
| 360 | F760 | GCGGTTTTTACGTT | 83 | 416 |
| | R13 | TCAAAAATTCCGCC | | 358 |
| | Probe 13 | AAGTTCGGTTTTCGTTCGTTTTGCGC | | 359 |
| 361 | F761 | CGGTTTTTACGTTC | 82 | 417 |
| | R13 | TCAAAAATTCCGCC | | 358 |
| | Probe 13 | AAGTTCGGTTTTCGTTCGTTTTGCGC | | 359 |
| 362 | F762 | GGTTTTTACGTTCG | 81 | 418 |
| | R13 | TCAAAAATTCCGCC | | 358 |
| | Probe 13 | AAGTTCGGTTTTCGTTCGTTTTGCGC | | 359 |
| 363 | F763 | GTTTTTACGTTCGG | 80 | 419 |
| | R13 | TCAAAAATTCCGCC | | 358 |
| | Probe 13 | AAGTTCGGTTTTCGTTCGTTTTGCGC | | 359 |
| 364 | F764 | TTTTTACGTTCGGC | 140 | 420 |
| | R14 | AAAACCCATTCATT | | 421 |
| | Probe 14 | GTTTCGTTTTTTTTTTTGGAAGG | | 422 |
| 365 | F765 | TTTTACGTTCGGCG | 139 | 423 |
| | R14 | AAAACCCATTCATT | | 421 |
| | Probe 14 | GTTTCGTTTTTTTTTTTGGAAGG | | 422 |
| 366 | F766 | TTTACGTTCGGCGT | 138 | 424 |
| | R14 | AAAACCCATTCATT | | 421 |
| | Probe 14 | GTTTCGTTTTTTTTTTTGGAAGG | | 422 |
| 367 | F767 | TTACGTTCGGCGTG | 137 | 425 |
| | R14 | AAAACCCATTCATT | | 421 |
| | Probe 14 | GTTTCGTTTTTTTTTTTGGAAGG | | 422 |

TABLE 7-continued

Sequences of primer and probes for SIM2 gene qMSP

| Set | Primer | Sequences (5'→3') | Size of amplification product (bp) | SEQ ID NOs: |
|---|---|---|---|---|
| 368 | F768 | TACGTTCGGCGTGG | 136 | 426 |
| | R14 | AAAACCCATTCATT | | 421 |
| | Probe 14 | GTTTCGTTTTTTTTTTTTGGAAGG | | 422 |
| 369 | F769 | ACGTTCGGCGTGGT | 135 | 427 |
| | R14 | AAAACCCATTCATT | | 421 |
| | Probe 14 | GTTTCGTTTTTTTTTTTTGGAAGG | | 422 |
| 370 | F770 | CGTTCGGCGTGGTT | 134 | 428 |
| | R14 | AAAACCCATTCATT | | 421 |
| | Probe 14 | GTTTCGTTTTTTTTTTTTGGAAGG | | 422 |
| 371 | F771 | GTTCGGCGTGGTTT | 133 | 429 |
| | R14 | AAAACCCATTCATT | | 421 |
| | Probe 14 | GTTTCGTTTTTTTTTTTTGGAAGG | | 422 |
| 372 | F772 | TTCGGCGTGGTTTC | 132 | 430 |
| | R14 | AAAACCCATTCATT | | 421 |
| | Probe 14 | GTTTCGTTTTTTTTTTTTGGAAGG | | 422 |
| 373 | F773 | TCGGCGTGGTTTCG | 131 | 431 |
| | R14 | AAAACCCATTCATT | | 421 |
| | Probe 14 | GTTTCGTTTTTTTTTTTTGGAAGG | | 422 |
| 374 | F774 | CGGCGTGGTTTCGT | 130 | 432 |
| | R14 | AAAACCCATTCATT | | 421 |
| | Probe 14 | GTTTCGTTTTTTTTTTTTGGAAGG | | 422 |
| 375 | F775 | GGCGTGGTTTCGTC | 129 | 433 |
| | R14 | AAAACCCATTCATT | | 421 |
| | Probe 14 | GTTTCGTTTTTTTTTTTTGGAAGG | | 422 |
| 376 | F776 | GCGTGGTTTCGTCG | 128 | 434 |
| | R14 | AAAACCCATTCATT | | 421 |
| | Probe 14 | GTTTCGTTTTTTTTTTTTGGAAGG | | 422 |
| 377 | F777 | CGTGGTTTCGTCGT | 127 | 435 |
| | R14 | AAAACCCATTCATT | | 421 |
| | Probe 14 | GTTTCGTTTTTTTTTTTTGGAAGG | | 422 |
| 378 | F778 | GTGGTTTCGTCGTC | 126 | 436 |
| | R14 | AAAACCCATTCATT | | 421 |
| | Probe 14 | GTTTCGTTTTTTTTTTTTGGAAGG | | 422 |
| 379 | F779 | TGGTTTCGTCGTCG | 125 | 437 |
| | R14 | AAAACCCATTCATT | | 421 |
| | Probe 14 | GTTTCGTTTTTTTTTTTTGGAAGG | | 422 |
| 380 | F780 | GGTTTCGTCGTCGT | 124 | 438 |
| | R14 | AAAACCCATTCATT | | 421 |
| | Probe 14 | GTTTCGTTTTTTTTTTTTGGAAGG | | 422 |
| 381 | F781 | GTTTCGTCGTCGTT | 123 | 439 |
| | R14 | AAAACCCATTCATT | | 421 |
| | Probe 14 | GTTTCGTTTTTTTTTTTTGGAAGG | | 422 |
| 382 | F782 | TTTCGTCGTCGTTT | 122 | 440 |
| | R14 | AAAACCCATTCATT | | 421 |
| | Probe 14 | GTTTCGTTTTTTTTTTTTGGAAGG | | 422 |
| 383 | F783 | TTCGTCGTCGTTTA | 121 | 441 |
| | R14 | AAAACCCATTCATT | | 421 |
| | Probe 14 | GTTTCGTTTTTTTTTTTTGGAAGG | | 422 |
| 384 | F784 | TCGTCGTCGTTTAG | 120 | 442 |
| | R14 | AAAACCCATTCATT | | 421 |
| | Probe 14 | GTTTCGTTTTTTTTTTTTGGAAGG | | 422 |
| 385 | F785 | CGTCGTCGTTTAGA | 119 | 443 |
| | R14 | AAAACCCATTCATT | | 421 |
| | Probe 14 | GTTTCGTTTTTTTTTTTTGGAAGG | | 422 |

TABLE 7-continued

Sequences of primer and probes for SIM2 gene qMSP

| Set | Primer | Sequences (5'→3') | Size of amplification product (bp) | SEQ ID NOs: |
|---|---|---|---|---|
| 386 | F786 | GTCGTCGTTTAGAT | 118 | 444 |
| | R14 | AAAACCCATTCATT | | 421 |
| | Probe 14 | GTTTCGTTTTTTTTTTTGGAAGG | | 422 |
| 387 | F787 | TCGTCGTTTAGATT | 117 | 445 |
| | R14 | AAAACCCATTCATT | | 421 |
| | Probe 14 | GTTTCGTTTTTTTTTTTGGAAGG | | 422 |
| 388 | F788 | CGTCGTTTAGATTT | 116 | 446 |
| | R14 | AAAACCCATTCATT | | 421 |
| | Probe 14 | GTTTCGTTTTTTTTTTTGGAAGG | | 422 |
| 389 | F789 | GTCGTTTAGATTTG | 115 | 447 |
| | R14 | AAAACCCATTCATT | | 421 |
| | Probe 14 | GTTTCGTTTTTTTTTTTGGAAGG | | 422 |
| 390 | F790 | TCGTTTAGATTTGA | 114 | 448 |
| | R14 | AAAACCCATTCATT | | 421 |
| | Probe 14 | GTTTCGTTTTTTTTTTTGGAAGG | | 422 |
| 391 | F791 | CGTTTAGATTTGAA | 113 | 449 |
| | R14 | AAAACCCATTCATT | | 421 |
| | Probe 14 | GTTTCGTTTTTTTTTTTGGAAGG | | 422 |
| 392 | F792 | GTTTAGATTTGAAG | 112 | 450 |
| | R14 | AAAACCCATTCATT | | 421 |
| | Probe 14 | GTTTCGTTTTTTTTTTTGGAAGG | | 422 |
| 393 | F793 | TTTAGATTTGAAGT | 111 | 451 |
| | R14 | AAAACCCATTCATT | | 421 |
| | Probe 14 | GTTTCGTTTTTTTTTTTGGAAGG | | 422 |
| 394 | F794 | TTAGATTTGAAGTT | 110 | 452 |
| | R14 | AAAACCCATTCATT | | 421 |
| | Probe 14 | GTTTCGTTTTTTTTTTTGGAAGG | | 422 |
| 395 | F795 | TAGATTTGAAGTTC | 109 | 452 |
| | R14 | AAAACCCATTCATT | | 421 |
| | Probe 14 | GTTTCGTTTTTTTTTTTGGAAGG | | 422 |
| 396 | F796 | AGATTTGAAGTTCG | 108 | 452 |
| | R14 | AAAACCCATTCATT | | 421 |
| | Probe 14 | GTTTCGTTTTTTTTTTTGGAAGG | | 422 |
| 397 | F797 | GATTTGAAGTTCGG | 107 | 455 |
| | R14 | AAAACCCATTCATT | | 421 |
| | Probe 14 | GTTTCGTTTTTTTTTTTGGAAGG | | 422 |
| 398 | F798 | ATTTGAAGTTCGGT | 106 | 456 |
| | R14 | AAAACCCATTCATT | | 421 |
| | Probe 14 | GTTTCGTTTTTTTTTTTGGAAGG | | 422 |
| 399 | F799 | TTTGAAGTTCGGTT | 105 | 457 |
| | R14 | AAAACCCATTCATT | | 421 |
| | Probe 14 | GTTTCGTTTTTTTTTTTGGAAGG | | 422 |
| 400 | F800 | TTGAAGTTCGGTTT | 104 | 458 |
| | R14 | AAAACCCATTCATT | | 421 |
| | Probe 14 | GTTTCGTTTTTTTTTTTGGAAGG | | 422 |
| 401 | F835 | TAATTAAGGAGATTTTTGGCGATC | 88 | 459 |
| | R17 | ACGAAICACACTCGAACACG | | 460 |
| | Probe 16 | ATCGTTTTAGTAGTTTTTGTCGCGTG CG | | 461 |

As a result of evaluating methylation of SIM2 gene using urine cell DNA from normal and bladder cancer patients, it was found that the sensitivity of SIM2 gene for bladder cancer diagnosis was 75% (15/20)~90.0% (18/20) and the high specificity of the SIM2 gene was 85% (3/20)~95% (1/20). Such results suggest that the SIM2 methylation biomarker gene is highly useful for early diagnosis of bladder cancer.

TABLE 8

Evaluation of ability to diagnose bladder cancer using SIM2 gene

| Set of primers and probes | Cut-off (Ct) | Sensitivity (%), n = 20 | Specificity (%), n = 20 |
|---|---|---|---|
| 1 | <30.1 | 85 | 80 |
| 2 | <30.0 | 90 | 80 |
| 3 | <30.3 | 75 | 90 |
| 4 | <30.1 | 85 | 85 |
| 5 | <30.0 | 90 | 85 |
| 6 | <30.5 | 85 | 90 |
| 7 | <30.5 | 85 | 90 |
| 8 | <30.2 | 90 | 80 |
| 9 | <30.3 | 90 | 85 |
| 10 | <30.5 | 75 | 95 |
| 11 | <30.0 | 80 | 90 |
| 12 | <30.1 | 80 | 90 |
| 13 | <30.0 | 85 | 90 |
| 14 | <30.2 | 90 | 90 |
| 15 | <30.3 | 75 | 90 |
| 16 | <30.5 | 80 | 90 |
| 17 | <30.0 | 80 | 85 |
| 18 | <30.3 | 85 | 90 |
| 19 | <30.1 | 80 | 90 |
| 20 | <30.0 | 75 | 90 |
| 21 | <30.5 | 85 | 90 |
| 22 | <30.5 | 85 | 90 |
| 23 | <30.5 | 75 | 90 |
| 24 | <30.2 | 75 | 90 |
| 25 | <30.3 | 80 | 90 |
| 26 | <30.5 | 85 | 85 |
| 27 | <30.0 | 90 | 80 |
| 28 | <30.1 | 85 | 90 |
| 29 | <30.0 | 85 | 90 |
| 30 | <30.1 | 85 | 80 |
| 31 | <30.0 | 90 | 80 |
| 32 | <30.2 | 90 | 80 |
| 33 | <30.0 | 90 | 80 |
| 34 | <30.1 | 85 | 85 |
| 35 | <30.0 | 90 | 85 |
| 36 | <30.3 | 90 | 85 |
| 37 | <30.0 | 80 | 85 |
| 38 | <30.5 | 85 | 85 |
| 39 | <30.3 | 75 | 90 |
| 40 | <30.5 | 85 | 90 |
| 41 | <30.5 | 85 | 95 |
| 42 | <30.0 | 80 | 90 |
| 43 | <30.1 | 80 | 90 |
| 44 | <30.0 | 85 | 90 |
| 45 | <30.2 | 90 | 90 |
| 46 | <30.3 | 75 | 95 |
| 47 | <30.5 | 80 | 90 |
| 48 | <30.3 | 85 | 90 |
| 49 | <30.1 | 80 | 95 |
| 50 | <30.0 | 75 | 90 |
| 51 | <30.5 | 85 | 90 |
| 52 | <30.5 | 85 | 95 |
| 53 | <30.5 | 75 | 95 |
| 54 | <30.2 | 75 | 90 |
| 55 | <30.3 | 80 | 90 |
| 56 | <30.1 | 85 | 90 |
| 57 | <30.0 | 85 | 90 |
| 58 | <30.5 | 75 | 95 |
| 59 | <30.1 | 85 | 80 |
| 60 | <30.5 | 75 | 95 |
| 61 | <30.3 | 75 | 95 |
| 62 | <30.1 | 80 | 95 |
| 63 | <30.5 | 85 | 95 |
| 64 | <30.5 | 75 | 95 |

TABLE 8-continued

Evaluation of ability to diagnose bladder cancer using SIM2 gene

| Set of primers and probes | Cut-off (Ct) | Sensitivity (%), n = 20 | Specificity (%), n = 20 |
|---|---|---|---|
| 65 | <30.5 | 75 | 95 |
| 66 | <30.3 | 75 | 90 |
| 67 | <30.5 | 85 | 90 |
| 68 | <30.5 | 85 | 90 |
| 69 | <30.0 | 80 | 90 |
| 70 | <30.1 | 80 | 90 |
| 71 | <30.0 | 85 | 90 |
| 72 | <30.2 | 90 | 90 |
| 73 | <30.3 | 75 | 85 |
| 74 | <30.5 | 80 | 85 |
| 75 | <30.3 | 85 | 90 |
| 76 | <30.1 | 80 | 90 |
| 77 | <30.0 | 75 | 90 |
| 78 | <30.5 | 85 | 95 |
| 79 | <30.5 | 85 | 95 |
| 80 | <30.5 | 75 | 90 |
| 81 | <30.2 | 75 | 90 |
| 82 | <30.3 | 80 | 95 |
| 83 | <30.1 | 85 | 90 |
| 84 | <30.0 | 85 | 90 |
| 85 | <30.3 | 75 | 85 |
| 86 | <30.5 | 85 | 90 |
| 87 | <30.5 | 85 | 90 |
| 88 | <30.0 | 80 | 95 |
| 89 | <30.1 | 80 | 90 |
| 90 | <30.0 | 85 | 90 |
| 91 | <30.2 | 90 | 90 |
| 92 | <30.5 | 80 | 95 |
| 93 | <30.3 | 85 | 90 |
| 94 | <30.0 | 75 | 90 |
| 95 | <30.5 | 85 | 90 |
| 96 | <30.2 | 75 | 95 |
| 97 | <30.3 | 80 | 90 |
| 98 | <30.1 | 85 | 90 |
| 99 | <30.0 | 85 | 90 |
| 100 | <30.1 | 85 | 85 |
| 101 | <30.0 | 90 | 85 |
| 102 | <30.3 | 90 | 85 |
| 103 | <30.0 | 80 | 85 |
| 104 | <30.5 | 85 | 85 |
| 105 | <30.1 | 85 | 85 |
| 106 | <30.0 | 90 | 85 |
| 107 | <30.3 | 90 | 85 |
| 108 | <30.0 | 80 | 85 |
| 109 | <30.5 | 85 | 85 |
| 110 | <30.0 | 90 | 80 |
| 111 | <30.2 | 90 | 80 |
| 112 | <30.0 | 90 | 80 |
| 113 | <30.1 | 85 | 80 |
| 114 | <30.0 | 90 | 80 |
| 115 | <30.2 | 90 | 80 |
| 116 | <30.0 | 90 | 80 |
| 117 | <30.1 | 80 | 90 |
| 118 | <30.0 | 75 | 90 |
| 119 | <30.5 | 85 | 90 |
| 120 | <30.5 | 85 | 90 |
| 121 | <30.5 | 75 | 90 |
| 122 | <30.2 | 75 | 90 |
| 123 | <30.3 | 80 | 90 |
| 124 | <30.5 | 85 | 85 |
| 125 | <30.0 | 90 | 80 |
| 126 | <30.1 | 85 | 90 |
| 127 | <30.0 | 85 | 90 |
| 128 | <30.1 | 85 | 80 |
| 129 | <30.0 | 90 | 80 |
| 130 | <30.2 | 90 | 80 |
| 131 | <30.0 | 90 | 80 |
| 132 | <30.1 | 85 | 85 |
| 133 | <30.0 | 90 | 85 |
| 134 | <30.3 | 90 | 85 |
| 135 | <30.0 | 80 | 85 |
| 136 | <30.5 | 85 | 85 |
| 137 | <30.3 | 75 | 90 |
| 138 | <30.5 | 85 | 90 |
| 139 | <30.5 | 85 | 90 |

TABLE 8-continued

| Evaluation of ability to diagnose bladder cancer using SIM2 gene | | | |
|---|---|---|---|
| Set of primers and probes | Cut-off (Ct) | Sensitivity (%), n = 20 | Specificity (%), n = 20 |
| 140 | <30.0 | 80 | 90 |
| 141 | <30.1 | 80 | 90 |
| 142 | <30.0 | 85 | 90 |
| 143 | <30.2 | 90 | 90 |
| 144 | <30.3 | 75 | 95 |
| 145 | <30.5 | 80 | 90 |
| 146 | <30.3 | 85 | 90 |
| 147 | <30.1 | 80 | 95 |
| 148 | <30.0 | 75 | 90 |
| 149 | <30.5 | 85 | 90 |
| 150 | <30.5 | 85 | 95 |
| 151 | <30.5 | 75 | 95 |
| 152 | <30.2 | 75 | 90 |
| 153 | <30.3 | 80 | 90 |
| 154 | <30.1 | 85 | 90 |
| 155 | <30.0 | 85 | 90 |
| 156 | <30.5 | 75 | 95 |
| 157 | <30.1 | 85 | 80 |
| 158 | <30.5 | 75 | 95 |
| 159 | <30.3 | 75 | 95 |
| 160 | <30.1 | 80 | 95 |
| 161 | <30.5 | 85 | 95 |
| 162 | <30.5 | 75 | 95 |
| 163 | <30.5 | 75 | 95 |
| 164 | <30.3 | 75 | 90 |
| 165 | <30.5 | 85 | 90 |
| 166 | <30.5 | 85 | 90 |
| 167 | <30.0 | 80 | 90 |
| 168 | <30.1 | 80 | 90 |
| 169 | <30.0 | 85 | 95 |
| 170 | <30.2 | 90 | 95 |
| 171 | <30.3 | 75 | 90 |
| 172 | <30.5 | 80 | 90 |
| 173 | <30.3 | 85 | 90 |
| 174 | <30.1 | 80 | 90 |
| 175 | <30.0 | 75 | 90 |
| 176 | <30.5 | 85 | 85 |
| 177 | <30.5 | 85 | 85 |
| 178 | <30.5 | 75 | 90 |
| 179 | <30.2 | 75 | 90 |
| 180 | <30.3 | 80 | 90 |
| 181 | <30.1 | 85 | 90 |
| 182 | <30.0 | 85 | 95 |
| 183 | <30.3 | 75 | 90 |
| 184 | <30.5 | 85 | 85 |
| 185 | <30.5 | 85 | 90 |
| 186 | <30.0 | 80 | 90 |
| 187 | <30.1 | 80 | 90 |
| 188 | <30.0 | 85 | 90 |
| 189 | <30.2 | 90 | 85 |
| 190 | <30.5 | 80 | 90 |
| 191 | <30.3 | 85 | 90 |
| 192 | <30.0 | 75 | 95 |
| 193 | <30.5 | 85 | 90 |
| 194 | <30.2 | 75 | 90 |
| 195 | <30.3 | 80 | 95 |
| 196 | <30.1 | 85 | 90 |
| 197 | <30.0 | 85 | 90 |
| 198 | <30.1 | 85 | 85 |
| 199 | <30.0 | 90 | 85 |
| 200 | <30.1 | 85 | 85 |
| 201 | <30.3 | 85 | 90 |
| 202 | <30.1 | 85 | 85 |
| 203 | <30.2 | 75 | 90 |
| 204 | <30.5 | 85 | 90 |
| 205 | <30.2 | 90 | 85 |
| 206 | <30.5 | 85 | 90 |
| 207 | <30.5 | 85 | 85 |
| 208 | <30.3 | 80 | 90 |
| 209 | <30.5 | 85 | 85 |
| 210 | <30.0 | 75 | 90 |
| 211 | <30.3 | 75 | 90 |
| 212 | <30.0 | 80 | 90 |
| 213 | <30.5 | 85 | 90 |
| 214 | <30.5 | 75 | 95 |
| 215 | <30.5 | 75 | 95 |
| 216 | <30.1 | 85 | 80 |
| 217 | <30.3 | 80 | 90 |
| 218 | <30.5 | 85 | 90 |
| 219 | <30.0 | 75 | 90 |
| 220 | <30.3 | 75 | 95 |
| 221 | <30.0 | 80 | 90 |
| 222 | <30.5 | 85 | 90 |
| 223 | <30.0 | 80 | 85 |
| 224 | <30.0 | 90 | 80 |
| 225 | <30.2 | 90 | 80 |
| 226 | <30.1 | 85 | 90 |
| 227 | <30.2 | 75 | 90 |
| 228 | <30.5 | 75 | 90 |
| 229 | <30.1 | 80 | 90 |
| 230 | <30.1 | 85 | 80 |
| 231 | <30.0 | 90 | 80 |
| 232 | <30.0 | 80 | 85 |
| 233 | <30.5 | 85 | 85 |
| 234 | <30.0 | 80 | 85 |
| 235 | <30.0 | 85 | 90 |
| 236 | <30.5 | 85 | 90 |
| 237 | <30.0 | 75 | 90 |
| 238 | <30.0 | 85 | 90 |
| 239 | <30.5 | 85 | 90 |
| 240 | <30.3 | 75 | 85 |
| 241 | <30.2 | 75 | 90 |
| 242 | <30.0 | 75 | 90 |
| 243 | <30.1 | 80 | 90 |
| 244 | <30.2 | 90 | 90 |
| 245 | <30.5 | 85 | 90 |
| 246 | <30.5 | 85 | 90 |
| 247 | <30.5 | 85 | 95 |
| 248 | <30.1 | 85 | 80 |
| 249 | <30.5 | 75 | 95 |
| 250 | <30.2 | 75 | 90 |
| 251 | <30.0 | 75 | 90 |
| 252 | <30.1 | 80 | 95 |
| 253 | <30.2 | 90 | 90 |
| 254 | <30.5 | 85 | 95 |
| 255 | <30.5 | 85 | 90 |
| 256 | <30.3 | 90 | 85 |
| 257 | <30.2 | 90 | 80 |
| 258 | <30.0 | 90 | 80 |
| 259 | <30.0 | 90 | 80 |
| 260 | <30.5 | 75 | 90 |
| 261 | <30.5 | 85 | 90 |
| 262 | <30.3 | 85 | 90 |
| 263 | <30.2 | 90 | 90 |
| 264 | <30.0 | 85 | 90 |
| 265 | <30.3 | 90 | 85 |
| 266 | <30.0 | 90 | 85 |
| 267 | <30.1 | 85 | 80 |
| 268 | <30.5 | 85 | 90 |
| 269 | <30.5 | 75 | 95 |
| 270 | <30.3 | 75 | 90 |
| 271 | <30.1 | 80 | 90 |
| 272 | <30.2 | 75 | 90 |
| 273 | <30.0 | 85 | 90 |
| 274 | <30.0 | 90 | 80 |
| 275 | <30.3 | 75 | 90 |
| 276 | <30.1 | 80 | 90 |
| 277 | <30.5 | 80 | 90 |
| 278 | <30.1 | 85 | 90 |
| 279 | <30.3 | 75 | 90 |
| 280 | <30.1 | 80 | 90 |
| 281 | <30.3 | 85 | 90 |
| 282 | <30.3 | 80 | 95 |
| 283 | <30.0 | 80 | 95 |
| 284 | <30.2 | 90 | 90 |
| 285 | <30.1 | 85 | 85 |
| 286 | <30.2 | 90 | 80 |
| 287 | <30.0 | 90 | 80 |
| 288 | <30.0 | 75 | 90 |
| 289 | <30.3 | 80 | 90 |

TABLE 8-continued

Evaluation of ability to diagnose bladder cancer using SIM2 gene

| Set of primers and probes | Cut-off (Ct) | Sensitivity (%), n = 20 | Specificity (%), n = 20 |
|---|---|---|---|
| 290 | <30.1 | 85 | 85 |
| 291 | <30.1 | 80 | 90 |
| 292 | <30.3 | 85 | 90 |
| 293 | <30.5 | 75 | 95 |
| 294 | <30.0 | 85 | 90 |
| 295 | <30.3 | 75 | 95 |
| 296 | <30.1 | 80 | 90 |
| 297 | <30.5 | 80 | 90 |
| 298 | <30.5 | 85 | 85 |
| 299 | <30.0 | 80 | 90 |
| 300 | <30.0 | 85 | 90 |
| 301 | <30.5 | 80 | 90 |
| 302 | <30.0 | 85 | 90 |
| 303 | <30.0 | 75 | 95 |
| 304 | <30.1 | 80 | 90 |
| 305 | <30.1 | 85 | 90 |
| 306 | <30.2 | 75 | 90 |
| 307 | <30.3 | 85 | 90 |
| 308 | <30.5 | 85 | 90 |
| 309 | <30.5 | 85 | 95 |
| 310 | <30.5 | 75 | 95 |
| 311 | <30.2 | 75 | 90 |
| 312 | <30.5 | 85 | 90 |
| 313 | <30.3 | 90 | 85 |
| 314 | <30.0 | 85 | 90 |
| 315 | <30.5 | 85 | 85 |
| 316 | <30.0 | 90 | 80 |
| 317 | <30.0 | 90 | 80 |
| 318 | <30.3 | 90 | 85 |
| 319 | <30.3 | 80 | 90 |
| 320 | <30.5 | 85 | 90 |
| 321 | <30.5 | 75 | 90 |
| 322 | <30.5 | 85 | 95 |
| 323 | <30.3 | 75 | 85 |
| 324 | <30.0 | 85 | 90 |
| 325 | <30.1 | 80 | 95 |
| 326 | <30.5 | 75 | 95 |
| 327 | <30.3 | 80 | 90 |
| 328 | <30.5 | 75 | 95 |
| 329 | <30.5 | 85 | 90 |
| 330 | <30.3 | 75 | 95 |
| 331 | <30.0 | 80 | 90 |
| 332 | <30.0 | 80 | 85 |
| 333 | <30.1 | 85 | 85 |
| 334 | <30.1 | 85 | 90 |
| 335 | <30.5 | 85 | 90 |
| 336 | <30.0 | 80 | 85 |
| 337 | <30.1 | 80 | 90 |
| 338 | <30.3 | 75 | 90 |
| 339 | <30.5 | 85 | 90 |
| 340 | <30.0 | 90 | 80 |
| 341 | <30.2 | 90 | 80 |
| 342 | <30.0 | 80 | 90 |
| 343 | <30.5 | 80 | 90 |
| 344 | <30.5 | 85 | 85 |
| 345 | <30.1 | 85 | 80 |
| 346 | <30.5 | 85 | 85 |
| 347 | <30.0 | 85 | 90 |
| 348 | <30.3 | 85 | 90 |
| 349 | <30.5 | 85 | 95 |
| 350 | <30.0 | 85 | 90 |
| 351 | <30.5 | 80 | 85 |
| 352 | <30.5 | 85 | 95 |
| 353 | <30.0 | 85 | 90 |
| 354 | <30.1 | 80 | 90 |
| 355 | <30.3 | 85 | 90 |
| 356 | <30.2 | 75 | 95 |
| 357 | <30.0 | 90 | 85 |
| 358 | <30.1 | 85 | 85 |
| 359 | <30.5 | 85 | 85 |
| 360 | <30.2 | 90 | 80 |
| 361 | <30.5 | 85 | 90 |
| 362 | <30.1 | 85 | 80 |
| 363 | <30.5 | 85 | 85 |
| 364 | <30.0 | 85 | 90 |
| 365 | <30.5 | 80 | 90 |
| 366 | <30.5 | 85 | 95 |
| 367 | <30.1 | 85 | 90 |
| 368 | <30.1 | 80 | 95 |
| 369 | <30.3 | 75 | 90 |
| 370 | <30.2 | 90 | 95 |
| 371 | <30.5 | 75 | 90 |
| 372 | <30.0 | 85 | 95 |
| 373 | <30.3 | 85 | 90 |
| 374 | <30.0 | 90 | 85 |
| 375 | <30.3 | 80 | 95 |
| 376 | <30.5 | 80 | 90 |
| 377 | <30.3 | 75 | 90 |
| 378 | <30.1 | 80 | 90 |
| 379 | <30.0 | 85 | 95 |
| 380 | <30.5 | 75 | 95 |
| 381 | <30.2 | 90 | 90 |
| 382 | <30.3 | 75 | 90 |
| 383 | <30.0 | 90 | 85 |
| 384 | <30.0 | 90 | 80 |
| 385 | <30.5 | 85 | 90 |
| 386 | <30.0 | 90 | 85 |
| 387 | <30.3 | 90 | 85 |
| 388 | <30.1 | 85 | 90 |
| 389 | <30.5 | 80 | 95 |
| 390 | <30.1 | 85 | 90 |
| 391 | <30.5 | 75 | 95 |
| 392 | <30.3 | 75 | 95 |
| 393 | <30.0 | 90 | 85 |
| 394 | <30.0 | 75 | 90 |
| 395 | <30.1 | 85 | 85 |
| 396 | <30.3 | 80 | 90 |
| 397 | <30.5 | 75 | 95 |
| 398 | <30.0 | 80 | 90 |
| 399 | <30.0 | 90 | 80 |
| 400 | <30.1 | 80 | 95 |
| 401 | <30.1 | 85 | 85 |

INDUSTRIAL APPLICABILITY

As described above in detail, the present invention provides a kit and nucleic acid chip for diagnosing bladder cancer, which can detect the methylation of CpG islands of bladder cancer-specific marker genes. It is possible to diagnose bladder cancer at an early stage of transformation using the diagnostic kit or nucleic acid chip of the present invention, thus enabling early diagnosis of bladder cancer, and the diagnostic kit or nucleic acid chip can diagnose bladder cancer in a more accurate and rapid manner compared to a conventional method.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method for detecting CpG methylation of SIM2 (single-minded homolog 2 (*Drosophila*)) gene, the method comprising the steps of:

(a) isolating a genomic DNA from a clinical sample;

(b) treating the genomic DNA from step (a) with bisulfite; and (c) determining hypermethylation of the CpG of the SIM2 gene in the bisulfite-treated genomic DNA from step (b) by using primer(s) to amplify a methylated CpG of the bisulfite-treated SIM2 gene, wherein the primer(s) comprises sequence(s) selected from the group consisting of SEQ ID NOs: 43-44, 46-63, 65-126, 128-189, 191-232, 234-295, 297-358, 360-421 and 423-460.

2. The method according to claim 1, wherein the step (c) is performed by one selected from the group consisting of PCR, methylation specific PCR, real-time methylation specific PCR, PCR using a methylated DNA-specific binding protein, quantitative PCR, pyrosequencing, and bisulfite sequencing.

3. The method according to claim 1, wherein step (c) comprises examining a CpG methylation of a promoter or exon region of SIM2 in the clinical sample.

4. The method according to claim 3, wherein the promoter comprises a DNA sequence represented in SEQ ID NO: 40.

5. The method according to claim 1, wherein the method further comprises the step of examining CpG methylation of a gene selected from the group consisting of TBX5—T-box 5; CDX2—caudal type homeobox transcription factor 2; CYP1B1—cytochrome P450, family 1, subfamily B, polypeptide 1; VSX1—visual system homeobox 1 homolog, CHX10—like (zebrafish); HOXA11—homeobox A11; T)—T, brachyury homolog (mouse); PENK—proenkephalin; PAQR9—progestin and adipoQ receptor family member IV; and LHX2—LIM Homeobox 2.

6. The method according to claim 5, wherein the step of examining comprises examining CpG methylation of a promoter or exon region of the gene selected from the group consisting of TBX5; CDX2; CYP1B1; VSX1; HOXA11; T; PENK; PAQR9; and LHX2.

7. The method according to claim 1, wherein the method further comprises the step of contacting at least one nucleic acid isolated from the clinical sample with an agent capable of determining a CpG methylation status of SIM2 gene.

8. The method according to claim 1, wherein the primer(s) for amplifying a methylated CpG of SIM2 comprising at least one or more CpG dinucleotide in a region which hybridizes to the methylated CpG of SIM2.

9. The method according to claim 1, further comprising probe(s) capable of hybridizing with a methylated CpG of SIM2 comprising at least one or more CpG dinucleotide in a region which hybridizes to the methylated CpG of SIM2.

10. The method according to claim 1, further comprising probe(s) capable of hybridizing with a methylated CpG of SIM2 comprising sequence(s) selected from the group consisting of SEQ ID NOs:

45, 64, 127, 190, 233, 296, 359, 422 and 461.

11. A method for detecting CpG methylation of SIM2—single-minded homolog 2 (*Drosophila*) gene for bladder carcinoma or bladder cell proliferative disorder diagnosis, the method comprising the steps of:

(a) isolating a genomic DNA from a clinical sample;

(b) treating the genomic DNA from step (a) with bisulfite; and (c) determining hypermethylation of the CpG of the SIM2 gene in the bisulfite-treated genomic DNA from step (b) by using primer(s) to amplify a methylated CpG of the bisulfite-treated SIM2 gene, wherein a bladder carcinoma or bladder cell proliferative disorder is detected in the human subject based on increased CpG methylation of the SIM2 gene relative to that of a control, wherein the primer(s) comprises sequence(s) selected from the group consisting of SEQ ID NOs: 43-44, 46-63, 65-126, 128-189, 191-232, 234-295, 297-358, 360-421 and 423-460.

12. The method according to claim 11, wherein the step (c) is performed by one selected from the group consisting of PCR, methylation specific PCR, real-time methylation specific PCR, PCR using a methylated DNA-specific binding protein, quantitative PCR, pyrosequencing, and bisulfite sequencing.

13. The method according to claim 12, wherein the clinical sample is tissue, cell, blood, urine, serum or plasma from a patient suspected of cancer or a subject to be diagnosed.

14. The method according to claim 11, wherein step (c) comprises examining a CpG methylation of a promoter or exon region of SIM2 in the clinical sample.

15. The method according to claim 14, wherein the promoter comprises a DNA sequence represented in SEQ ID NO: 40.

16. The method according to claim 11, wherein the method further comprises the step of examining CpG methylation of a gene selected from the group consisting of TBX5—T-box 5; CDX2—caudal type homeobox transcription factor 2; CYP1B1—cytochrome P450, family 1, subfamily B, polypeptide 1; VSX1—visual system homeobox 1 homolog, CHX10—like (zebrafish); HOXA11—homeobox A11; T)—T, brachyury homolog (mouse); PENK—proenkephalin; PAQR9—progestin and adipoQ receptor family member IV; and LHX2—LIM Homeobox 2.

17. The method according to claim 16, wherein the step of examining comprises examining CpG methylation of a promoter or exon region of the gene selected from the group consisting of TBX5; CDX2; CYP1B1; VSX1; HOXA11; T; PENK; PAQR9; and LHX2.

18. The method according to claim 11, wherein the method further comprises the step of contacting at least one nucleic acid isolated from the clinical sample with an agent capable of determining a CpG methylation status of SIM2 gene.

19. The method according to claim 11, wherein the primer(s) for amplifying a methylated CpG of SIM2 comprising at least one or more CpG dinucleotide in a region which hybridizes to the methylated CpG of SIM2.

20. The method according to claim 11, further comprising probe(s) capable of hybridizing with a methylated CpG of SIM2 comprising at least one or more CpG dinucleotide in a region which hybridizes to the methylated CpG of SIM2.

21. The method according to claim 11, further comprising probe(s) capable of hybridizing with a methylated CpG of SIM2 comprising sequence(s) selected from the group consisting of SEQ ID NOs: 45, 64, 127, 190, 233, 296, 359, 422 and 461.

* * * * *